(12) United States Patent
Cai et al.

(10) Patent No.: US 10,830,855 B2
(45) Date of Patent: Nov. 10, 2020

(54) FREE-BREATHING CINE DENSE IMAGING

(71) Applicant: University of Virginia Patent Foundation, Charlottesville, VA (US)

(72) Inventors: Xiaoying Cai, Charlottesville, VA (US); Frederick H. Epstein, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 16/368,218

(22) Filed: Mar. 28, 2019

(65) Prior Publication Data
US 2019/0302211 A1    Oct. 3, 2019

Related U.S. Application Data

(60) Provisional application No. 62/649,289, filed on Mar. 28, 2018.

(51) Int. Cl.
*G01R 33/565* (2006.01)
*G01R 33/56* (2006.01)
(Continued)

(52) U.S. Cl.
CPC ...... *G01R 33/56509* (2013.01); *A61B 5/0044* (2013.01); *A61B 5/055* (2013.01);
(Continued)

(58) Field of Classification Search
CPC .......... G01R 33/56509; G01R 33/5673; G01R 33/5608; G01R 33/56325; G01R 33/4824; G01R 33/5676; A61B 5/0044; A61B 5/7203; A61B 2576/023; A61B 5/055; G06T 7/20; G06T 5/002; G06T 7/0014;
(Continued)

(56) References Cited

U.S. PATENT DOCUMENTS

2016/0038112 A1* 2/2016 Wiemker ............... A61B 6/463
378/98.11
2017/0307712 A1* 10/2017 Cai .................. G01R 33/56316

OTHER PUBLICATIONS

Aletras AH, Balaban RS, Wen H. High-resolution strain analysis of the human heart with fast-DENSE. Journal of Magnetic Resonance. 1999;140(1):41-57.
(Continued)

Primary Examiner — G.M. A Hyder
(74) Attorney, Agent, or Firm — Meunier Carlin & Curfman LLC

(57) ABSTRACT

In some aspects, the disclosed technology relates to free-breathing cine DENSE (displacement encoding with stimulated echoes) imaging. In some embodiments, self-gated free-breathing adaptive acquisition reduces free-breathing artifacts by minimizing the residual energy of the phase-cycled T1-relaxation signal, and the acquisition of the k-space data is adaptively repeated with the highest residual T1-echo energy. In some embodiments, phase-cycled spiral interleaves are identified at matched respiratory phases by minimizing the residual signal due to T1 relaxation after phase-cycling subtraction; image-based navigators (iNAVs) are reconstructed from matched phase-cycled interleaves that are comprised of the stimulated echo iNAVs (ste-iNAVs), wherein the ste-iNAVs are used for motion estimation and compensation of k-space data.

18 Claims, 25 Drawing Sheets
(14 of 25 Drawing Sheet(s) Filed in Color)

(51) Int. Cl.
- G06T 5/50 (2006.01)
- G06T 11/00 (2006.01)
- G06T 7/00 (2017.01)
- G06T 5/00 (2006.01)
- G06T 7/20 (2017.01)
- A61B 5/055 (2006.01)
- A61B 5/00 (2006.01)
- G01R 33/567 (2006.01)

(52) U.S. Cl.
CPC ........ A61B 5/7203 (2013.01); G01R 33/5608 (2013.01); G01R 33/5673 (2013.01); G06T 5/002 (2013.01); G06T 5/50 (2013.01); G06T 7/0014 (2013.01); G06T 7/20 (2013.01); G06T 11/005 (2013.01); G06T 11/008 (2013.01); A61B 2576/023 (2013.01); G06T 2207/10088 (2013.01); G06T 2207/20224 (2013.01); G06T 2207/30048 (2013.01); G06T 2211/424 (2013.01)

(58) Field of Classification Search
CPC ....... G06T 11/008; G06T 11/005; G06T 5/50; G06T 2211/424; G06T 2207/30048; G06T 2207/10088; G06T 2207/20224
See application file for complete search history.

(56) References Cited

OTHER PUBLICATIONS

Anderson AW, Gore JC. Analysis and correction of motion artifacts in diffusion weighted imaging. Magnetic resonance in medicine. 1994;32(3):379-87.
Auger, Daniel A., et al. "Imaging left-ventricular mechanical activation in heart failure patients using cine DENSE MRI: Validation and implications for cardiac resynchronization therapy." Journal of Magnetic Resonance Imaging 46.3 (2017): 887-896.
Axel L, Dougherty L. Heart wall motion: improved method of spatial modulation of magnetization for MR imaging. Radiology. 1989;172(2):349-50.
Axel L, Dougherty L. MR imaging of motion with spatial modulation of magnetization. Radiology. 1989;171(3):841-5.
Barth M, Breuer F, Koopmans PJ, Norris DG, Poser BA. Simultaneous multislice (SMS) imaging techniques. Magnetic resonance in medicine. 2016;75(1):63-81.
Bilchick KC, Kuruvilla S, Hamirani YS, Ramachandran R, Clarke SA, Parker KM, et al. Impact of mechanical activation, scar, and electrical timing on cardiac resynchronization therapy response and clinical outcomes. Journal of the American College of Cardiology. 2014;63(16):1657-66.
Breuer FA, Blaimer M, Mueller MF, Seiberlich N, Heidemann RM, Griswold MA, et al. Controlled aliasing in volumetric parallel imaging (2D CAIPIRINHA). Magnetic Resonance in Medicine: An Official Journal of the International Society for Magnetic Resonance in Medicine. 2006;55(3):549-56.
Cai, Xiaoying, and Frederick H. Epstein. "Free-breathing cine DENSE MRI using phase cycling with matchmaking and stimulated-echo image-based navigators." Magnetic resonance in medicine 80.5 (2018): 1907-1921.
Chow K, Yang Y, Shaw P, Kramer CM, Salerno M. Robust free-breathing SASHA T 1 mapping with high-contrast image registration. Journal of Cardiovascular Magnetic Resonance. 2016;18(1):47.
Constantinides CD, Atalar E, McVeigh ER. Signal-to-noise measurements in magnitude images from NMR phased arrays. Magnetic Resonance in Medicine. 1997;38(5):852-7.
Dietrich 0, Raya JG, Reeder SB, Ingrisch M, Reiser MF, Schoenberg SO. Influence of multichannel combination, parallel imaging and other reconstruction techniques on MRI noise characteristics. Magnetic resonance imaging. 2008;26(6):754-62.

Ehman RL, Felmlee JP. Adaptive technique for high-definition MR imaging of moving structures. Radiology. 1989;173(1):255-63.
Fahmy AS, Ibrahim E-SH, Osman NF. Spectrally-Presaturated Modulation (SPM): An efficient fat suppression technique for STEAM-based cardiac imaging sequences. Magnetic resonance imaging. 2017;37:209-15.
Feng L, Axel L, Chandarana H, Block KT, Sodickson DK, Otazo R. XD-GRASP: golden-angle radial MRI with reconstruction of extra motion-state dimensions using compressed sensing. Magnetic resonance in medicine. 2016;75(2):775-88.
Fessler JA, Sutton BP. Nonuniform fast Fourier transforms using min-max interpolation. IEEE Transactions on Signal Processing. 2003;51(2):560-74.
Gilliam AD, Epstein FH. Automated motion estimation for 2-D cine DENSE MRI. IEEE transactions on medical imaging. 2012;31(9):1669-81.
Gilson WD, Yang Z, French BA, Epstein FH. Complementary displacement-encoded MRI for contrast-enhanced infarct detection and quantification of myocardial function in mice. Magnetic Resonance in Medicine: An Official Journal of the International Society for Magnetic Resonance in Medicine. 2004;51(4):74452.
Goto Y, Ishida M, Takase S, Sigfridsson A, Uno M, Nagata M, et al. Comparison of Displacement Encoding With Stimulated Echoes to Magnetic Resonance Feature Tracking for the Assessment of Myocardial Strain in Patients With Acute Myocardial Infarction. The American Journal of Cardiology. 2017;119(10):1542-7.
Griswold MA, Jakob PM, Heidemann RM, Nittka M, Jellus V, Wang J, et al. Generalized autocalibrating partially parallel acquisitions (GRAPPA). Magnetic Resonance in Medicine: An Official Journal of the International Society for Magnetic Resonance in Medicine. 2002;47(6):1202-10.
Gudbjartsson H, Patz S. The Rician distribution of noisy MRI data. Magnetic resonance in medicine 1995;34(6):910-914.
Hamlet SM, Haggerty CM, Suever JD, Wehner GJ, Andres KN, Powell DK, et al. Optimal configuration of respiratory navigator gating for the quantification of left ventricular strain using spiral cine displacement encoding with stimulated echoes (DENSE) MRI. Journal of Magnetic Resonance Imaging. 2017;45(3):786-94.
Hardy CJ, Zhao L, Zong X, Saranathan M, Yucel EK. Coronary MR angiography: respiratory motion correction with BACSPIN. Journal of Magnetic Resonance Imaging. 2003;17(2):170-6.
Henningsson M, Koken P, Stehning C, Razavi R, Prieto C, Botnar RM. Whole-heart coronary MR angiography with 2D self-navigated image reconstruction. Magnetic resonance in medicine. 2012;67(2):437-45.
Irarrazabal P, Meyer CH, Nishimura DG, Macovski A. Inhomogeneity correction using an estimated linear field map. Magnetic resonance in medicine. 1996;35(2):278-82.
Jing L, Binkley CM, Suever JD, Umasankar N, Haggerty CM, Rich J, et al. Cardiac remodeling and dysfunction in childhood obesity: a cardiovascular magnetic resonance study. Journal of Cardiovascular Magnetic Resonance. 2016;18(1):28.
Johnson CL, McGarry MD, Van Houten EE, Weaver JB, Paulsen KD, Sutton BP, et al. Magnetic resonance elastography of the brain using multishot spiral readouts with self-navigated motion correction. Magnetic resonance in medicine. 2013;70(2):404-12.
Kellman P, Larson AC, Hsu LY, Chung YC, Simonetti OP, McVeigh ER, et al. Motion-corrected free-breathing delayed enhancement imaging of myocardial infarction. Magnetic resonance in medicine. 2005;53(1):194-200.
Kihlberg J, Haraldsson H, Sigfridsson A, Ebbers T, Engvall JE. Clinical experience of strain imaging using DENSE for detecting infarcted cardiac segments. Journal of Cardiovascular Magnetic Resonance. 2015;17(1):50.
Kim D, Gilson WD, Kramer CM, Epstein FH. Myocardial tissue tracking with two-dimensional cine displacement-encoded MR imaging: development and initial evaluation. Radiology 2004;230(3):862-871.
Kim YC, Narayanan SS, Nayak KS. Flexible retrospective selection of temporal resolution in real-time speech MRI using a golden-ratio spiral view order. Magnetic resonance in medicine. 2011;65(5):1365-71.

(56) References Cited

OTHER PUBLICATIONS

Knight-Scott J, Shanbhag DD, Dunham SA. A phase rotation scheme for achieving very short echo times with localized stimulated echo spectroscopy. Magnetic resonance imaging. 2005;23(8):871-6.
Lai P, Larson AC, Bi X, Jerecic R, Li D. A dual-projection respiratory self-gating technique for whole-heart coronary MRA. Journal of Magnetic Resonance Imaging. 2008;28(3):612-20.
Larson AC, Kellman P, Arai A, Hirsch GA, McVeigh E, Li D, et al. Preliminary investigation of respiratory self-gating for free-breathing segmented cine MRI. Magnetic Resonance in Medicine: An Official Journal of the International Society for Magnetic Resonance in Medicine. 2005;53(1):159-68.
Larson AC, White RD, Laub G, McVeigh ER, Li D, Simonetti OP. Self-gated cardiac cine MRI. Magnetic Resonance in Medicine. 2004;51(1):93-102.
Leung AO, Paterson I, Thompson RB. Free-breathing cine MRI. Magnetic resonance in medicine. 2008;60(3):709-17.
Li X, Han ET, Ma CB, Link TM, Newitt DC, Majumdar S. In vivo 3T spiral imaging based multi-slice T1p mapping of knee cartilage in osteoarthritis. Magnetic resonance in medicine. 2005;54(4):929-36.
Lin K, Meng L, Collins JD, Chowdhary V, Markl M, Carr JC. Reproducibility of cine displacement encoding with stimulated echoes (DENSE) in human subjects. Magnetic resonance imaging. 2017;35:148-53.
Lingala SG, Hu Y, DiBella E, Jacob M. Accelerated dynamic MRI exploiting sparsity and low-rank structure: kt SLR. IEEE transactions on medical imaging. 2011;30(5):1042-54.
Liu C, Bammer R, Kim Dh, Moseley ME. Self-navigated interleaved spiral (SNAILS): application to high-resolution diffusion tensor imaging. Magnetic Resonance in Medicine: An Official Journal of the International Society for Magnetic Resonance in Medicine. 2004;52(6):1388-96.
Liu J, Spincemaille P, Codella NC, Nguyen TD, Prince MR, Wang Y. Respiratory and cardiac self-gated free-breathing cardiac CINE imaging with multiecho 3D hybrid radial SSFP acquisition. Magnetic resonance in medicine. 2010;63(5):1230-7.
Lustig M, Donoho D, Pauly JM. Sparse MRI: The application of compressed sensing for rapid MR imaging. Magnetic Resonance in Medicine: An Official Journal of the International Society for Magnetic Resonance in Medicine. 2007;58(6):1182-95.
Lustig M, Santos JM, Donoho DL, Pauly JM, editors. K-t SPARSE: High frame rate dynamic MRI exploiting spatio-temporal sparsity. Proceedings of the 13th Annual Meeting of ISMRM, Seattle; 2006, 2420.
Mangion K, Carrick D, Carberry J, Mahrous A, McComb C, Gao H, et al. Comparative prognostic value of myocardial strain derived from DENSE CMR: the British Heart Foundation MR-MI study. The Lancet. 2017;389:S66.
Mills P, Chew W, Litt L, Moseley M. Localized imaging using stimulated echoes. Magnetic resonance in medicine. 1987;5(4):384-9.
Nehrke K, Bornert P, Manke D, Bock JC. Free-breathing cardiac MR imaging: study of implications of respiratory motion—initial results. Radiology. 2001;220(3):810-5.
Noll DC, Meyer CH, Pauly JM, Nishimura DG, Macovski A. A homogeneity correction method for magnetic resonance imaging with time-varying gradients. IEEE transactions on medical imaging. 1991;10(4):629-37.
Pedersen H, Kozerke S, Ringgaard S, Nehrke K, Kim WY. k-t PCA: temporally constrained k-t BLAST reconstruction using principal component analysis. Magnetic resonance in medicine. 2009;62(3):706-16.
Pruessmann KP, Weiger M, Scheidegger MB, Boesiger P. SENSE: sensitivity encoding for fast MRI. Magnetic resonance in medicine. 1999;42(5):952-62.

Sachs TS, Meyer CH, Irarrazabal P, Hu BS, Nishimura DG, Macovski A. The diminishing variance algorithm for real-time reduction of motion artifacts in MRI. Magnetic resonance in medicine. 1995;34(3):412-22.
Sachs TS, Meyer CH, Pauly JM, Hu BS, Nishimura DG, Macovski A. The real-time interactive 3-D-DVA for robust coronary MRA. IEEE transactions on medical imaging. 2000;19(2):73-9.
Segmentation AHAWGoM, Imaging: RfC, Cerqueira MD, Weissman NJ, Dilsizian V, Jacobs AK, et al. Standardized myocardial segmentation and nomenclature for tomographic imaging of the heart: a statement for healthcare professionals from the Cardiac Imaging Committee of the Council on Clinical Cardiology of the American Heart Association. Circulation. 2002;105(4):539-42.
Shechter G, McVeigh ER, editors. MR motion correction of 3D affine deformations. Proceedings Int Soc Mag Reson Med; 2003: Citeseer, 1 page.
Spottiswoode BS, Zhong X, Hess AT, Kramer C, Meintjes EM, Mayosi BM, et al. Tracking myocardial motion from cine DENSE images using spatiotemporal phase unwrapping and temporal fitting. IEEE transactions on medical imaging. 2007;26(1):15-30.
Stehning C, Börnert P, Nehrke K, Eggers H, Stuber M. Free-breathing whole-heart coronary MRA with 3D radial SSFP and self-navigated image reconstruction. Magnetic resonance in medicine. 2005;54(2):476-80.
Sussman MS, Stainsby JA, Robert N, Merchant N, Wright GA. Variable-density adaptive imaging for high-resolution coronary artery MRI. Magnetic Resonance in Medicine: An Official Journal of the International Society for Magnetic Resonance in Medicine. 2002;48(5):753-64.
Taylor AM, Jhooti P, Wiesmann F, Keegan J, Firmin DN, Pennell DJ. MR navigator-echo monitoring of temporal changes in diaphragm position: implications for MR coronary angiography. Journal of Magnetic Resonance Imaging. 1997;7(4):629-36.
Uribe S, Muthurangu V, Boubertakh R, Schaeffter T, Razavi R, Hill DL, et al. Whole-heart cine MRI using real-time respiratory self-gating. Magnetic Resonance in Medicine. 2007;57(3):606-13.
Usman M, Atkinson D, Odille F, Kolbitsch C, Vaillant G, Schaeffter T, et al. Motion corrected compressed sensing for free-breathing dynamic cardiac MRI. Magnetic resonance in medicine. 2013;70(2):504-16.
Walsh DO, Gmitro AF, Marcellin MW. Adaptive reconstruction of phased array MR imagery. Magnetic Resonance in Medicine. 2000;43(5):682-90.
Wehner GJ, Suever JD, Haggerty CM, Jing L, Powell DK, Hamlet SM, et al. Validation of in vivo 2D displacements from spiral cine DENSE at 3T. Journal of Cardiovascular Magnetic Resonance. 2015;17(1):5.
Winkelmann S, Schaeffter T, Koehler T, Eggers H, Doessel O. An optimal radial profile order based on the Golden Ratio for time-resolved MRI. IEEE transactions on medical imaging. 2007;26(1):68-76.
Young AA, Li B, Kirton RS, Cowan BR. Generalized spatiotemporal myocardial strain analysis for DENSE and SPAMM imaging. Magnetic resonance in medicine. 2012;67(6):1590-9.
Zhong X, Helm PA, Epstein FH. Balanced multipoint displacement encoding for DENSE MRI. Magnetic resonance in medicine. 2009;61(4):981-8.
Zhong X, Spottiswoode BS, Cowart EA, Gilson WD, Epstein FH. Selective suppression of artifact-generating echoes in cine DENSE using through-plane dephasing. Magnetic resonance in medicine. 2006;56(5):1126-31.
Zhong X, Spottiswoode BS, Meyer CH, Kramer CM, Epstein FH. Imaging three-dimensional myocardial mechanics using navigator-gated volumetric spiral cine DENSE MRI. Magnetic resonance in medicine 2010;64(4):1089-1097.

* cited by examiner

FREE-BREATHING CINE DENSE IMAGING

CROSS-REFERENCE TO RELATED APPLICATIONS

This application claims priority to U.S. Provisional Patent App. Ser. No. 62/649,289 filed on Mar. 28, 2018, and entitled "Free-Breathing Cine Dense Imaging", which is incorporated in its entirety as if set forth fully herein.

STATEMENT OF RIGHTS UNDER FEDERALLY-SPONSORED RESEARCH

This invention was made with government support under Grant No. HL135556, awarded by the National Institutes of Health. The government has certain rights in the invention.

BACKGROUND

Cine DENSE (displacement encoding with stimulated echoes) is a myocardial strain imaging technique that typically requires breath-holding during image acquisition. Subtraction of phase-cycled data can be utilized to suppress the artifact-generating T1-relaxation echo [1, 2]. With free-breathing, suppression of the T1-relaxation echo may not effective, however, due to respiratory motion between the phase-cycled data, resulting in artifacts.

Further described, cine DENSE [1] is a technique that is accurate [3], reproducible for both global and regional measurements [4], and amenable to rapid displacement and strain analysis [5]. With these properties, it can have many clinical applications. For example, Auger et al. [6] recently showed in heart failure patients that cine DENSE can quantify late mechanical activation and predict treatment response. Mangion et al [7] showed the prognostic value of cine DENSE in acute myocardial infarction, and Jing et al [8] showed the detection of subclinical contractile dysfunction in childhood obesity. Like many cardiac MRI acquisitions, cine DENSE is generally performed during breath-holding. However, in patient populations such as heart failure, acute myocardial infarction, children, and others, multiple breath-holds can be taxing. In addition, performing multi-breath-hold protocols can be complex for technologists.

While diaphragm-based navigator (dNAV) methods [9], including those for cine DENSE [2], are available, a paradigm shift is occurring in cardiac MRI where self-navigation with motion estimation and motion correction is superseding dNAV-based methods for free-breathing acquisitions. Self-navigated methods have the advantages that they do not require complex dNAV setup procedures and they can be more efficient than dNAVs because, with motion estimation and correction, they use data acquired during much or all of the respiratory cycle, whereas in dNAV-based methods data acquisition is restricted to a narrow band of the respiratory cycle. Self-navigated techniques have previously been developed for multiple cardiac MRI applications including cine imaging [10-12], late-gadolinium-enhanced imaging [13], coronary artery imaging [14-16], and T1 mapping [17], however they have not yet been developed for strain imaging methods such as cine DENSE. For cine DENSE imaging, two echoes are generally present in the acquisition window [1], namely the desired displacement-encoded stimulated echo and an echo due to T1 relaxation that can cause image artifacts. A two-point phase cycling method is typically used to suppress the T1-relaxation echo, wherein two acquisitions comprised of stimulated echoes of opposite signs and T1-relaxation echoes of the same sign are subtracted [1]. While phase cycling (used in conjunction with through-plane dephasing [18]) effectively suppresses the T1-relaxation echo for breath-hold DENSE protocols, this subtraction-based method can be ineffective for free-breathing scans because phase-cycled interleaves may be acquired at different respiratory positions where tissues contribute differently to the T1-relaxation signals. Insufficient suppression of the T1-relaxation echo leads to striping artifacts [18], which represents a unique and major challenge for free-breathing self-navigated cine DENSE. In addition to creating challenges for suppression of the T1-relaxation echo, respiratory motion induces blurring of the stimulated-echo image, as it does for other MR images.

It is with respect to these and other considerations that the various aspects of the disclosed technology as described below are presented. For example, Cine displacement encoding with stimulated echoes (DENSE) MM [1] is well-established and dedicated strain imaging technique. Recent studies demonstrated the potential of cine DENSE for detection of subclinical myocardium dysfunction and patient treatment stratification [2-4]. Cine DENSE acquisition is typically performed during breath-holding and multiple breath-holds are required per exam [1, 5]. However, such protocols can be challenging in patient populations such as heart failure, pediatrics, and others [5]). In practice, imperfect breath-holds lead to repetitions of acquisitions and reduce imaging efficiency. A reliable free-breathing method can overcome these challenges.

Among the various techniques for free-breathing cardiac MM, diaphragm-based navigator (dNAV) [6] was implemented for cine DENSE and was able to reduce breathing artifacts [7, 8]. However, the dNAV method requires extra scout scans and often results in variable imaging quality and efficiency [9-11]. A better solution for free-breathing cardiac MRI is self-navigation where the respiration information is extracted from the imaging data itself and used for motion compensation. Such methods have been developed for cardiac MRI applications such as SSFP cine imaging [12-15], angiography [16, 17], and T1 mapping [18].

In a previous study, a self-navigated reconstruction framework for free-breathing cine DENSE was developed [19]. The method addressed two major types of artifacts, namely the striping and blurring artifacts due to inter-heartbeat respiratory motion [19]. Cine DENSE imaging signal contains two echoes, the displacement-encoded stimulated echo and the artifact-generating T1-relaxation echo [1]. Typically, two phase-cycled datasets during different heartbeats are acquired and subtracted to suppress the T1-relaxation echo [20]. With free-breathing, the suppression is not effective with the subtraction, which leads to striping artifacts. Phantom and in vivo experiments demonstrated that the residual energy of the T1-relaxation echo (rT1E) after phase-cycling subtraction increased as the motion between the phase-cycled datasets increased. Minimal rT1E of the post-subtraction data identified phase-cycling pairs that were acquired at similar respiratory positions and reduced striping artifacts. After subtraction of the matched phase-cycling pairs, stimulated-echo only image-based navigators (ste-iNAVs) were reconstructed from the post-subtraction k-space data. In-plane motion due to respiration was then estimated with the ste-iNAVs and corrected to reduce blurring.

However, this reconstruction framework still had a few drawbacks. The image quality was not guaranteed and the imaging efficiency was not optimized. The reconstruction was performed retrospectively after the data acquisition was completed with a prescribed protocol and fixed acquisition order. DENSE data were acquired with three repetitions to provide multiple candidates of phase-cycling pairs and a better chance of suppressing the T1-relaxation echo sufficiently rather than acquiring each phase-cycling just once. Yet, such a protocol cannot guarantee high-quality free-breathing cine DENSE as the number of repetitions necessary may vary from subject to subject. Increasing the repetition number increases the possibility of matching phase-cycling data for every k-space segment but reduces imaging efficiency. Using real-time feedback on rT1E to guide data acquisition can potentially guarantee sufficient suppression of the T1-relaxation echo without sacrificing the imaging efficiency.

In addition to blurring, respiratory motion within each heartbeat (intra-heartbeat motion) can induce phase errors in the stimulated-echoes. In cine DENSE, tissue motion is encoded into the phase of the stimulated-echoes. The motion-related phase is linear with the displacement of the tissue that happens between application of the preparation pulses and the k-space data acquisition. Along with the myocardial displacement with the heart contracting and relaxing periodically, the bulk movement of the heart due to respiration is also encoded into the stimulated-echo signal. The intra-heartbeat motion induced phase is likely to be greater during diastole than during systole because diastole is later from the application of preparation pulses. This phase is also likely to be different during different heartbeats. Such variations of intra-heartbeat motion and phase errors can cause signal cancellation artifacts and significantly degrade image quality. These signal cancellation artifacts are similar to those reported in diffusion weighted imaging (DWI) [21, 22] and MR elastography [23] and should be properly compensated.

SUMMARY

In some aspects, the disclosed technology relates to free-breathing cine DENSE (displacement encoding with stimulated echoes) imaging. In some embodiments, self-gated free-breathing adaptive acquisition reduces free-breathing artifacts by minimizing the residual energy of the phase-cycled T1-relaxation signal, and the acquisition of the k-space data is adaptively repeated with the highest residual T1-echo energy. In some embodiments, phase-cycled spiral interleaves are identified at matched respiratory phases by minimizing the residual signal due to T1 relaxation after phase-cycling subtraction; image-based navigators (iNAVs) are reconstructed from matched phase-cycled interleaves that are comprised of the stimulated echo iNAVs (ste-iNAVs), wherein the ste-iNAVs are used for motion estimation and compensation of k-space data.

In one aspect, the present disclosure relates to a method of acquiring magnetic resonance imaging data for a plurality of images of a subject, wherein the plurality of images comprises respectively phase-cycled interleaves of the imaging data that populate a respective segment of the images and calculating residual T1 energy values for each of the images. In one embodiment, the method includes selecting a first image and a second image as a first matched pair of images, wherein the first matched pair of images has a lowest average of corresponding residual T1 energy values in comparison to other unselected pairs of the images. In accordance with the method, this disclosure includes subtracting the first image from the second image to suppress artifacts within a resulting image and using the resulting image to reconstruct an image-based navigator (iNav) for the segment, wherein the iNav includes stimulated-echo images with suppressed artifacts (ste-iNAVs).

In another aspect, in accordance with one embodiment of the present disclosure, a method includes sampling segments of image data acquired during magnetic resonance imaging, wherein the segments include frames of images. Each frame includes respective phase-cycled interleaves of the imaging data acquired during a respective phase of an encoding signal. Sampling includes calculating residual T1 energy values for each of the images and selecting a first image and a second image as a first matched pair of images. The first matched pair of images has a lowest average of corresponding residual T1 energy values in comparison to other unselected pairs of the images. Subtracting the first image from the second image suppresses artifacts within a resulting image. All of the segments are iteratively evaluated by selecting a target segment having a highest residual T1 energy value in comparison to unselected segments. The method includes repeating the magnetic resonance imaging for the target segment and acquiring new image data for the target segment. By sampling the new image data and calculating a new residual T1 energy value for the target segment, the method of this embodiment repeats the selecting of a target segment until satisfying at least one of a set of stopping criteria. The method reconstructs an image-based navigator (iNav) for the respective segments using a last resulting image for each segment, wherein the iNav includes stimulated-echo images with suppressed artifacts (ste-iNAVs).

In yet another aspect, according to one aspect of the present disclosure, a method includes acquiring magnetic resonance imaging data, for a plurality of images of a subject, wherein the plurality of images comprises respectively phase-cycled interleaves of the imaging data that populate a respective segment of the images and calculating residual T1 energy values for each of the images. Iteratively matching pairs of the images within respective segments of images provides a lowest yielded average of pairs of respective residual T1 energy values for subtracting iteratively matched images to suppress artifacts. The method includes reconstructing respective ste-iNavs within the respective segment for the iteratively matched images and comparing the reconstructed iNavs in at least one k space representation of each respective segment to identify 2D translation motion and translation motion correction values for the segments. This embodiment corrects phase error for the translation motion in the k space representation by selecting for each coding dimension a reference segment from the respective segments of the image data and using the reference segment to correct other segments. Correcting other segments includes for each other segment, maximizing an energy function ($E(\theta)$) for a complex sum of the reference segment (Sref) and each of said other segments (Scor) such that $E(\theta)=|Sref+Scor\,e(-i\theta)|2$, wherein a correction value $\theta$ that maximizes the energy function is a correction value for a respective other segment (Scor).

In yet another aspect, the present disclosure relates to a system which, in one embodiment, includes at least one processor, at least one memory device coupled to the processor and storing computer-readable instructions which, when executed by the at least one processor, cause the system to perform functions of a method. A method of acquiring magnetic resonance imaging data for a plurality of images of a subject, wherein the plurality of images comprises respectively phase-cycled interleaves of the imaging data that populate a respective segment of the images and calculating residual T1 energy values for each of the images.

The method includes selecting a first image and a second image as a first matched pair of images, wherein the first matched pair of images has a lowest average of corresponding residual T1 energy values in comparison to other unselected pairs of the images. In accordance with the method, this disclosure includes subtracting the first image from the second image to suppress artifacts within a resulting image and using the resulting image to reconstruct an image-based navigator (iNav) for the segment, wherein the iNav includes stimulated-echo images with suppressed artifacts (ste-iNAVs).

Other aspects and features according to the example embodiments of the disclosed technology will become apparent to those of ordinary skill in the art, upon reviewing the following detailed description in conjunction with the accompanying figures.

BRIEF DESCRIPTION OF THE DRAWINGS

The patent or application file contains at least one drawing executed in color. Copies of this patent or patent application publication with the color drawing(s) will be provided by the Office upon request and payment of the necessary fee. Reference will now be made to the accompanying drawings, which are not necessarily drawn to scale.

DETAILED DESCRIPTION

Figure 1:
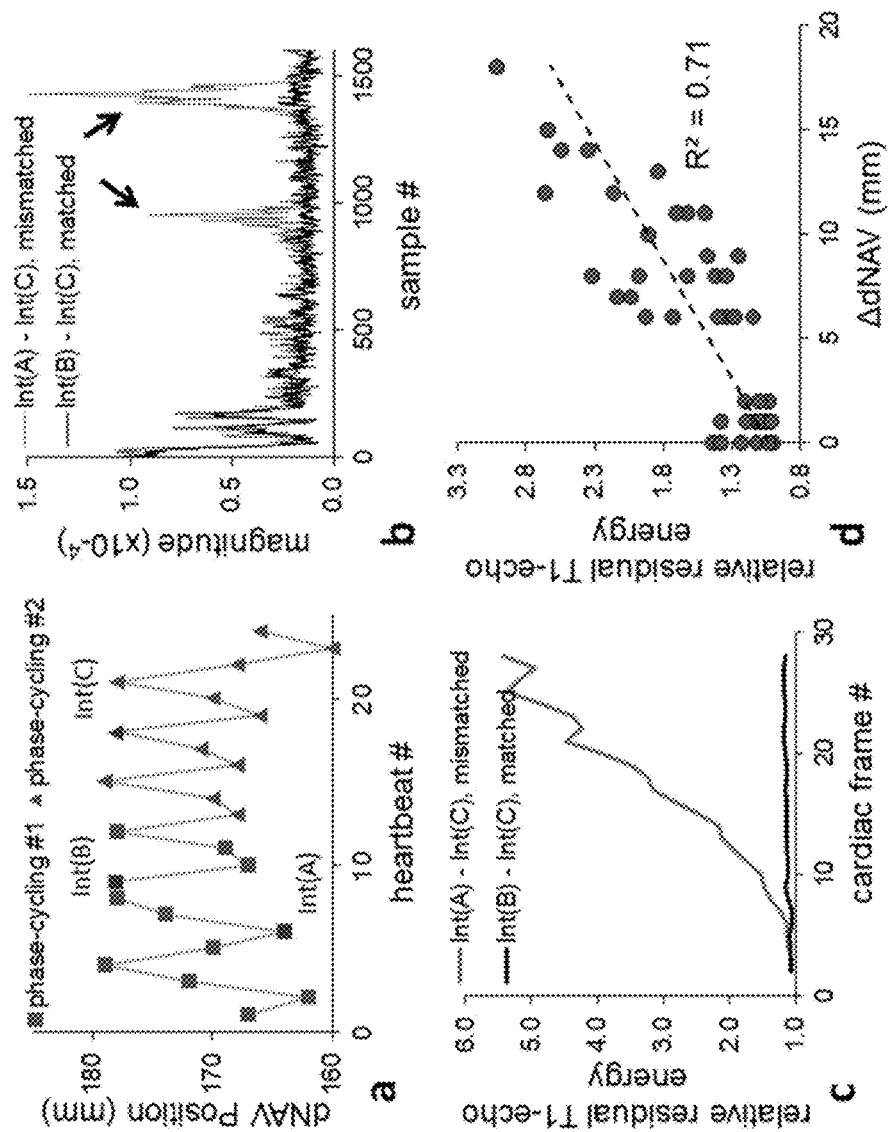
FIG. 1 shows phase-cycled cine DENSE data acquired during free breathing were processed to show that the relative residual T1-relaxation echo energy from phase-cycled interleave pairs correlates with the difference in the diaphragm positions of the interleave pairs for in vivo imaging. (a) dNAV-based monitoring of respiration is shown, along with the annotated acquisitions of phase-cycled interleaves. (b) Magnitudes of post-subtraction interleaves for interleave pairs at similar (Int(B)-Int(C)) and different (Int(A)-Int(C)) respiratory positions. (c) The relative residual T1-relaxation echo energies of the two phase-cycling pairs at each cardiac frame. (d) The relative residual T1-relaxation-echo energy summed over all cardiac frames is highly correlated to the difference in the diaphragm positions, with $R^2$=0.71.

In some aspects, the disclosed technology relates to free-breathing cine DENSE (displacement encoding with stimulated echoes) imaging. Although example embodiments of the disclosed technology are explained in detail herein, it is to be understood that other embodiments are contemplated. Accordingly, it is not intended that the disclosed technology be limited in its scope to the details of construction, and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology.

Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific organs, tissues, or fluids of a subject, may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the disclosed technology and is not an admission that any such reference is "prior art" to any aspects of the disclosed technology described herein. In terms of notation, "[n]" corresponds to the $n^{th}$ reference in the list. For example, [3] refers to the $3^{rd}$ reference in the list, namely Young, et al. All references cited and discussed in this specification are incorporated herein by reference in their entireties and to the same extent as if each reference was individually incorporated by reference.

A detailed description of aspects of the disclosed technology, in accordance with various example embodiments, will now be provided with reference to the accompanying drawings. The drawings form a part hereof and show, by way of illustration, specific embodiments and examples. In referring to the drawings, like numerals represent like elements throughout the several figures. The following description includes discussion of some example implementations and corresponding results. Some experimental data are presented herein for purposes of illustration and should not be construed as limiting the scope of the disclosed technology in any way or excluding any alternative or additional embodiments.

Self-Gated Free-Breathing Cine DENSE Imaging by Adaptively Reducing Residual T1-Echo Energy In some aspects discussed in further detail below with respect to certain embodiments, the present disclosure relates to self-gated free-breathing cine DENSE imaging by adaptively reducing residual T1-echo energy. In some embodiments, self-gated free-breathing adaptive acquisition reduces free-breathing artifacts by minimizing the residual energy of the phase-cycled T1-relaxation signal, and the acquisition of the k-space data is adaptively repeated with the highest residual T1-echo energy.

Methods

The DENSE signal includes a stimulated echo and a T1-relaxation echo, with echo centers occurring at different locations in k-space [1]. FIG. 1a shows dNAV-based monitoring of respiration along with the annotated acquisitions of phase-cycled interleaves. FIG. 1b shows example k-space data subsequent to subtraction of phase-cycled data along a spiral trajectory. When phase-cycled data are acquired at the same position, suppression of the T1-relaxation echo is effective (black curve). However, strong residual T1-relaxation signal remains when the data are acquired at different positions (grey curve). Residual energy of the T1-echo (rT1E) can be quantified by summing the energy over a predefined k-space range (gray area). The rT1E of free breathing (FB) is substantially higher than that of breath-hold (BH), especially during diastole (FIG. 1c). Further, the rT1E correlates with differences in respiratory position (FIG. 1d). It was hypothesized that FB artifacts can be minimized by reducing the rT1E.

Figure 2:
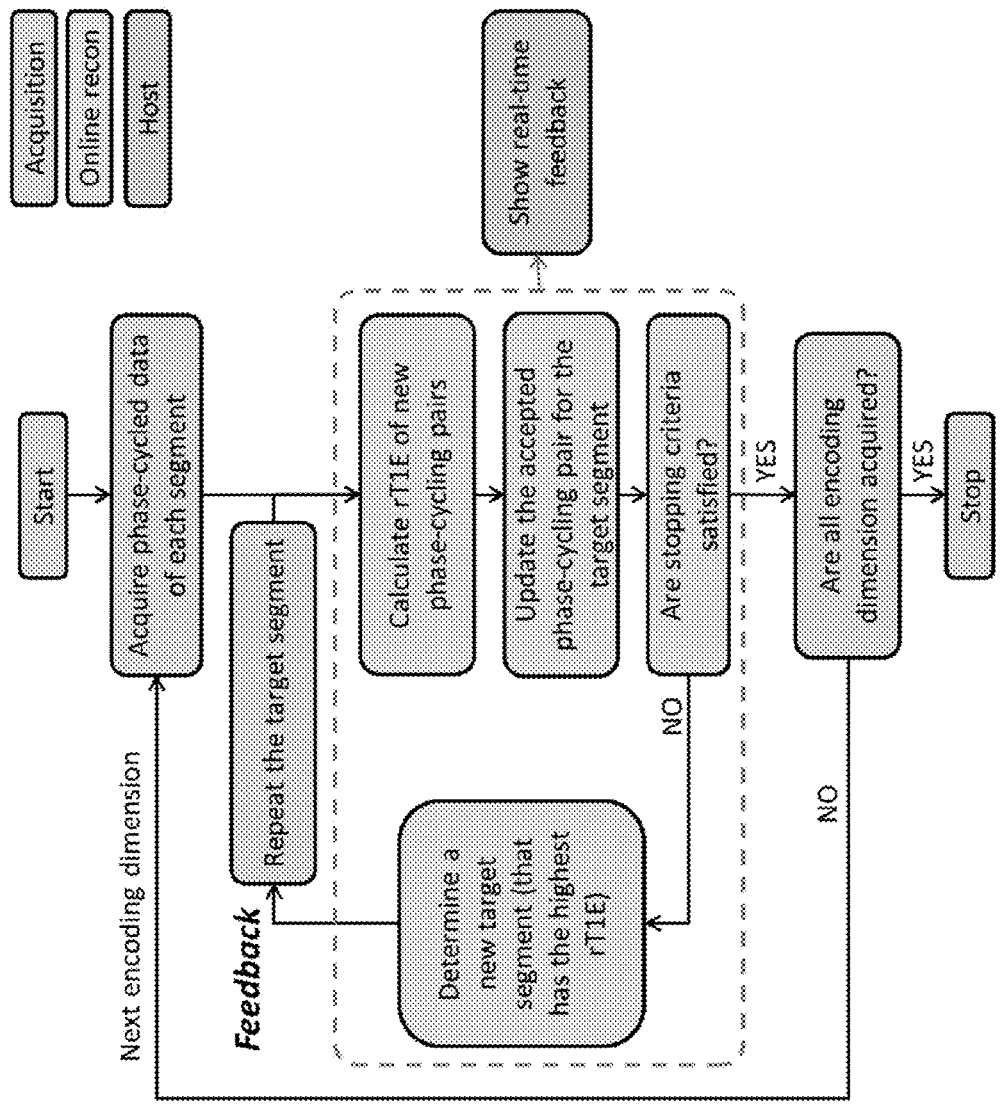
FIG. 2 shows a diagram of a self-gated adaptive free-breathing cine DENSE imaging method.

An adaptive acquisition algorithm was implemented using a 2D spiral cine DENSE sequence with a segmented spiral trajectory and localized stimulated echoes [19]. As in FIG. 2, the acquisition starts by acquiring a complete set of k-space data. The online reconstruction environment (ICE) calculates rT1E of each phase-cycling pair and determines whether the stopping criteria are satisfied. If so, the acquisition stops and moves to the next displacement-encoding dimension. If not, ICE determines the segment that currently has the highest rT1E (target segment). Real-time feedback is delivered to the sequence, which then repeats the target segment. When new data are acquired, they are compared to all previously acquired data of the same segment to find the best matched phase-cycling pair. Presently, the stopping criterion is an imaging time of 30 heartbeats.

Seven healthy subjects were scanned on a 3T system (Prisma, Siemens) with a 6-channel body coil and a 32-channel spine coil. FB datasets were acquired for mid-ventricular short-axis slices using: 6 interleaves per image, 2 interleaves per segment, spatial resolution of 3×3 mm$^2$, TR=15 ms, TE=1.08 ms, uniform rotation of the spiral trajectory through frames, simple 3-point displacement encoding, and displacement-encoding frequency of 0.10 cyc/mm.

Figure 3:
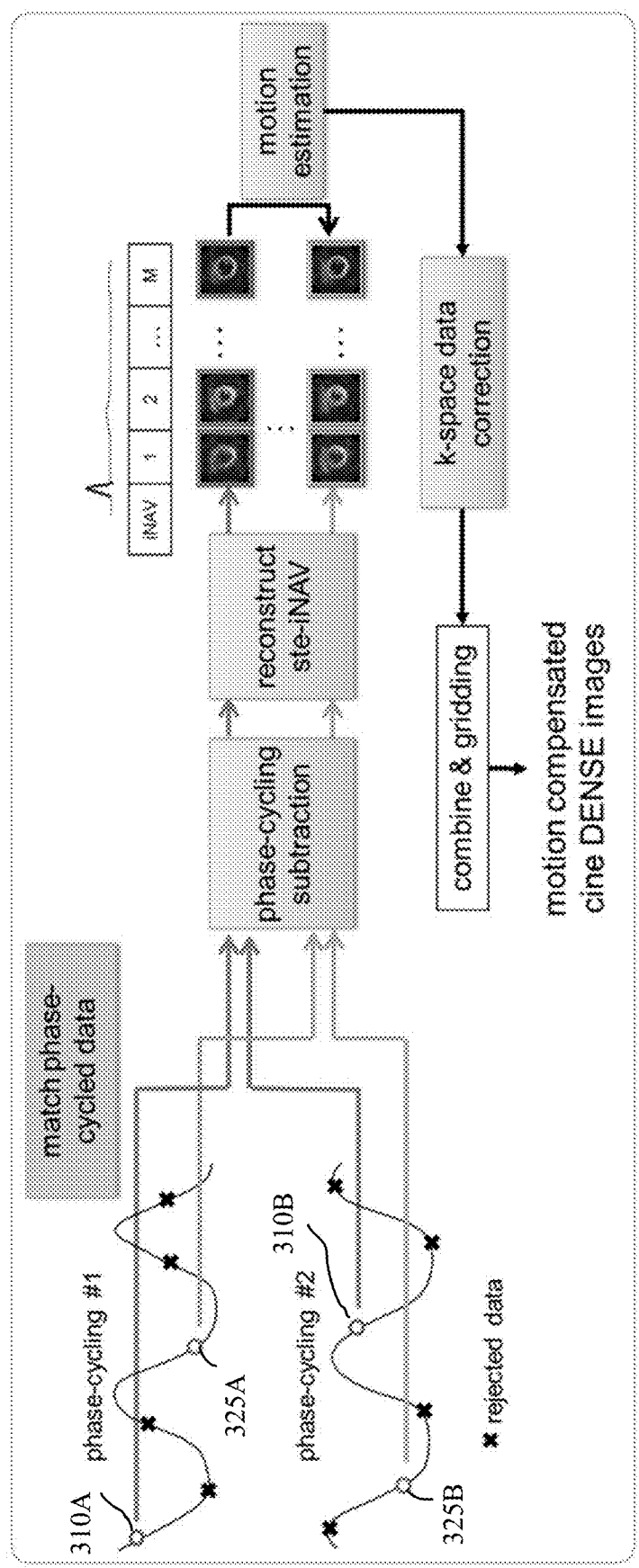
FIG. 3 shows a diagram of a match-making framework for free-breathing cine DENSE imaging. First, match-making is applied to identify phase-cycled interleave pairs acquired at matched respiratory positions to compensate for striping artifacts. The two blue circles identify a matched phase-cycling pair and the two green circles identify another matched pair. Phase-cycling subtraction is performed using the identified phase-cycled interleaves and ste-iNAVs are reconstructed from post-subtraction data. Lastly, ste-iNAV based, in-plane motion estimation and correction is performed to compensate for blurring artifacts.

Each dataset was analyzed offline in MATLAB (Mathworks, USA), mimicking the online algorithm. Cine DENSE images were reconstructed from the identified phase-cycling pairs with minimized rT1E and subsequent motion correction, as shown in FIG. 3. The quality of each reconstruction was evaluated using the signal-to-noise ratio (SNR) of magnitude images [20].

Results

Figure 4:
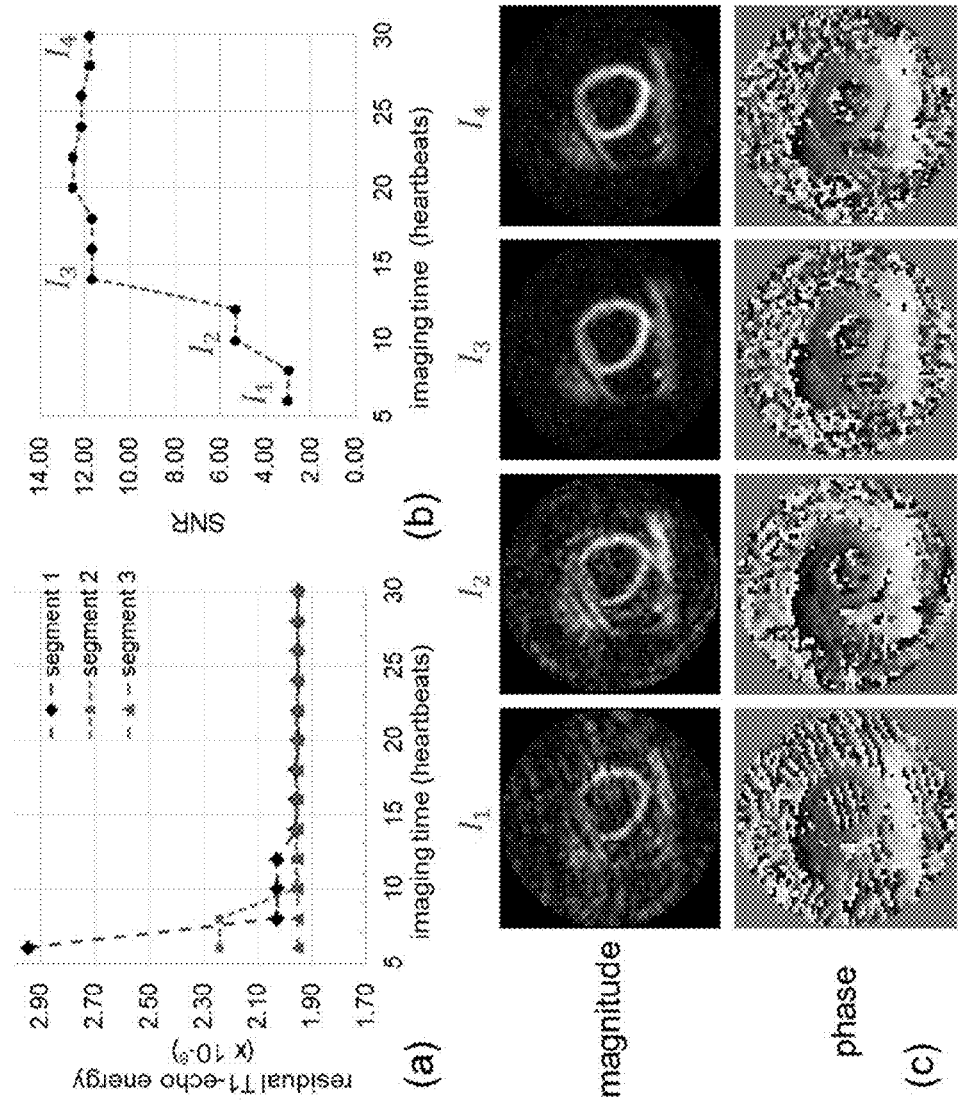
FIG. 4 shows example results from an adaptive FB cine DENSE dataset from a healthy subject. (a) Residual T1-echo energy of each k-space segment decreased as the imaging progressed. (b) The corresponding SNR of DENSE images increased. (c) Diastolic images at four different time points during the scan (as indicated in panel (b)) demonstrate improving image quality during the adaptive acquisition. Both the magnitude (top row) and the phase (bottom row) images are shown.

FIG. 4 shows results from one volunteer demonstrating the method. The overall k-space rT1E from the best matched phase-cycling pairs decreased as the adaptive acquisition progressed and reached a low level after 15 heartbeats (a). At each time, the segment with the highest rT1E was repeated and its rT1E was reduced after the acquisition of new data. Correspondingly, the SNR of the DENSE magnitude images increased (b). Panel (c) shows images of a late diastolic frame from 4 different time points during the acquisition (I1-I4). Strong artifacts are present in I1-I2 but not in I3-I4.

Figure 5:
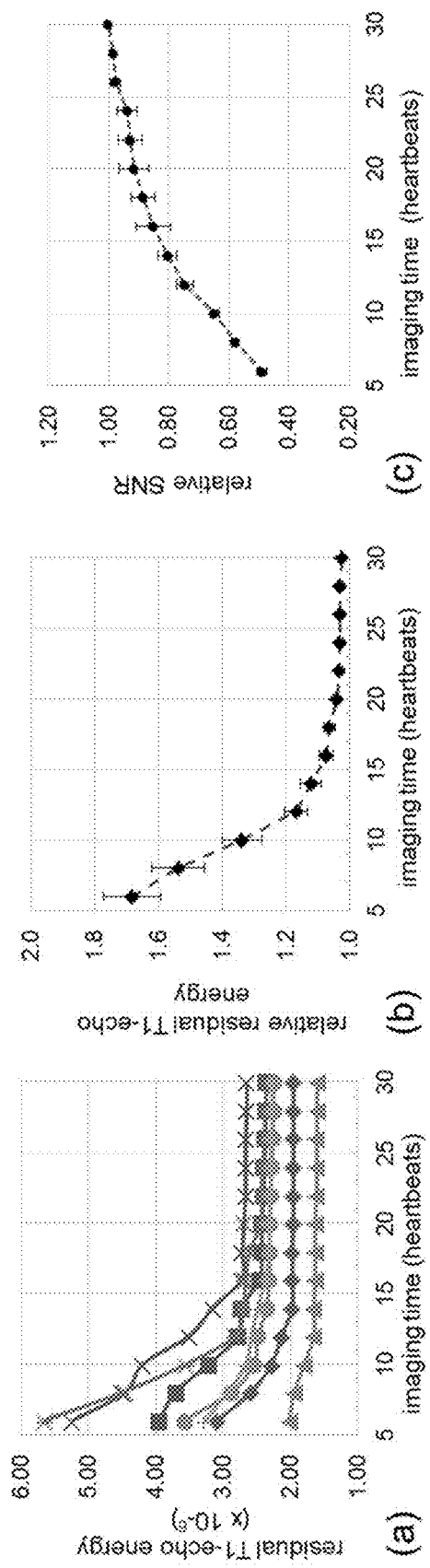
FIG. 5 shows a summary of results from all subjects. (a) The residual T1-echo energy of all subjects during the acquisition. (b) Residual T1-echo energy normalized to that of the early systolic frames estimated at the corresponding imaging time points. (c) SNR relative to that at end of the acquisitions.

FIG. 5 summarizes the results from all subjects. The rT1E converged similarly for all subjects, although to a different value due to intrinsic k-space energy variations between subjects (a). These variations were accounted for by normalizing the rT1E to that of early systolic frames, which can be estimated at each time. The normalized rT1E converged to a similar value (1.027±0.007, mean±standard error, at an imaging time of 30 heartbeats) (b). Compared to the initial value, the relative rT1E decreased by 70% after 20-heartbeats. The relative SNR (normalized to the final reconstructed image) doubled (c).

Discussion

The algorithm for self-gated FB cine DENSE imaging described above minimizes rT1E, which is a surrogate for motion between phase-cycled data to reduce artifacts. In vivo experiments demonstrated that image quality increased as rT1E decreased during the adaptive acquisition. For the specific protocol used, the time to converge to high-quality images was 20-25 heartbeats per displacement-encoding dimension. The normalized rT1E may be a stopping criterion to provide high image quality and shorter scan times.

Free-Breathing Cine DENSE MM Using Phase Cycling with Matchmaking and Stimulated-Echo Image-Based Navigators In some aspects discussed in further detail below with respect to certain embodiments, the present disclosure relates to free-breathing cine DENSE MM using phase cycling with matchmaking and stimulated-echo image-based navigators. In some embodiments, phase-cycled spiral interleaves are identified at matched respiratory phases by minimizing the residual signal due to T1 relaxation after phase-cycling subtraction. Image-based navigators (iNAVs) are reconstructed from matched phase-cycled interleaves that are comprised of the stimulated echo iNAVs (ste-iNAVs), wherein the ste-iNAVs are used for motion estimation and compensation of k-space data. Embodiments discussed with respect to these aspects address two consequences of motion for DENSE: striping artifacts from incomplete suppression of the T1-relaxation echo, and blurring.

Figure 6:
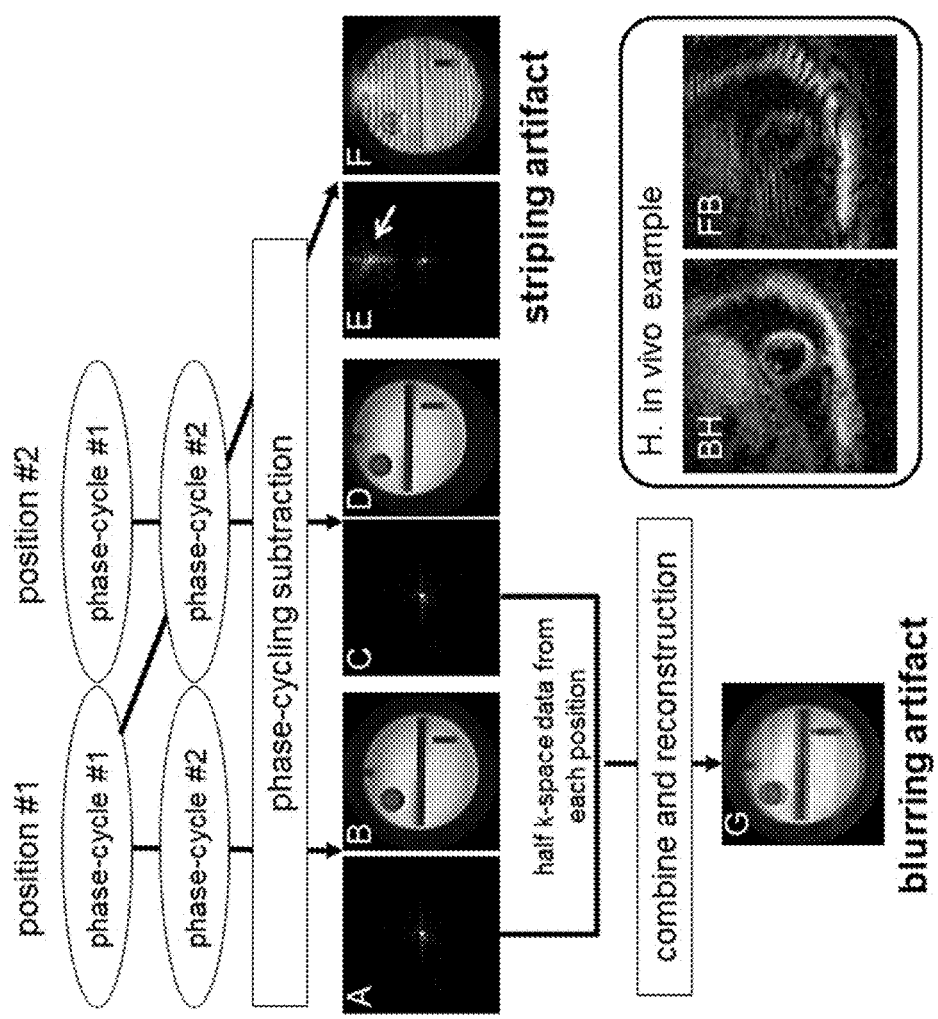
FIG. 6 shows an illustration of motion-induced striping and blurring artifacts in cine DENSE imaging. In this experiment, fully-sampled cine DENSE images were acquired with the phantom located at position 1 and also at position 2. Motion, simulated by combining phase-cycling pairs from positions 1 and 2, induces insufficient suppression of the T1-relaxation echo (panel e, white arrow) and corresponding striping artifacts in the images (panel f). If phase-cycled data at matched positions are subtracted (panels a, c), but motion occurs between k-space segments after successful suppression of the T1-relaxation echo (panel b, d), then blurring artifact occurs when combining data from different segments (panel g). In this example, half of the k-space data was taken from each of the two positions. In vivo example images demonstrating both blurring and striping artifacts due to respiratory motion are also shown. (Panel h, BH: breath-holding; FB: free-breathing.)

In FIG. 6, both types of motion-related artifacts are demonstrated using spiral cine DENSE data acquired from a phantom placed at two different positions. As shown, subtraction of phase-cycled data acquired at mismatched positions leads to a strong residual T1-relaxation echo in k-space (FIG. 6e) and striping artifacts in the corresponding image (FIG. 6f). After subtraction of phase-cycled data from matched positions, image reconstruction that combines post-subtraction stimulated echoes from different positions leads to blurring (FIG. 6g). These types of artifacts are observed for free-breathing in vivo cine DENSE, as shown in FIG. 6h, and can lead to unsuccessful imaging of patients with imperfect breath-holding, as previously reported [21, 22]. In accordance with various embodiments described herein, a method for free-breathing self-navigated cine DENSE is disclosed, which involves suppression of the T1-relaxation echo as a first step, followed by the use of image-based navigators (iNAVs) for motion estimation and correction as a second step.

Free-Breathing Cine DENSE Framework Using Match-Making and Stimulated-Echo Image-Based Navigators (Ste-iNAVs)

Methods

Figure 7:
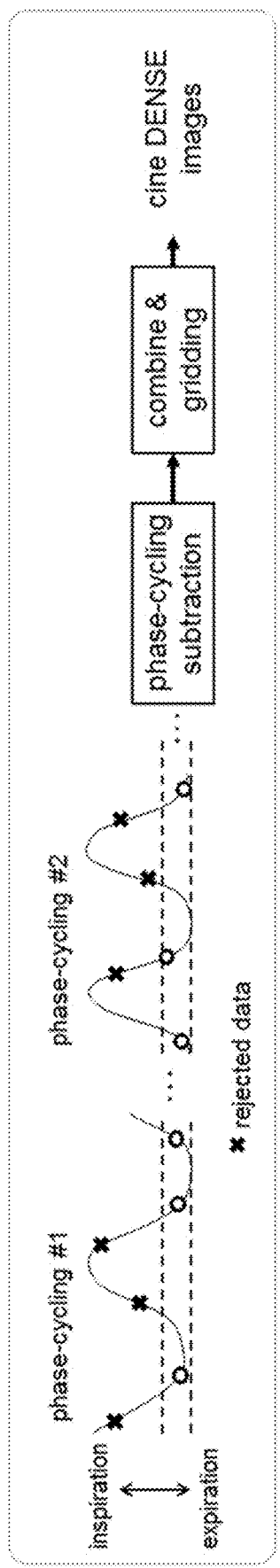
FIG. 7 shows a diagram of the conventional respiratory gating strategy using dNAVs or conventional iNAVs (c-iNAVs), where data within a narrow window around end-expiration are accepted.

The self-navigated framework for free-breathing spiral cine DENSE disclosed herein (a) selects phase-cycled spiral interleaves at matched respiratory phases, (b) performs subtraction of matched phase-cycled interleaves, (c) reconstructs image-based navigators (iNAVs) from post-subtraction interleaves (ps-interleaves) that are primarily comprised of the stimulated echo (termed ste-iNAVs), (d) performs ste-iNAV-based motion estimation to account for motion between ps-interleaves, and (e) applies rigid motion correction in k-space for image reconstruction. The first part of this method, which selects phase-cycled interleaves at matched respiratory phases, is termed "match-making". The proposed framework is illustrated in FIG. 3 and is shown in contrast to conventional respiratory-gated navigator strategies such as dNAVs or conventional iNAVs (c-iNAVs) (FIG. 7).

Match-making of phase-cycled interleaves acquired during free breathing is performed by evaluating the residual energy of the T1-relaxation echo after complex subtraction of those phase-cycled interleaves. This approach is based on the concept that the residual T1-relaxation echo energy will be minimized when the phase-cycled interleaves are acquired at matched respiratory phases, and will be greater otherwise. Since the approximate location in k-space of the T1-relaxation echo is determined by the displacement-encoding frequency, ke, the residual T1-relaxation echo energy can be estimated by summing data over a predetermined region of k2space, i.e., k>ke/2. Localized generation of stimulated echoes can be used along with matchmaking to suppress the T1-relaxation echo, so that ste-iNAVs can be focused to the heart, a reduced field of view (FOV) can be used, and automated motion estimation is facilitated.

DENSE Pulse Sequence

Figure 8:
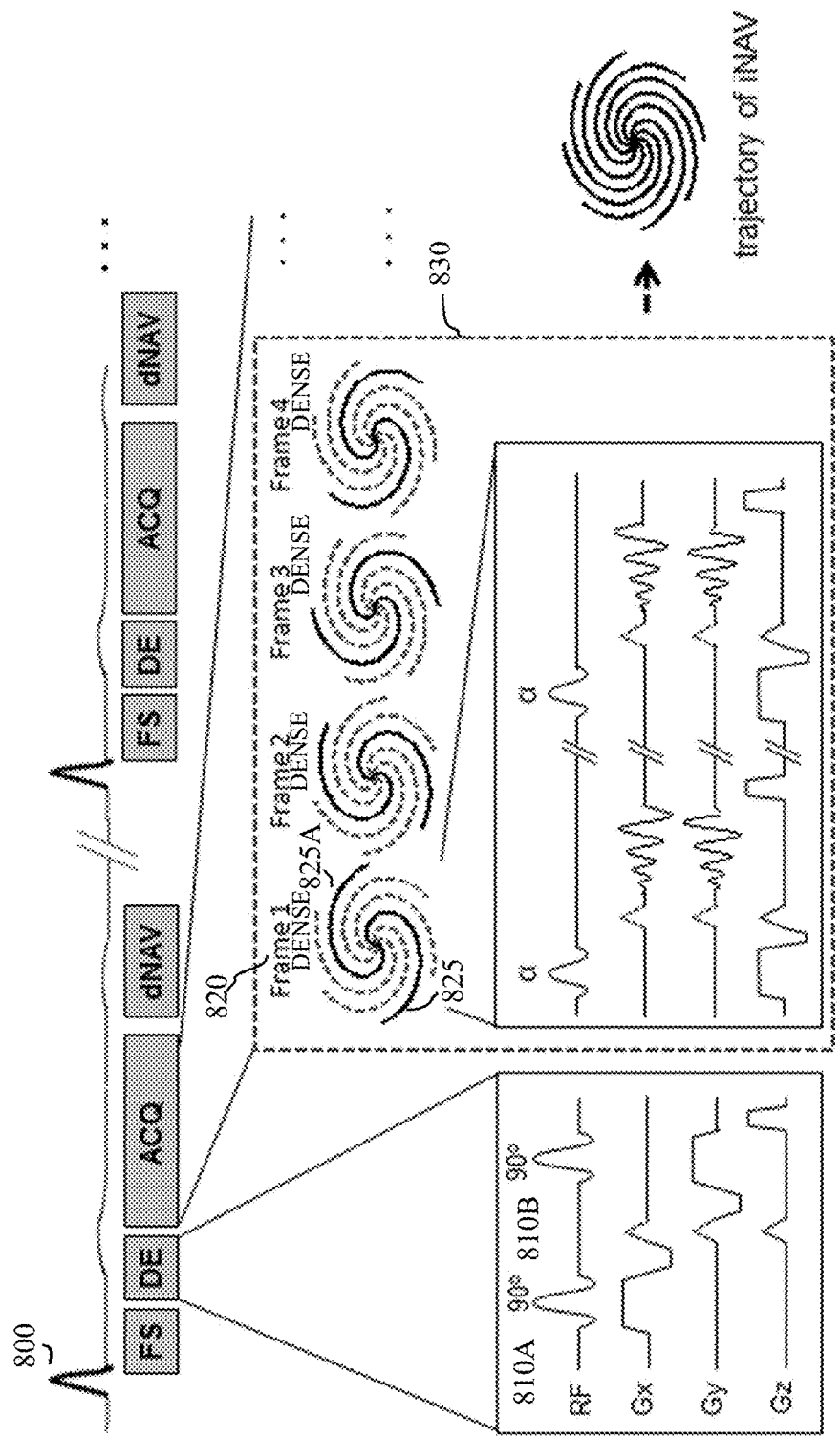
FIG. 8 shows a diagram of the pulse sequence used for free-breathing cine DENSE. Fat saturation (FS) is applied after each ECG trigger (800), followed by displacement encoding (DE) pulses (810A, 810B), spiral acquisitions (ACQ) are set forth in FIG. 8 as respective frames or images (820) that each have phase cycled interleaves (825A, 825B). A series of frames or images (820) collectively form a segment (830) of image data between heart beats shown as the ECG triggers (800). The series of images or frames (820) and the diaphragm navigator (dNAV). Localized generation of stimulated echoes is performed by applying slice selection for all RF pulses, including those in the displacement encoding module. Data acquisition uses a segmented spiral trajectory with golden angle rotation of the trajectory through cardiac frames. Each iNAV frame consists of four cine DENSE frames (i.e., eight consecutive spiral interleaves).

To experimentally investigate free-breathing cine DENSE imaging using the matchmaking framework with motion compensation, a previously-described spiral cine DENSE pulse sequence [2], was modified. The previously-described spiral cine DENSE pulse sequence supports two-point phase-cycling, to include golden angle rotation [23, 24] through time frames within the cardiac cycle and localized generation of stimulated echoes, as shown in FIG. 8. Golden angle (a) rotation facilitates the reconstruction of iNAVs by utilizing consecutively acquired interleaves. In the current 5 design, each fully sampled iNAV frame consisted of eight consecutively acquired interleaves, i.e. four consecutive frames with golden angle rotation between them and two interleaves per frame with uniform rotation. Localized generation of stimulated echoes was implemented by applying slice selection for all RF pulses that contribute to the stimulated echo such that stimulated echoes were generated only in the region where the RF pulse profiles intersect [19, 25]. It is noted that, with this pulse sequence, while the stimulated echo is localized to the heart region, the T1-relaxtion echo originates from the entire slice. The cine DENSE pulse sequence also supported acquisition of a dNAV at end-diastole, as previously described [2]. All DENSE scans employed multi-coil acquisitions, and multi-channel data were adaptively combined to reconstruct complex images with sensitivity maps estimated 15 from the data itself, as previously described [26].

Reconstruction Using the Match-Making Framework

As illustrated in FIG. 3, phase-cycled spiral interleaves at matched respiratory phases were selected using the match-maker criterion, specifically the minimal residual T1-relaxation echo energy. In some embodiments, matched interleaves have the same displacement encoding and k-space trajectory, and they can be selected from any respiratory phase, without limitation. The residual T1-relaxation echo energy was averaged over all cardiac frames within each heartbeat. It was assumed that multiple averages of all interleaves are acquired. Of the available pairs of interleaves to choose from, the one pair (one average) with the lowest residual T1-echo energy (the match) was selected for the reconstruction. After match-making, subtraction of matched interleaves was performed and ste-iNAVs were reconstructed. Multiple ste-iNAVs were reconstructed per heartbeat, specifically one ste-iNAV was reconstructed using eight spiral interleaves, and a sliding window was not used. Two-dimensional translations were estimated using the ste-iNAVs automatically, without manual identification of a region, using two dimensional cross-correlation. Motion estimation was performed separately for different cardiac phases. The resulting motion estimation was used for motion compensation of the selected segmented k-space data [9]. The resulting motion-corrected k-space data underwent density weighted nonuniform fast Fourier transform [27] to reconstruct final cine DENSE images.

Reconstruction Using Conventional dNAV Gating

As illustrated in FIG. 7, the conventional dNAV reconstruction method accepted data acquired within a dNAV window centered at end-expiration, and rejected data outside that window. In the protocol described herein, the inventors acquired a fixed number of averages, and in a retrospective reconstruction accepted one average of data that were within the narrowest window at end-expiration based on the dNAV position. This method was chosen to facilitate a fair comparison between the various reconstructions.

Reconstruction Using Conventional iNAV Gating

For the c-iNAV reconstruction, c-iNAVs were reconstructed using the methods described in the section below, titled "Principle component analysis (PCA) to separate signals for improved conventional cine DENSE iNAVs." Since c-iNAVs were reconstructed for each individual heartbeat, their reconstruction did not employ subtraction of phase-cycled interleaves. Instead, suppression of the T1-relaxation echo for the c-iNAVs was performed by separating the stimulated echo and T1-relaxation echoes using principle component analysis (PCA), and applying a PCA filter to the iNAVs (See, for example, FIGS. 15 and 16). An early systolic c-iNAV was used and 2D translation was estimated by 2D cross-correlation for displacement-based retrospective gating. Similar to dNAV-gating, one average of data within a narrow window around end expiration defined by the c-iNAV position were accepted, as described in FIG. 7.

Experimental Design

Phantom experiments were conducted to demonstrate the use of matching phase-cycled interleaves using the residual T1-echo energy and using localized ste-iNAVs for motion estimation and correction. All phantom imaging was performed on a 3T MRI system (Magnetom Prisma, Siemens Healthcare, Erlangen, Germany) with a 32-channel phased-array spine coil.

Specifically, a phantom was scanned and cine DENSE datasets were acquired six times. Between each acquisition the phantom was moved toward the head direction in 5 mm increments to create a range of translations. For each phantom position, a coronal slice, a transverse slice and an oblique slice between the coronal and transverse planes were scanned. The motions seen by these three slices were in-plane translation, through-plane motion and a combination of in-plane and through-plane motion, respectively. Cine DENSE datasets were acquired with the following parameters: FOV=260×260 $mm^2$, 10 spiral interleaves, spiral readout length of 2.8 ms, in-plane spatial resolution of 3.4×3.4 $mm^2$, 2 spiral interleaves per heartbeat, TR=15 ms, TE=1.08 ms, and slice thickness=8 mm. The displacement encoding frequency was 0.10 cycles/mm, and the through-plane dephasing frequency was 0.04 cycles/mm. The T1 of the phantom was approximately 150 ms. DENSE imaging was performed with a simulated RR interval of 1000 ms. Ten frames were imaged for the phantom experiment. The trigger time of the images used for data analysis was 150 ms. For analysis, we correlated the residual T1-echo energy with the amount of phantom motion and we demonstrated the ability to perform motion estimation and compensation using ste-iNAVs.

In addition, free-breathing cine DENSE datasets were acquired from 12 healthy volunteers (7 male, 27.3±2.1 years old) who were scanned in accordance with protocols approved by our institutional review board after providing informed consent. All volunteer imaging was performed on 3T systems (Magnetom Trio and Magnetom Prisma; Siemens Healthcare, Erlangen, Germany) with a phased-array body coil (6-channel for Magnetom Trio and 18-channel for Magnetom Prisma) and a 32-channel spine coil. After the acquisition of localizer images, a mid-ventricular short-axis slice was acquired during both breath-holding and free-breathing acquisitions with the following parameters: FOV=160×160 $mm^2$, thickness of localized stimulated echo=80-100 $mm^2$, 6 spiral interleaves per image, 2 interleaves per heartbeat, spiral readout length of 3.4 ms, in-plane spatial resolution of 3×3 $mm^2$, slice thickness=8 mm, TR=15 ms, TE=1.08 ms, and temporal resolution of 30 ms. Ramped flip angles with a final flip angle of 15° were employed to achieve a consistent signal-to-noise ratio (SNR) through the cardiac cycle [27]. Fat suppression was employed by applying a fat saturation pulse immediately after ECG triggering as previously described [2, 29]. Depending on the heart rate of the subject, 22-30 frames were acquired, covering approximately 80% of the RR interval. The rest of the RR interval was used to acquire the dNAV and allow for variation in the RR interval. The total scan time was 18 heartbeats (corresponding to one average) for breath-hold acquisitions and 54 heartbeats (corresponding to the acquisition of each interleave three times, and implemented using the averaging loop) for free-breathing acquisitions. The DENSE loop structure, from inner to outer, looped through spiral interleaves, averages, phase-cycling pairs, and displacement-encoding dimensions, which included reference, x-encoded and y-encoded acquisitions [30]. The temporal and spatial resolutions were chosen based on protocols that have been reported in clinical studies to provide a balance of SNR, temporal resolution, and total scan time [31]. Additionally, for 5 subjects, a 15-average dataset (270 heartbeats in duration) was acquired and these data were used to demonstrate the relationships between ste-iNAV and c-iNAV motion estimation and dNAV data. All 3-average datasets were reconstructed offline three ways in MATLAB (Mathworks, Natick, Mass.) using: (a) the conventional dNAV method, (b) the c-iNAV method and (c) the match-making framework.

Evaluation of the Match-Making Framework

The volunteer data were used to evaluate intermediate steps of the match-making framework as applied to in vivo imaging. Specifically, the inventors computed the correlation between the residual T1-echo energy and the difference in the dNAV positions for all phase-cycling interleave pairs from free-breathing acquisitions. These data could demonstrate that low residual T1-echo energy of ps-interleaves indicates that the phase-cycled interleave pair were acquired at matched respiratory phases, and vice versa. Ste-iNAVs were also compared with c-iNAVs by assessing the correlation of motion estimated from iNAVs with respiration measured by dNAVs using the 15-average acquisitions. Specifically, for each of the first 15 heartbeats, the best phase-cycling match was found from subsequent heartbeats. Then ste-iNAVs were reconstructed and used to estimate respiration-induced heart motion (2D translations) between the ste-iNAVs. The translations were then correlated to the dNAV positions of the first 15 heartbeats. Correlations were analyzed for both x- and y-translations, and for all encoding dimensions. For comparison, translations were also estimated using c-iNAVs for the first 15 heartbeats of the same datasets and correlated to the dNAV positions. The Signed Rank test was used to test for statistically significant differences in correlations with significance level set at 0.05. In addition, the motion estimation algorithm was applied to ste-iNAVs reconstructed from the breath-holding datasets to demonstrate that negligible motion estimates are obtained in these conditions. The range of motion from breath-holding ste-iNAVs was compared to that estimated from free-breathing datasets.

Comparison of the Match-Making Framework with the Conventional dNAV and c-iNAV Methods for Reconstructing Free-Breathing Cine DENSE Images Finally, free-breathing cine DENSE magnitude and phase images reconstructed using dNAV, c-iNAV, and match-making framework were compared. Each of the volunteer datasets was reconstructed using all three methods. Because factors that affect intrinsic SNR such as number of averages, voxel size, and readout time were constant for all reconstruction methods, but breathing artifacts can lead to an apparent SNR reduction by effecting both the myocardial and background signals, the inventors compared the different reconstruction methods using the apparent SNR. The apparent SNR was measured from magnitude-reconstructed images using a region of interest (ROI) that included all of the myocardium within a slice and a large background ROI. The apparent SNR was calculated as the mean of the myocardial ROI divided by the standard deviation of the background ROI, and the correction for the Rician distribution of the magnitude signal was applied [28, 32]. In addition, phase quality (the variance of the local 2D spatial derivative of the phase image) [33, 34] was measured from all of the manually-segmented myocardium within each slice. Phase quality was calculated for background phase-corrected phase images after phase unwrapping. Also, for each reconstruction method, the residual T1-echo energy was computed from the corresponding raw data. Given that k-space energy varies among subjects and scans, for each dataset the residual T1-echo energy was normalized to a baseline value estimated from early systole (the minimal residual T1-echo energy within 300 ms after the displacement-encoding pulses) of the best matched phase-cycling interleaves and the normalized value is referred as relative residual T1-echo energy. In this way, the residual T1-echo energy can be compared both among reconstruction methods and among subjects. Apparent SNR, phase quality, and the relative residual T1-echo energy were averaged over all cardiac phases.

The total acceptance windows and the inter-phase-cycling motion for accepted data were also compared for each reconstruction method. The total acceptance windows were computed using the corresponding dNAV data defined as the range of dNAV positions for accepted heartbeats. The inter-phase-cycling motion was quantified as the difference in dNAV positions between the two interleaves of each accepted phase-cycling pair. All quantifications are presented as mean±standard error. One-way repeated-measures ANOVA (or one-way repeated-measures ANOVA with ranks if the normality test failed) was used to test for statistical significance with significance level set at 0.05. Lastly, circumferential strain was computed [34] using a single-slice six-segment model for each reconstruction method. Bland-Altman plots were used to analyze agreement of strain values from free-breathing acquisitions with those from breath-holding acquisitions.

Demonstration of the Match-Making Framework with Phantom Experiments

Results

Figure 9:
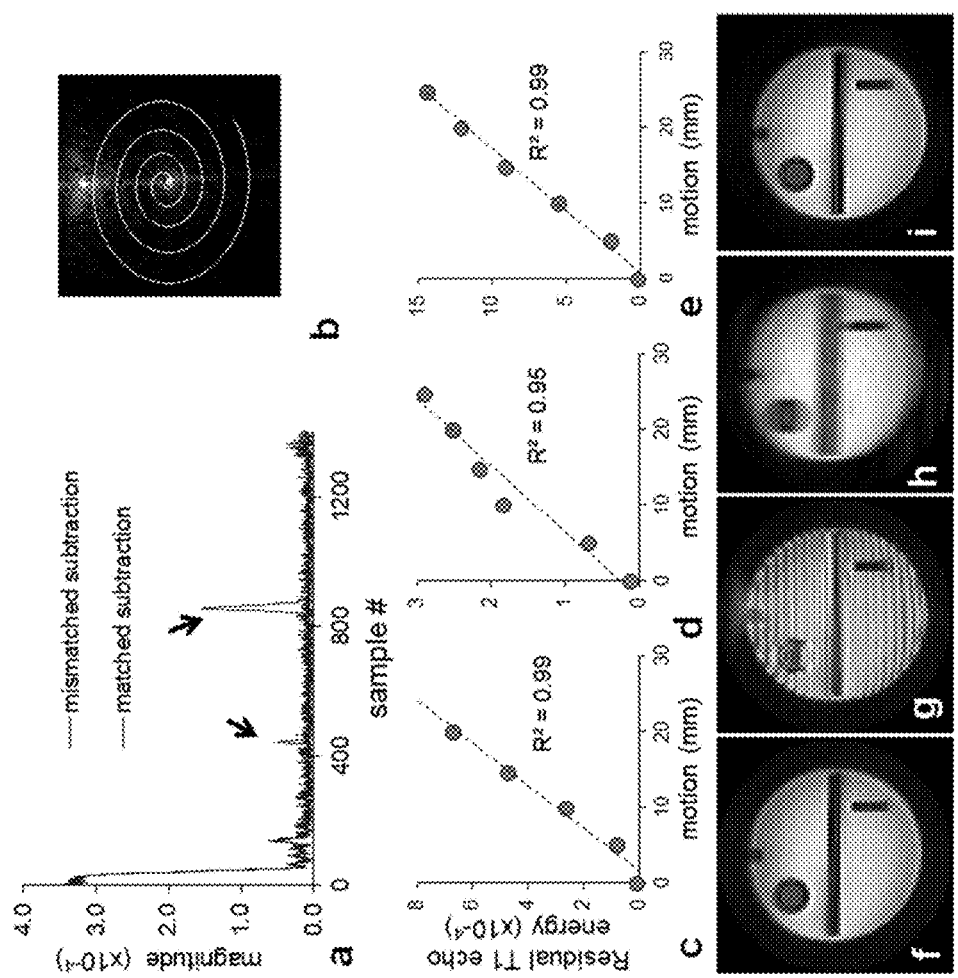
FIG. 9 shows the results of the phantom experiment demonstrating the match-maker method. (a) Intensities of k-space data along a post-subtraction spiral interleave (ps-interleave) from subtraction of matched phase-cycled interleaves (black curve) and mismatched phase-cycled interleaves (grey curve). Strong residual T1-relaxation echo signal remains in the ps-interleave from the mismatched subtraction (arrows). (b) Illustrative trajectory of the ps-interleave in (a). (c-e) Correlation between the residual T1-relaxation echo energy of the ps-interleave and the amount of translation between interleaves for in-plane motion (c), through-plane motion (d), and a combination of both in-plane and through-plane motion (e), respectively. (f-i) Demonstration of applying the match-maker framework for the cases of in-plane. (f) Motion-free reference images. (g) Images reconstructed using ps-interleaves of mismatched phase-cycled interleave pairs have strong striping artifacts and blurring. (h) The images from ps-interleaves with matched phase-cycling but with motion between ps-interleaves show removal of striping artifacts but still have blurring. (i) Using the match-making framework with motion compensation, blurring artifacts due to in-plane motion were also removed.

DENSE data were acquired from a phantom positioned at different locations to demonstrate the reduction of striping and blurring artifacts using matching of phase-cycled interleaves and ste-iNAV motion correction. Example k-space domain signals after subtraction of phase-cycled interleaves sampled along a spiral trajectory are illustrated in FIG. 9a. In one case (black line) the phase-cycled interleaves were acquired at matched locations and in the other case (grey line) the phase-cycled interleaves were acquired at mismatched locations.

Figure 10:
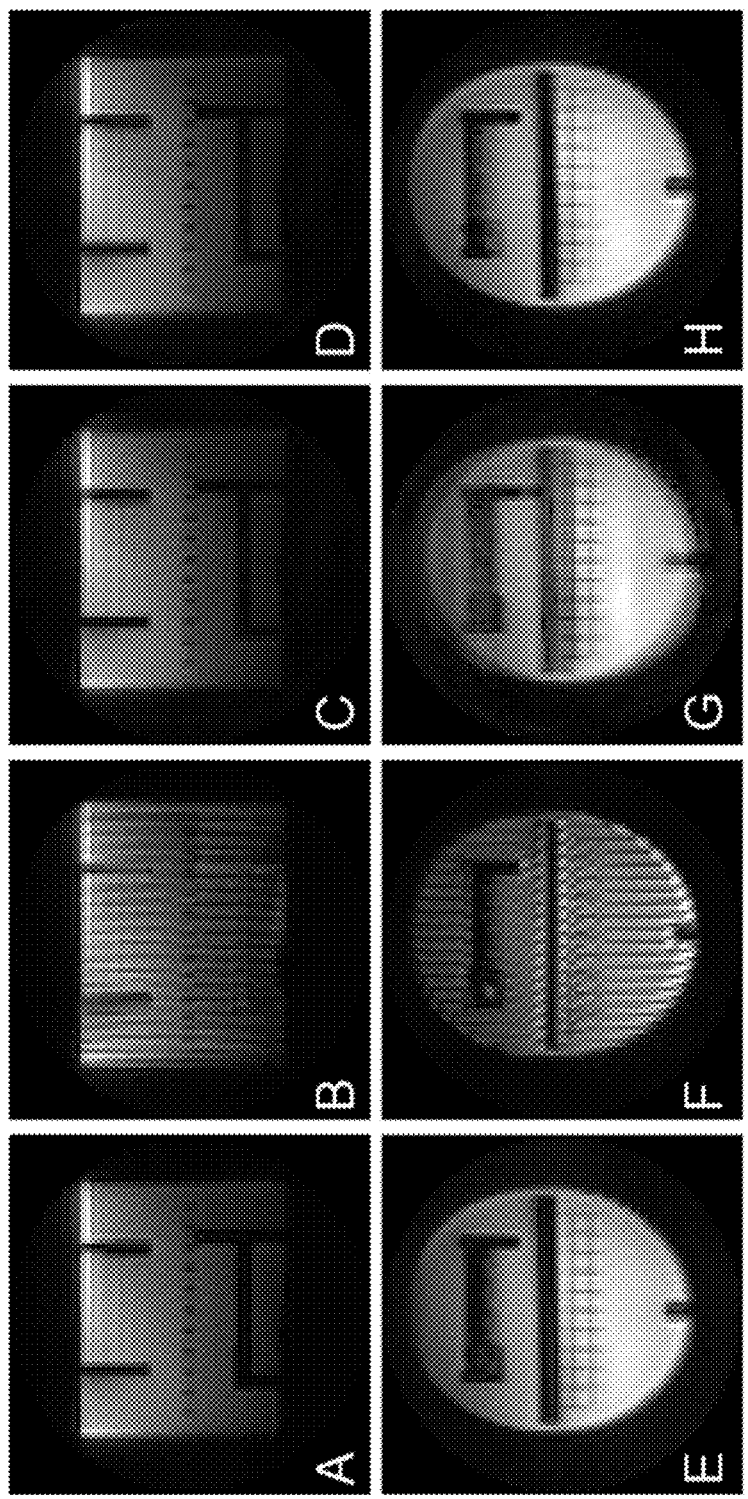
FIG. 10 shows a demonstration of applying the match-maker framework for the cases of through-plane (top) and combined motion (bottom). (a,e) Motion-free reference images. (b,f) Images reconstructed using ps-interleaves of mismatched phase-cycled interleave pairs have strong striping artifacts and blurring. (c,g) The images from ps-interleaves with matched phase-cycling but with motion between ps-interleaves show removal of striping artifacts but still have blurring. (d,h) Using the match-making framework with motion compensation, blurring artifacts due to in-plane motion were also removed.

For matched locations, the echo due to T1 relaxation is well suppressed, whereas for mismatched locations it is not (arrows). Multiple peaks corresponding to the T1-relaxation echo are observed because the spiral trajectory intersects the T1-relaxation echo multiple times, as shown in FIG. 9b. Experiments were performed where the phantom was moved between 0-25 mm with 5 mm increments, and FIG. 9c-e demonstrate that the residual T1-echo energy after subtraction of phase-cycled interleaves is linearly related to the distance the phantom was moved between the acquisitions of the phase-cycled interleaves. This finding holds for in-plane motion (FIG. 9c), through-plane motion (FIG. 9d), and a combination of in-plane and through-plane motion (FIG. 9e). These results show that the residual T1-echo energy is an indicator of the amount of motion between acquisitions of phase-cycled interleaves, and that very low residual T1-echo energy can be used to select phase-cycled interleaves acquired at matched locations (match-making). For the case of in-plane motion, FIG. 9g-h shows that striping artifacts are removed from the DENSE image when phase-cycled interleaves from matched locations are selected and subtracted, but image blurring still occurs when ps-interleaves from different locations are combined for the reconstruction. By using the ste-iNAV of each ps-interleave for motion estimation, k-space domain motion correction can be applied to compensate for the blurring induced by in-plane motion (FIG. 9i), and the images corrected for in-plane motion compare favorably to corresponding images from data acquired at a single position (FIG. 9f). The example images for the cases of through-plane motion and combined motion are shown in FIG. 10. Together, these results demonstrate the use of match-making and ste-iNAV-based motion estimation to compensate for motion-induced artifacts.

Evaluation of the Match-Making Framework in Volunteers

For in-vivo evaluation, two datasets were excluded from analysis due to extremely low SNR and extensive artifacts in images reconstructed by dNAV, c-iNAV and match-making methods. FIG. 1 demonstrates the use of the residual T1-echo energy as an effective criterion for matching phase-cycled interleaves for in vivo imaging. The respiratory pattern of a volunteer as measured by the dNAV signal is shown in FIG. 1a, and the respiratory phases of three interleaves are annotated. Specifically, interleave A (Int-A) and interleave B (Int-B) are a pair of phase-cycled interleaves acquired at different respiratory phases, while Int-B and Int-C are phase-cycled interleaves acquired at a similar respiratory phase. FIG. 1b shows the k-space domain data after subtraction of the two pairs of phase-cycled interleaves, and demonstrates suppression of the residual T1-echo for interleaves acquired at matched respiratory phases and substantial residual T1-echo signal for interleaves acquired at mismatched respiratory phases. FIG. 1c shows that the residual T1-echo energy remains low throughout the cardiac cycle for the phase-cycled interleaves acquired at similar respiratory phases, but increases for the phase-cycled interleaves acquired at different respiratory phases. For all phase-cycled interleave pairs from this acquisition, the relative residual T1-echo energy (averaged over all cardiac frames) was highly correlated with the difference in the corresponding dNAV positions, $\Delta$dNAV, with $R^2$ of 0.71. The average $R^2$ for all subjects was 0.61±0.04 (N=10). These results demonstrated that the relative residual T1-echo energy was an indicator of respiratory motion between phase-cycled interleaves.

Figure 11:
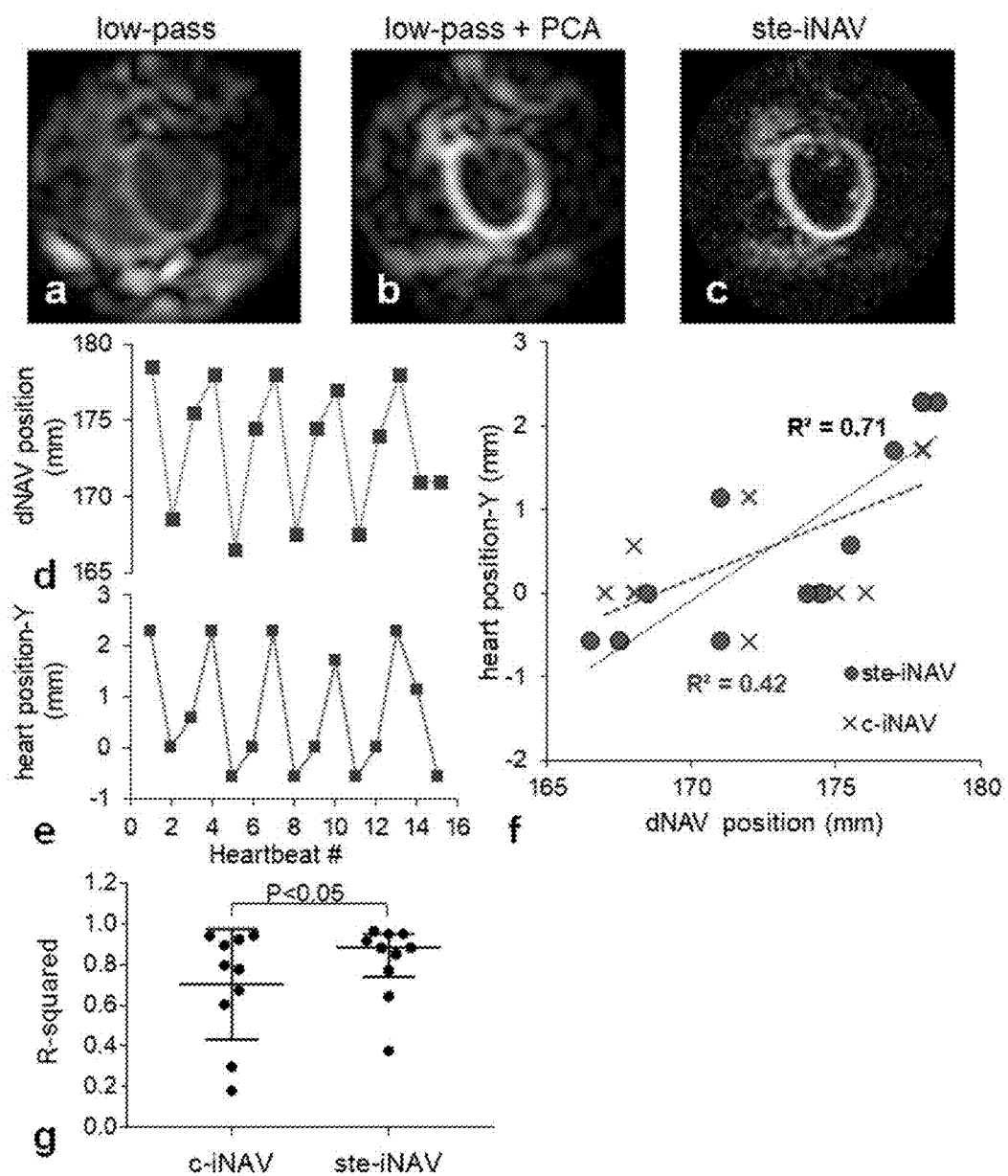
FIG. 11 shows a comparison of conventional iNAVs and ste-iNAVs. Example iNAVs are shown for (a) an iNAV reconstructed from pre-subtraction data with low-pass filtering, (b) an iNAV reconstructed with PCA-based and low-pass filtering, and (c) an ste-iNAV from matched ps-interleave data, which is localized to the heart region and provides higher spatial resolution. Panel (d) shows the dNAV positions for 15 consecutive heartbeats, and panel (e) shows heart motion estimated from ste-iNAVs for the same 15 heartbeats. Panel (f) provides an example showing that the correlation of iNAV-measured heart motion to dNAV position measured by ste-iNAVs is higher than for conventional iNAVs (c-iNAVs). Panel (g) shows the $R^2$ values for all five subjects and for both x- and y-translations and all encoding dimensions (median and interquartile range values are displayed).

Match-Maker Ste-iNAVs Assess Respiration-Induced Heart Motion Better than Conventional iNAVs FIG. 11 shows (a) a c-iNAV reconstructed using a simple low-pass filter to suppress the T1-relaxation echo, (b) a c-iNAV reconstructed using a simple low-pass filter and PCA filtering, and (c) a match-maker ste-iNAV. The ste-iNAV is localized to heart and depicts the heart more clearly than the c-iNAVs. Note that FIG. 11 shows navigator images, not reconstructed DENSE images. FIG. 11 also shows the correlation between respiration-induced heart motion as estimated by iNAVs and diaphragm motion as measured by dNAVs for both c-iNAVs (with low-pass and PCA filtering) and ste-iNAVs. As shown in FIG. 11g, the correlation for ste-iNAVs was significantly higher than that of c-iNAVs for the same datasets, with an $R^2$ of 0.82±0.03 vs. 0.70±0.05 (P<0.05). This result supports the premise that motion estimation was more accurate using ste-iNAVs compared to using c-iNAVs. Also, the overall range of heart motion due to respiration estimated from breath-holding ste-iNAVs was found to be negligible (0.62±0.20 mm, N=5) compared to the range of heart motion estimated from the free-breathing ste-iNAVs (6.75±3.33 mm, N=5).

Figure 12:
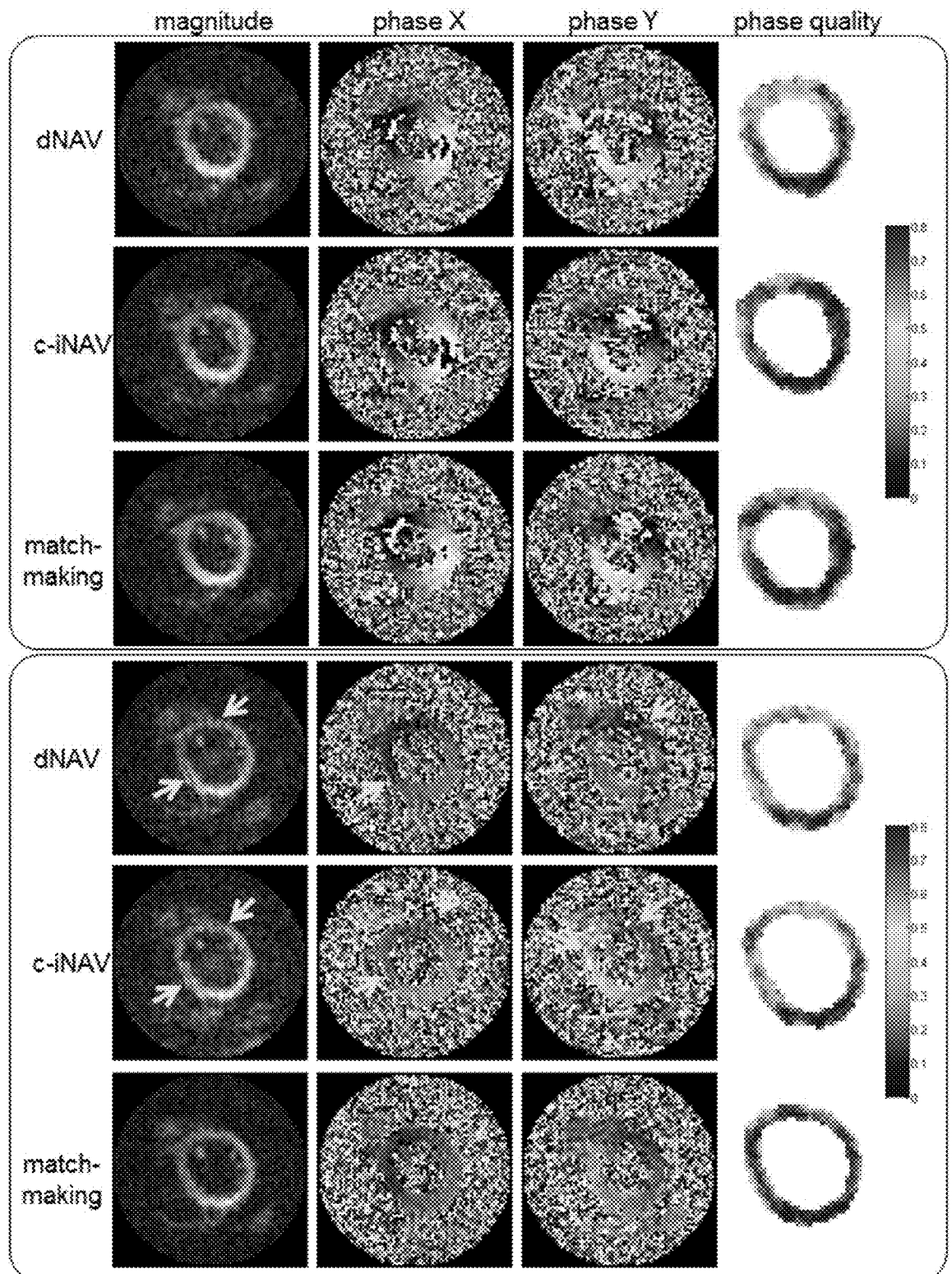
FIG. 12 shows an example end-systolic (top box) and diastolic (bottom box) DENSE images reconstructed using the conventional dNAV method, the c-iNAV method and the match-making framework for the same free-breathing volunteer raw data. The magnitude reconstructed images of the match-making method demonstrate lower artifact level, higher apparent SNR and better edge definition. The phase images of the match-making method have smoother phase in the myocardial ROI (arrows), and this is reflected in the better phase quality maps.

Comparison of Cine DENSE Reconstructions Using the Match-Making Framework with the Conventional c-iNAV and dNAV Methods Example cine DENSE magnitude and phase images for the dNAV, c-iNAV, and matchmaker reconstruction methods applied to the same raw data are shown in FIG. 12 for both systolic and diastolic cardiac frames. Magnitude reconstructed images using the dNAV and c-iNAV methods had striping artifacts due to residual T1-relaxation echoes (yellow arrows). However, for the match-making framework, the magnitude reconstructed image had less artifact, higher apparent SNR, and less blurring. The phase images of the match-maker framework had a smoother appearance within the myocardium. The relative residual T1-echo energy, apparent SNR, and phase quality are summarized for all volunteer data in FIG. 13a-c. The relative residual T1-echo energy of the match-making framework was significantly lower than that of the dNAV and c-iNAV methods, demonstrating that the match-making framework better suppressed the T1 relaxation echoes. The apparent SNR of the match-making framework was higher than for both the dNAV and c-iNAV methods, and the phase quality was lower or trended to be lower than that of the dNAV and c-iNAV methods, demonstrating better image quality.

Figure 13:
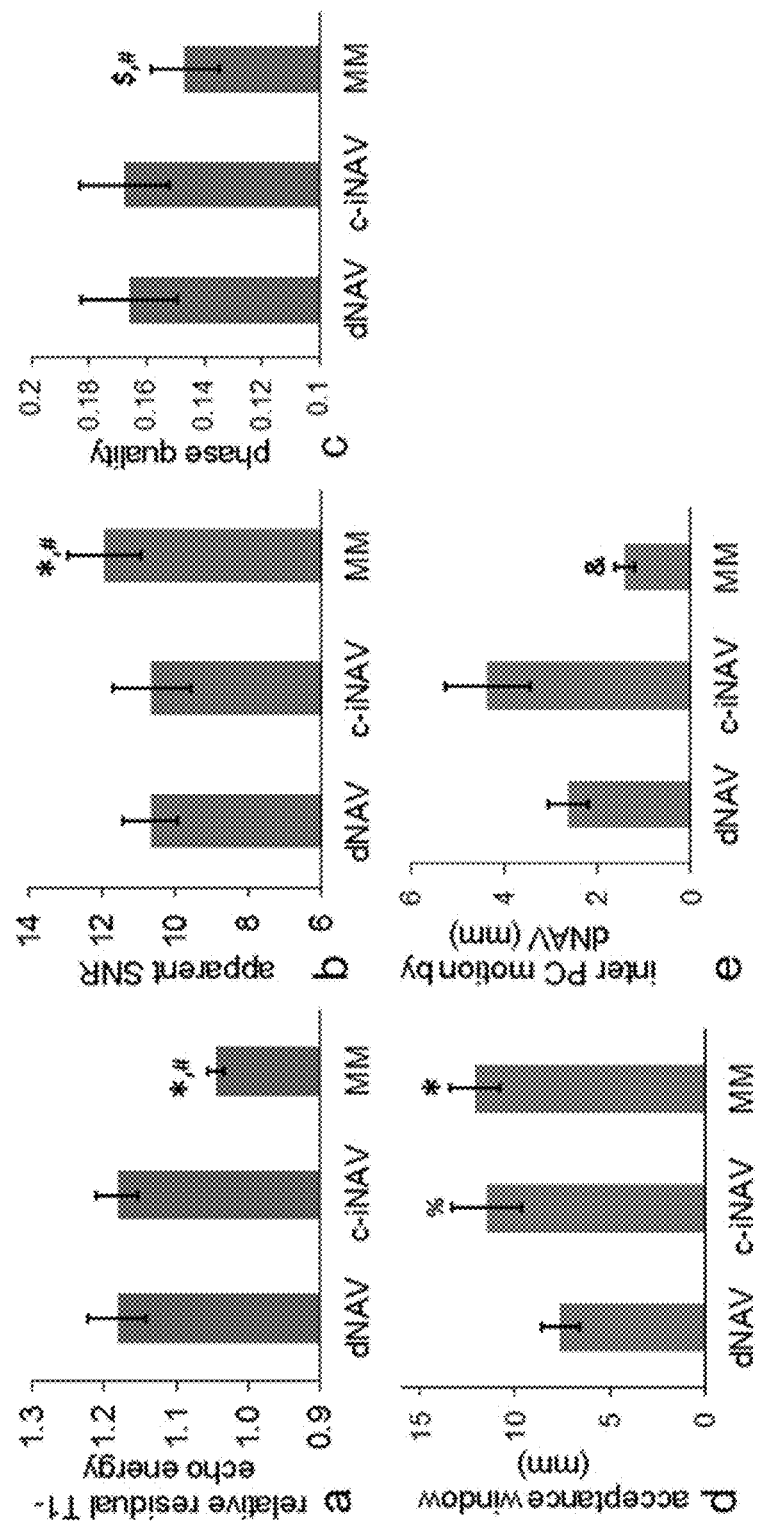
FIG. 13 shows quantitative comparisons for DENSE reconstructions using the match-making framework (MM) and the conventional dNAV and c-iNAV methods. (a) The relative residual T1-relaxation echo energy was lower for MM (*$P<0.05$ vs. dNAV; # $P<0.05$ vs. iNAV). (b) The apparent SNR of magnitude reconstructed images was higher for MM. (c) The phase quality of phase images was better for MM compared to c-iNAV and trended to be better compared to the dNAV method ($P=0.06$ vs. dNAV). (d) The match-making framework had a larger total acceptance window than the dNAV method, indicating that it accepted data from a wider range of respiratory phases (% $P=0.08$ vs. dNAV). (e) The motion within phase-cycled interleave pairs was smaller for MM than for the c-iNAV method (&$P<0.05$ vs. iNAV, one-way repeated measures ANOVA on ranks), indicating that the match-making framework identified phase-cycled interleaves at closer respiratory phases.

FIG. 13d-e compares the total acceptance windows (as measured by the dNAV positions) and the motion within each accepted phase-cycled interleave pair (as measured by the dNAV positions) for the dNAV and c-iNAV methods and for the match-making framework. The match-making framework had a larger total acceptance window than the conventional dNAV method, indicating that it accepted data from wider range of respiratory phases. The motion within selected phase-cycled interleave pairs was smaller for the match-making framework compared to the c-iNAV method.

Figure 14:
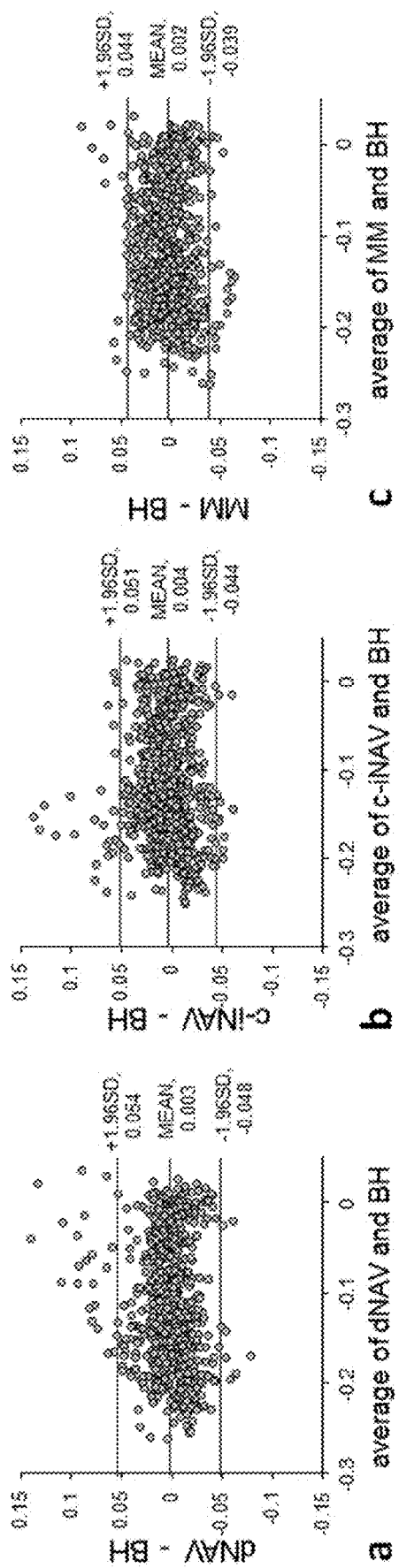
FIG. 14 shows a comparison of agreement of circumferential strain from free-breathing acquisitions with that from breath-holding acquisitions for each reconstruction method. The match-making framework (MM, panel c) provided better agreement of strain with breath-holding acquisitions (BH) than the conventional dNAV and c-iNAV methods (panels a, b).

FIG. 14 shows the Bland-Altman plots of circumferential strain comparing agreement between free-breathing and breath-holding acquisitions for all subjects and all segments. The match-making framework provided better agreement with breath-holding acquisitions than the dNAV and c-iNAV methods.

Discussion

In this study the inventors developed and evaluated a framework for self-navigated free breathing cine DENSE MRI that addresses two consequences of motion—striping artifacts due to incomplete suppression of the T1-relaxation echo and blurring. While a conventional iNAV approach is complicated by the presence of the T1-relaxation echo, the inventors showed that low post-subtraction residual T1-echo energy is a simple and useful metric to indicate whether phase-cycled DENSE interleaves were acquired at matched respiratory phases. While low residual T1-echo energy was shown to be effective for matching phase-cycled interleaves, this metric alone does not provide information about the absolute position of the heart and cannot be used for motion compensation of post-subtraction data. However, as described above, ste-iNAVs reconstructed from interleaves acquired at matched locations are localized, not contaminated by T1-relaxation echo artifacts, and can be used to accurately and automatically estimate in-plane heart motion due to respiration. Indeed, ste-iNAV motion estimation correlated better than conventional iNAV motion estimation with dNAV-measured respiratory motion, and the results further showed that the match-making framework reconstructions provided higher apparent SNR and a trend toward better phase quality for free-breathing cine DENSE than did the dNAV or c-iNAV reconstructions applied to the same raw data.

Both in-plane and through-plane motion can lead to changes in the complex T1-relaxation echo and, subsequently, to an increase of the residual T1-echo energy after subtraction of phase-cycled interleaves. In-plane displacement causes a phase shift of the k-space domain data. For through-plane motion, different tissue contributes to the different T1-relaxation echoes. Both types of motion lead to residual signal after subtraction of the phase-cycled interleaves. Although the underlying motion mechanisms leading to reduced T1-echo energy are different for in-plane and through-plane motion, in both cases low values of residual T1-echo energy identify phase-cycled interleaves acquired at matched locations.

Respiratory motion estimated by the ste-iNAVs correlated well with dNAV motion, as shown in FIG. 11g, whereas respiratory motion estimated by c-iNAVs had an overall lower correlation across all subjects. Furthermore, motion estimation using the ste-iNAVs was completely automatic, without needing manual definition of a region of interest. These results were obtained because the ste-iNAVs were designed to have suppression of the T1-relaxation echo and localized generation of stimulated echo. In addition, because c-iNAVs are reconstructed from data prior to phase-cycling subtraction, they incorporate signal from both the stimulated echo and the T1-relaxation echo. Even with PCA-based filtering and/or low-pass filtering, these iNAVs can still be corrupted by the T1-relaxation echo and are not well-localized to the heart. Therefore, the c-iNAVs are poorly-suited for respiratory motion estimation for cine DENSE. With these results, the match-making framework accepts data from any respiratory position and uses motion estimation and motion correction, while the dNAV and c-iNAV methods use retrospective gating but do not employ motion estimation and correction.

The total acceptance window, as defined by the full range of diaphragm positions for all accepted data, was greater for the match-making framework and trended to be larger for the c-iNAV method than for the conventional dNAV method. However, the motion between phase-cycled interleaves, as measured by the corresponding diaphragm positions, was lower for the match-making framework compared to the c-iNAV method. The lower amount of motion between phase-cycled interleaves led to a lower residual T1-echo energy and high quality ste-iNAVs for the match-making framework. Even though the total acceptance window was large, the high-quality ste-iNAVs provided good motion estimation and compensation, and altogether the match-making framework with motion estimation and compensation produced higher apparent SNR and better phase quality in human subjects than the c-iNAV method.

While the simple method for displacement encoding was used in this study, another option would have been to use the balanced displacement-encoding method [30]. With simple encoding, for the phase reference acquisition, the stimulated echo and T1-relaxation are overlaid in k-space, which is non-ideal for matchmaking (although matchmaking does still work for this case). The balanced displacement encoding method more naturally separates the stimulated echo and T1 relaxation echo in k-space for all displacement-encoding dimensions, and avoids the overlay problem. In the present study the simple method was chosen because it leads to less phase wrapping [30]. Nonetheless, balanced encoding may also be suited for use with match-making, perhaps when used in combination with lower displacement-encoding frequencies or more effective phase-unwrapping algorithms.

In conclusion, the match-making framework with motion estimation and compensation addresses both the striping and blurring effects of respiratory motion in free-breathing cine DENSE and provides advantages compared to conventional dNAV and c-iNAV methods.

Principle Component Analysis (PCA) to Separate Signals for Improved Conventional Cine Dense Inavs In this study, respiratory motion estimation using the match-maker ste-iNAV method and a conventional iNAV method were assessed. When implementing a simple conventional iNAV method for cine DENSE, it was found that the T1-relaxation echo led to very poor quality iNAVs and very poor motion estimation performance. To get improved performance, PCA was applied to the iNAV data to separate the stimulated-echo and T1-relaxation-echo signals, and iNAVs were reconstructed after removal of the main T1-relaxation-echo component.

Figure 15:
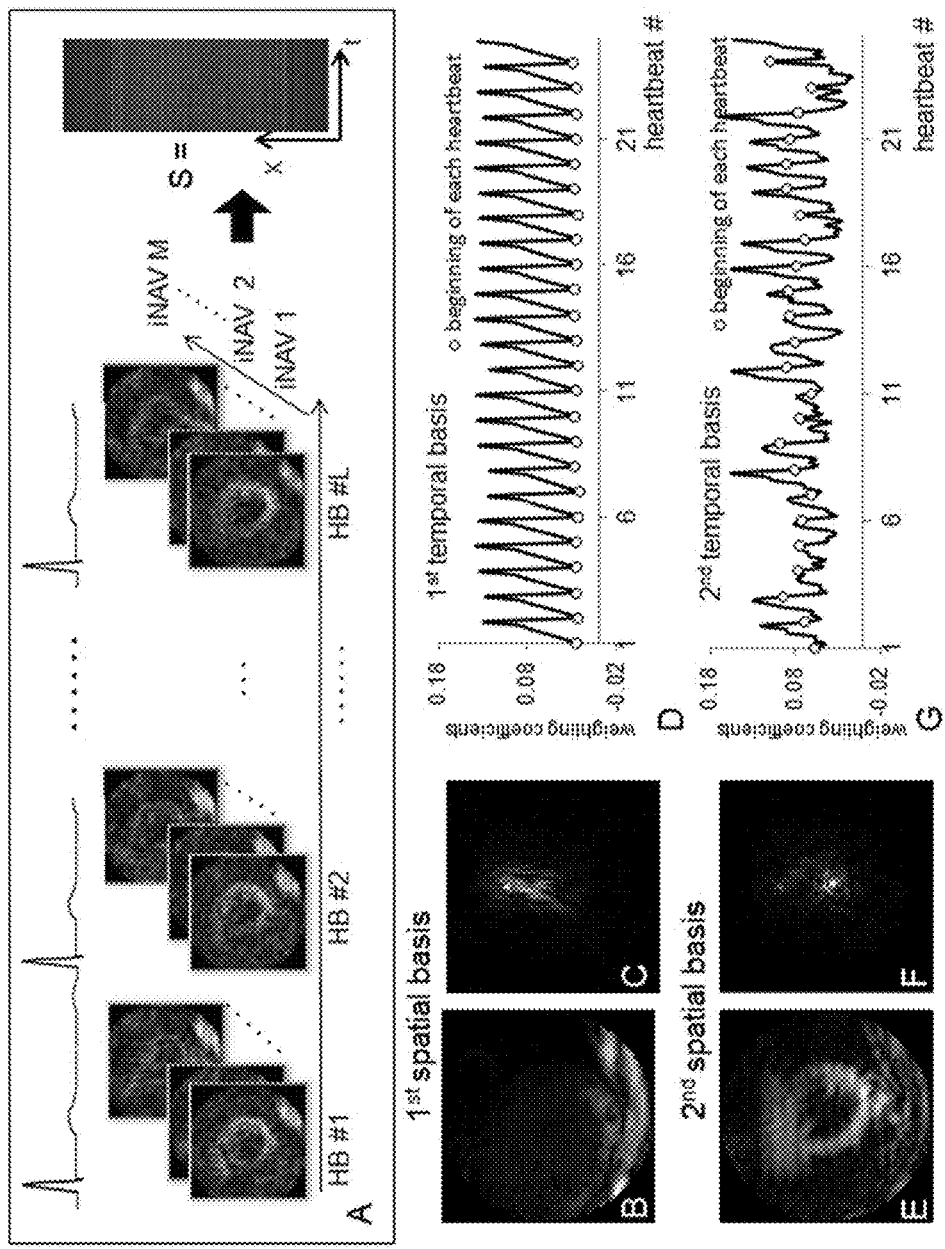
FIG. 15 shows a diagram of PCA-based filtering for improved cine DENSE conventional iNAVs. (a) Free-breathing cine DENSE data were acquired over multiple heartbeats. Within each heartbeat, multiple iNAVs are reconstructed by combining 8 consecutive spiral interleaves. All the iNAVs are organized into a Casorati matrix (S) where each column represents the pixels from each iNAV. (b-g): Results of PCA applied to the matrix (S). The first principle component is predominantly the T1-relaxation signal as shown in the image (b), k-space (c) and the corresponding temporal basis (d). The second principle component is mainly the stimulated echo (e-g). PCA-filtering to remove the first principle component provides an improved c-iNAV.

As shown in FIG. 15, preliminarily iNAVs were organized into a spatiotemporal Casorati matrix, S, where each column represents the pixels from each iNAV [40]. PCA was performed to decompose the matrix, S, into spatial and temporal bases. FIG. 15b-g shows the first and second spatial bases in the image and k-space domains, and also shows their temporal bases, respectively. The first spatial basis in the image and k-space domains and the first temporal basis were found to predominantly represent the T1-relaxation-echo signal (FIG. 15, b-d). The second spatial basis in the image and k-space domains and the second temporal basis were found to predominantly represent the stimulated-echo signal (FIG. 15, e-g). After the first principal component was removed and a low-pass filter was applied to the k-space data to further suppress the residual T1-relaxation-echo signal, iNAVs were reconstructed from the k-space data.

Figure 16:
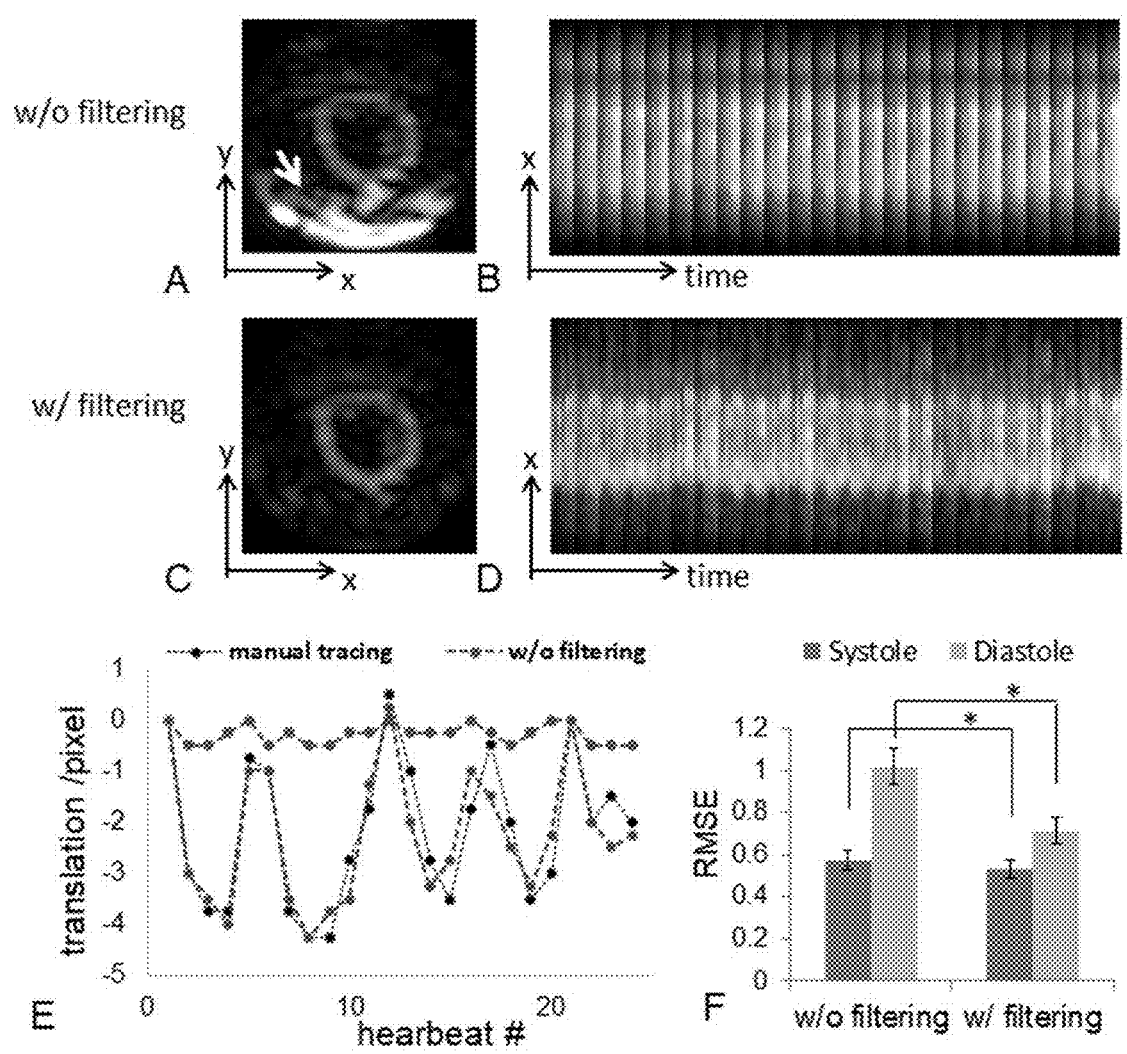
FIG. 16 shows a comparison of image quality and motion estimation accuracy of conventional iNAVs reconstructed without and with PCA-based filtering. (a-d) Example c-iNAVs and projections in the x-direction. The filtered images have markedly less T1 relaxation signal (arrow). Projections with PCA-based filtering show better visualization of respiratory motion (d vs. b). (e) Respiratory translations estimated by cross-correlation using the c-iNAV images without (w/o) and with (w/) PCA-based filtering. Results of manual tracing of the heart from the images reconstructed without filtering are shown as reference. The motion estimated from c-iNAVs with PCA-based filtering closely matches the manual tracing results while the motion from images without PCA-based filtering is not accurate. (f) Accuracy of motion estimated from iNAVs by root-mean-squared-error (RMSE) relative to manual tracing (*$P<0.05$, paired t-test, N=6). For both systole and diastole, motion estimated with iNAVs with PCA-based filtering has significantly less error than that without filtering.

Demonstration of the effect of PCA-based and low-pass filtering on the iNAVs is shown in FIG. 16. Without filtering, the iNAV has a strong T1 relaxation signal outside the heart (predominantly fat signal from chest wall in this example) (FIG. 16a, white arrow), while the iNAV reconstructed with filtering shows better suppression of the signal outside the heart (FIG. 16c). By using manually-tracked iNAVs as a reference, we showed that automatic motion estimation using cross-correlation applied to iNAVs with PCA-based and low-pass filtering had better performance for estimating motion of the heart due to respiration, whereas motion estimation applied to iNAVs without PCA-based filtering had worse performance (FIG. 16, e,f).

Adaptive Acquisition Algorithm to Minimize rT1E Methods

Figure 17:
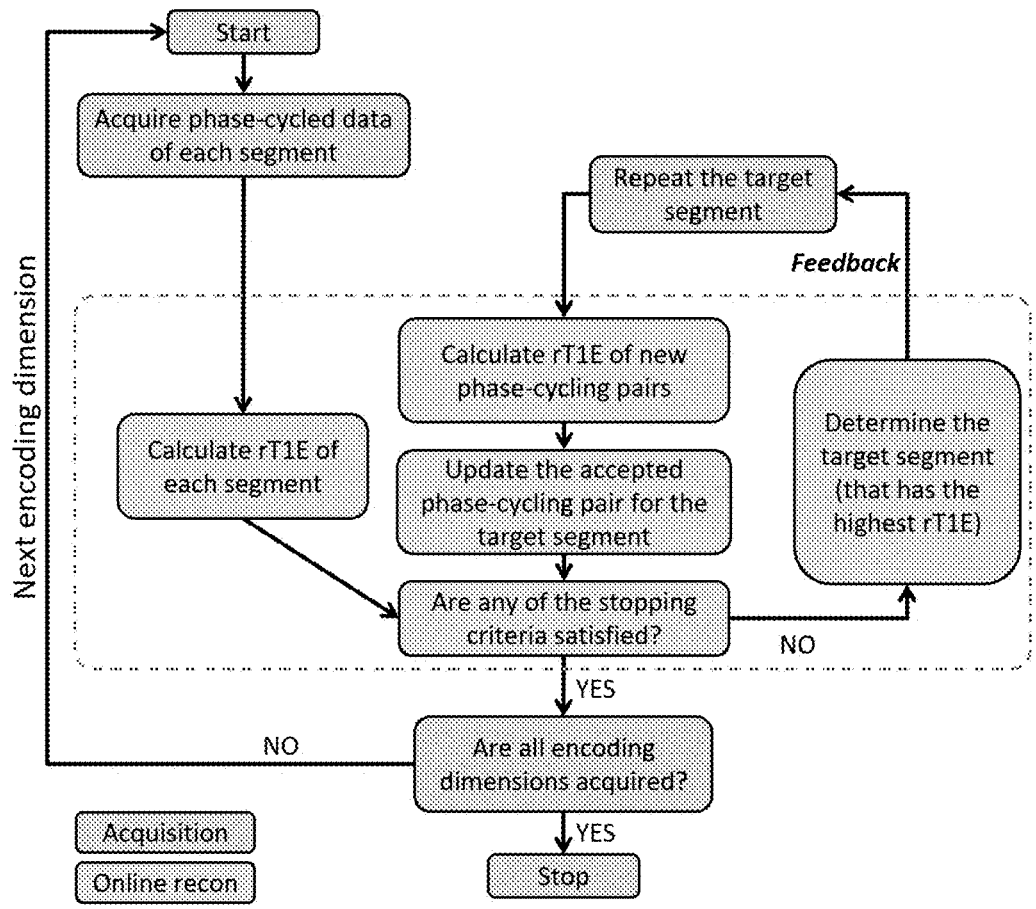
FIG. 17 is a diagram of the adaptive acquisition algorithm. The algorithm initializes by acquiring a complete set of k-space data, i.e. one instance of both phase-cycling dimensions for each segment. Then the online reconstruction environment performs subtraction of each phase-cycling pair and calculates the residual T_1-echo energy (rT1E) of each segment. The algorithm then compares the rT1E values with the stopping criteria. If they are not satisfied, then the algorithm determines the target segment with the highest rT1E and delivers the feedback to the sequence. Then the algorithm acquires another instance of the target segment for both phase-cycling dimensions. With the new data, the online reconstruction calculates the rT1E for each new phase-cycling pair and updates the best-matched phase-cycling pair for the target segment, i.e. selects the pair with the lowest rT1E. Afterward, the algorithm examines the rT1E again. The process continues until one of the stopping criteria is satisfied. The algorithm repeats the process for each encoding dimension separately and stops when all encoding dimensions are acquired.

One proposed algorithm for cine DENSE data acquisition with free-breathing is shown in FIG. 17. The overall objective is to reduce the rT1E of the post-subtraction data. The algorithm starts with the acquisition of fully-sampled k-space datasets for both phase-cycling dimensions, i.e. one phase-cycling pair for each k-space segment. In the online reconstruction environment, phase-cycling subtraction is performed for each phase-cycling pair and the rT1E values are calculated by summing post-subtraction k-space energy in a predefined region. Afterward, the rT1E values are examined to determine whether the existing data satisfy the stopping criteria. If not, the segment with the highest rT1E value is determined as the target segment and a real-time feedback is delivered to the data acquisition environment which then repeats acquisition of the target segment. With the new data, the online reconstruction calculates the rT1E values of the new phase-cycling pairs and updates the best-matched phase-cycling pair for the target segment, i.e. selecting the pair that has the lowest rT1E. After the update, the rT1E values are examined again. If one of the stopping criteria is satisfied, the acquisition stops; otherwise, the acquisition continues. During each iteration, the algorithm acquires another instance of the target segment for both phase-cycling dimensions. In other words, the acquisition takes 2 heartbeats at each iteration. Cine DENSE acquires a number of scans depending on the displacement encoding methods prescribed. In this chapter, each of these scans is referred to as an encoding dimension. The adaptive acquisition process is performed for each encoding dimension until all encoding dimensions are acquired.

The algorithm was implemented based on a 2D spiral cine DENSE sequence that supports localized generation of the stimulated echoes (53, 58). With this feature, the stimulated-echo signal only originates from the region where the two slice profiles intersect. Uniform rotation of the trajectory through cardiac frames was implemented. With these methods, image-based navigators (iNAV) can be reconstructed by combining spiral data of consecutive frames. These iNAVs are reconstructed after subtraction of phase-cyclings and therefore only contain the stimulated-echo (termed ste-iNAV) and are heart-localized.

Stopping Criteria

Specifically, there are three criteria in the current design: (1) The relative rT1E is below a threshold for all the cardiac frames; (2) The decrease percentage of rT1E is below a threshold; 3) The imaging time reaches a maximum limit. The imaging stops for the current encoding dimension when any of the criteria is satisfied.

The first criterion enforces the rT1E to be sufficiently low. The relative rT1E is calculated by normalizing the absolute rT1E to an estimated baseline value. Ideally, when the T1-relaxation echo is canceled perfectly, the rT1E is the energy of the displacement-encoded stimulated-echo in the predefined k-space region. Therefore, the rT1E should decrease and converge as the $T_1$-relaxation echo gets better suppressed. The absolute rT1E depends on various factors such as subject load, number of coils, and flip angle, etc. Therefore, the algorithm may not converge to the same value among different subjects and scans. However, the $T_1$-relaxation echo grows within the cardiac cycle when the phase-cycled data is not matched and the rT1E is always greater in diastole than in systole (53). Therefore, the average rT1E of frames during early systole (trigger time<=300 ms) is calculated as the baseline rT1E and the absolute rT1E is normalized to the baseline as the relative rT1E. The baseline value is updated as well at each iteration. The k-space region used for rT1E is defined as $|k|>|k_{max}|/2$.

The second and third criteria prevent the algorithm from progressing for too long. During the acquisition, it may take more than one iteration for the rT1E to be updated. However, if the rT1E does not change or decreases only marginally over a long time, it may indicate that the rT1E cannot be reduced further even when the first criterion is not satisfied. For criterion (3), the imaging time limit was determined to be 30 heartbeats per encoding dimension based on the empirical image protocol (6 heartbeats per encoding dimension with breath-hold) (42, 53) and efficiency of free-breathing cine DENSE (as low as 20%).

Compensation for Motion in the Stimulated Echoes

To compensate for inter-heartbeat motion, 2D translations are estimated with the ste-iNAVs by 2D cross-correlation. The translations are then corrected on the k-space data as described in previous studies (47, 69). The translation estimation and correction are first performed among the different segments of each encoding dimension and then among the encoding dimensions. Ste-iNAVs are re-reconstructed from the translation corrected k-space data for the next step of motion compensation.

Figure 18:
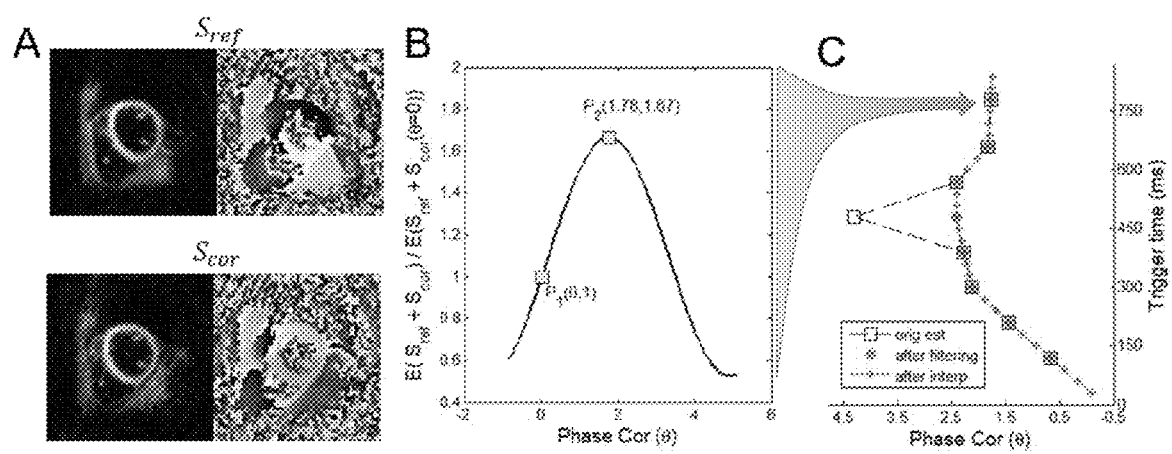
FIG. 18 is an illustration of phase error estimation based on ste-iNAVs. (A) ste-iNAVs at late diastole presenting the reference segment ($S_{ref}$) and the segment to be corrected ($S_{cor}$). The magnitude components of the two ste-iNAVs are similar to each other, while the phase components are different (red arrows), demonstrating phase errors due to intra-heartbeat motion. (B) The energy of the combined image (complex sum of $S_{ref}$ and $S_{cor}e^{i\theta}$) as a function of phase correction values ($\theta$). The presented data is normalized by the combined image energy without correction, i.e. $P_1$. The phase correction is determined as the one that maximizes the combined image energy ($P_2$). (C) Phase error estimation can be estimated for the ste-iNAVs (square markers). Median filtering is applied to remove noise in the estimation due to rapid heart motion during early diastole (green markers). Then the phase errors of all the cardiac frames are estimated by linear interpolation (pink markers).

In order to reduce signal cancellation, phase error due to intra-heartbeat motion is estimated and compensated. Here, only the phase due to translations is considered, i.e. the correction is a spatially-invariant (65). FIG. 18 illustrates the estimation of the phase correction values for each k-space segment. Within each encoding dimension, one segment is chosen as the reference segment and the other segments are corrected. The estimation is performed for each iNAV-frame by maximizing the energy of the combined image (complex sum) of the reference ste-iNAV and the corrected ste-iNAV. As shown in FIG. 18A, the ste-iNAVs of the reference segment ($S_{ref}$) and the segment to be corrected ($S_{cor}$) have different phases (red arrows). The energy of the combined image of $S_{ref}$ and $S_{cor}$ with phase correction (θ) is defined as, $$E(\theta)=\|S_{ref}+S_{cor}e^{-i\theta}\|_2 \quad (1)$$

The $E(\theta:\theta\in(-\pi, \pi))$ for the example ste-iNAVs is shown in FIG. 18B. The phase value that maximizes E(θ) is determined as the correction value for the current ste-iNAV frame. The estimation is performed for all the ste-iNAV frames as in FIG. 18C (square markers). Then the phase correction values are smoothed with a third order median filter (green markers) and linearly interpolated to estimate the correction for all the cardiac frames (pink curve). After phase error correction, the cine DENSE images are reconstructed with non-uniform fast Fourier Transform (NUFFT) (60). The phase error estimation is performed for each encoding dimension separately. After the images of all encoding dimensions are reconstructed, the combined magnitude images and displacement-encoded phase images are extracted (61).

Reference Segment Selection for Phase Correction

To reduce the bulk phase error in the final displacement-encoded phase images, the reference segments of all encoding dimensions are jointly determined using the ste-iNAVs. The aim is to determine a combination of reference segments, one per encoding dimension, that minimize the overall displacement phase at late-diastole. Given that the phase due to tissue displacement increases during systole and rewinds during diastole, the bulk phase errors due to the intra-heartbeat motion can be minimized by selecting reference segments that minimize the averaged displacement phase at late-diastole. For each combination of ste-iNAVs, the overall displacement phase φ is defined as, $$\varphi(i,j,k)=\text{angle}[\Sigma_r D(I_{1,i}, I_{2,j}, I_{3,k})] \quad (2)$$

where $I_{1,i}$, $I_{2,j}$, $I_{3,k}$ indicates the late-diastolic ste-iNAVs of the $i^{th}$, $j^{th}$, $k^{th}$ segment of the first, second and third encoding dimensions respectively. D indicates the operation to extract displacement phase images (61). r is the spatial locations in the 2D imaging plane. The magnitudes of the displacement phase images are calculated as the average of the input ste-iNAVs, $I_{1,i}$, $I_{2,j}$, and $I_{3,k}$. The reference segments of all encoding dimensions are determined as the combination that minimizes φ, $$(S_{ref,1}, S_{ref,2}, S_{ref,3}) = \min_{i,j,k}|\varphi(i, j, k)| \quad (3)$$

Two sets of reference segments are determined for extraction of the displacement encoded phases images in the x- and y-directions respectively.

Experiments to Determine Stopping Criteria 1 and 2

To determine the threshold values for criteria (35) and (36), 10 healthy subjects (6 female, 27±4 years old) were scanned on a 3T system (Magnetom Prisma, Siemens Healthineers, Erlangen, Germany) with a 32-channel spine coil and a 6-channel body coil. All human subject scans in this study were performed in accordance with protocols approved by the institutional review board and with informed consent. Free-breathing cine DENSE datasets were acquired using the adaptive algorithm with criterion (37) only and on a mid-ventricular short-axis slice with the following parameters: slice thickness 8 mm, FOV=320×320 mm², width of the localized stimulated-echo region=90~110 mm, 6 spiral interleaves per image, 2 interleaves per segment, TR=15 ms, temporal resolution=30 ms, TE=1.08 ms, spiral readout length of 5.5 ms, matrix size of 128×128, balanced displacement encoding with encoding frequency=0.05 cyc/mm (61). Ramped flip angles with a final flip angle of 15 degrees were employed. Multiple frames were imaged with prospective ECG triggering covering approximately 80% of the RR interval. Fat suppression was applied immediately after each ECG trigger. The imaging parameters were chosen in consistency with previous studies. The total scan time was 92 heartbeats with the first two heartbeats used for the acquisition of field map data.

Each DENSE dataset was processed offline in MATLAB (MathWorks, Natick, Mass.). Cine DENSE images were reconstructed for each iteration in three ways: 1) NUFFT without ste-iNAV based motion correction, 2) with additional phase error correction and 3) with both phase error correction and translation correction. The reconstruction was performed separately for each of the encoding dimensions. The final displacement phase images were not extracted as the end time points of the encoding dimensions were unknown. The relative rT1E values and image quality quantified as apparent SNR were analyzed for each iteration and each encoding dimension to determine the threshold of criterion (1). The relative rT1E was averaged through cardiac frames. The apparent SNR was quantified for a diastolic frame (trigger time=600 ms) with a myocardium region of interest and a background region. Correction for Rician distribution was applied during SNR quantification (62,63). At each iteration when the rT1E was updated, the previous rT1E, percentage of decrease in rT1E and the time cost (number of iterations since the last rT1E update) were recorded to determine criterion (2). The center frequency shift was estimated from the field maps and corrected in k-space (64, 65).

Experiments to Evaluate the Self-NAV Method

With threshold values determined from the previous experiments, the proposed self-NAV method was evaluated in healthy subjects and patients. A total number of 23 subjects (10 healthy subjects, 5 female, 26±3 years old; 13 patients with heart disease, 7 females, 57±16 years old) were scanned on 3T systems (Magnetom Prisma and Skyra, Siemens Healthineers, Erlangen, Germany). Exclusion criteria for patient recruiting included inability to breath-hold, ages (pediatrics) and implantable devices, such as pacemakers, ICD or CRT. A patient dataset was excluded due to extreme phase errors induced by intra-heartbeat motion. For each subject, cine DENSE datasets were acquired on a mid-ventricular slice once with breath-hold, twice with self-NAV and twice with dNAV. The imaging parameters are the same as those in the experiments to determine the stopping criteria. The breath-hold acquisitions were performed at end-expiration in healthy subjects and at end-inspiration in patients. Criteria (1) and (3) were applied prospectively and criterion (2) was applied retrospectively in healthy subjects. All criteria were applied prospectively in patients. For dNAV, a diaphragm navigator was acquired in late diastole and right after cine DENSE data acquisition of each heartbeat. The acceptance window was set at end-expiration with a width of ±2 mm.

Each dataset from with the self-NAV method was reconstructed offline in MATLAB to apply translation and phase correction. The breath-hold and dNAV acquisitions were reconstructed with NUFFT. Displacement phase images and combined magnitude images were extracted afterwards. The relative rT1E was calculated for each cine DENSE dataset. The apparent SNR was quantified for the combined magnitude images. Segmental circumferential strain values were computed with the displacement phase images for 6 segments of the left ventricle using the standardized AHA segmentation model (66-68). Both the relative rT1E and the apparent SNR were averaged through cardiac frames and compared among breath-hold, self-NAV and dNAV with one-way repeated measure ANOVA on ranks and one-way repeated measure ANOVA respectively. Between the two free-breathing methods, imaging time was compared with signed rank test and agreement of free-breathing strain with breath-hold strain and reproducibility of breathing strain were analyzed using Bland-Altman plots. All statistical tests are performed using SigmaPlot (Systat Software Inc).

The reference segment selection method of self-NAV was assessed using the datasets acquired in healthy subjects. With the breath-hold acquisition, the ste-iNAVs were reconstructed for the same late-diastole iNAV frame as that of self-NAV. The displacement encoded phase image was extracted from these ste-iNAVs. With the self-NAV acquisition, the displacement encoded phase image was also extracted for each combination of ste-iNAVs. Then the overall phase was calculated with equation [2] and the phase error relative to the breath-hold displacement encoded phase image was also estimated using the method in FIG. 18. The overall displacement phase was then correlated with the estimated phase error relative to breath-hold.

Results

Improving Image Quality During the Adaptive Acquisition

Figure 19:
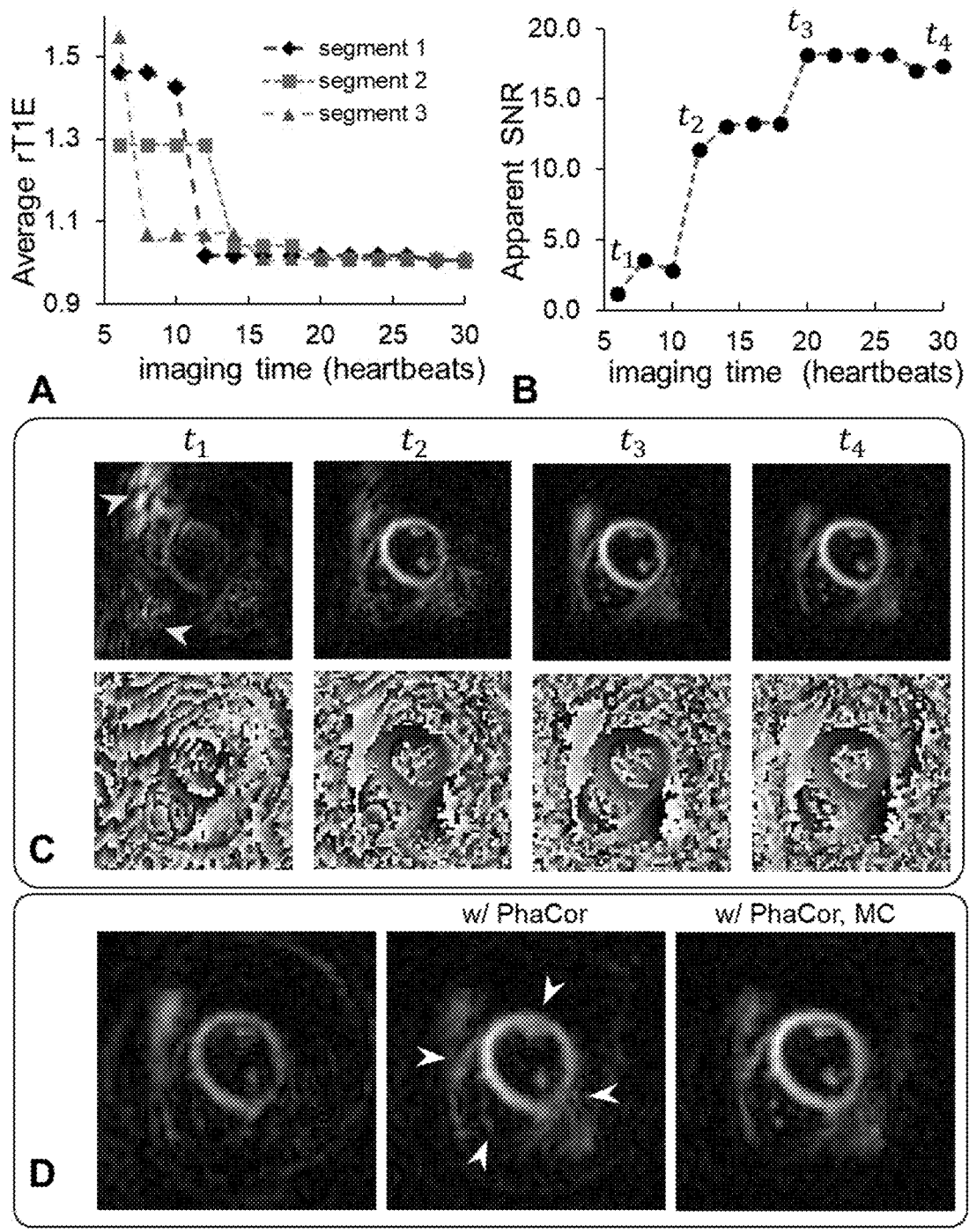
FIG. 19 shows results from an adaptive FB cine DENSE dataset acquired for a fixed duration of 30 heartbeats on a healthy subject. (A). rT1E of each k-space segment decreased as the imaging progressed. (B). The corresponding SNR of DENSE images increased. (C) Diastolic images at four different time points during the acquisition (as indicated in panel (B)) demonstrate improving image quality during the adaptive acquisition. Both the magnitude (top row) and the phase (bottom row) images are shown. (D) Reconstruction at time $t_4$ with different corrections. Left: without phase error or translation correction. Middle: with phase error correction. Right: with phase error and translation corrections.

FIG. 19A-C demonstrates that the adaptive algorithm reduces rT1E and improves image quality efficiently during the acquisition. The relative rT1E at each time during the acquisition is shown in FIG. 19A. At beginning of the acquisition (time=6 heartbeats), segment #3 was the target segment with the highest rT1E. Therefore, the algorithm repeated acquisition of this segment, after which the rT1E of segment #3 decreased (time=8 heartbeats). Segment #1 then became new target segment and was repeated. The acquisition continued and after 20 heartbeats, the relative rT1E values of all segments were very low and the change was small. The apparent SNR of the images at each time is shown in FIG. 19B. The apparent SNR increased as the algorithm progressed, demonstrating improvement in the image quality. The images at 4 time points during the acquisition are shown in FIG. 19C. Both the magnitude (top row) and phase (bottom row) images at a late diastole frame are shown. Strong artifacts were present in the images at the initial stage of the acquisition ($t_1$). As the algorithm progressed, the artifacts in the images were reduced ($t_2$-$t_4$).

FIG. 19D shows the different reconstructions at $t_4$. The image reconstructed without ste-iNAV based motion correction (left) had severe signal cancellation due to intra-heartbeat motion induced phase errors. Reconstruction with phase error correction had improved image intensity (middle). Translation correction further reduced blurriness and improved image quality (right). The images shown in FIG. 19C were reconstructed with both phase error correction and translation correction. These results demonstrated that both phase correction and translation correction are essential to compensate for motion in the stimulated-echoes to reduce motion artifacts.

Selection of Threshold Values

Figure 20:
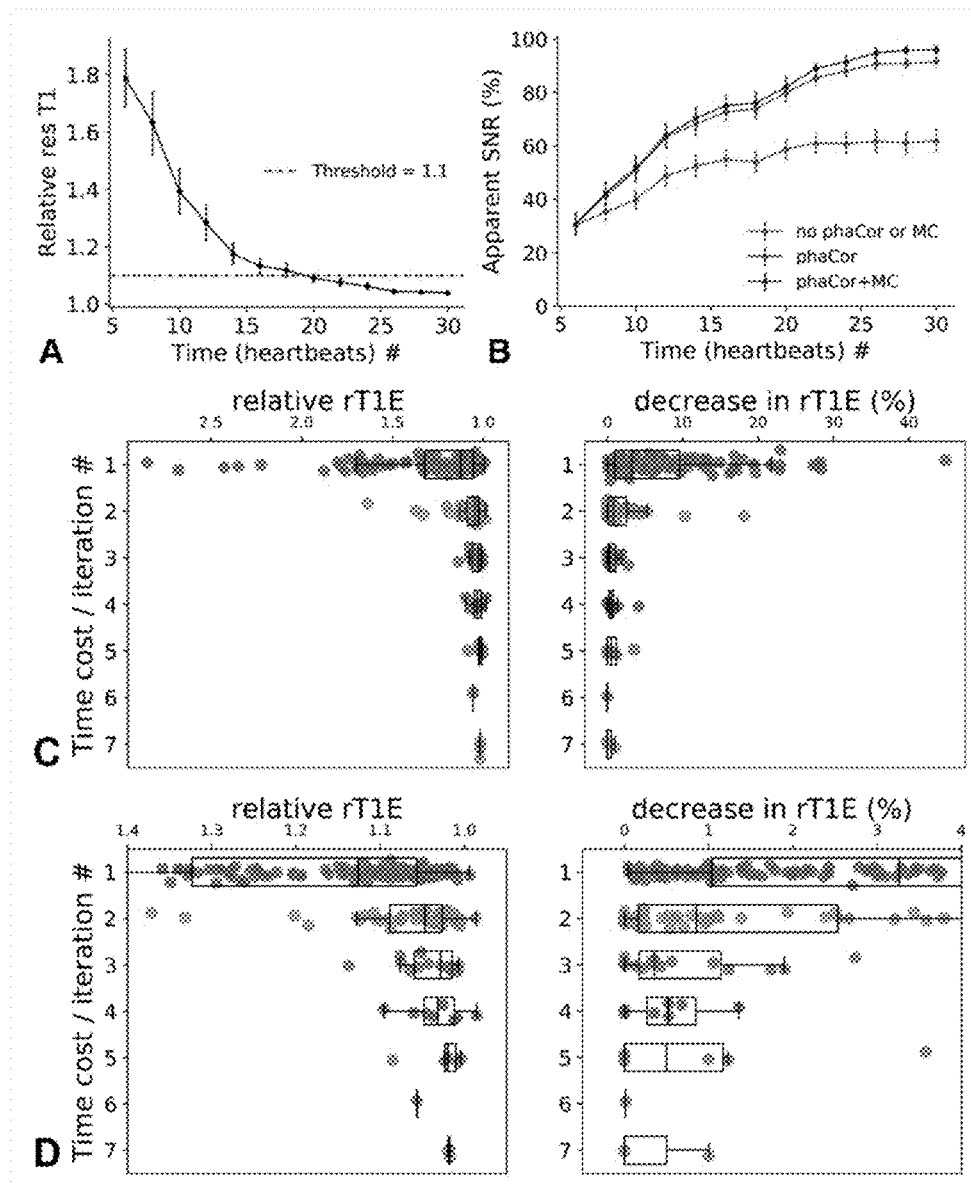
FIG. 20 shows a summary of rT1E and image quality in all subjects during the adaptive acquisition with a fixed imaging duration. (A) The relative rT1E converged to a value close to 1.0. (B) The image quality (apparent SNR, normalized to that at time=30 heartbeats) increased. Compared to the reconstruction without phase error or translation correction (pink curve), phase error correction significantly improved image apparent SNR (green curve). Translation correction further improved the apparent SNR (blue curve). A threshold value of 1.1 (red dashed line) was chosen for rT1E based on these results. (C-D) The relative rT1E at iterations when the rT1E were updated (left) and the corresponding decreases in rT1E (right). Panel D is a zoom-in of panel C at low rT1E and rT1E decrease ranges. These results included the acquisition processes of all subjects and all encoding dimensions and the data are grouped based on the duration it takes for the rT1E to decrease (y-axis). These results demonstrated that most of the times, it took one or two iterations for the rT1E to decrease (blue and orange data points). The longer it takes to update the rT1E, the lower is the current rT1E and the rT1E decrease percentage.

Results of the experiment to determine the threshold values are summarized in FIG. 20. Panel A summarizes the relative rT1E of all encoding dimensions and subjects. Overall, the relative rT1E converged to a value close to 1.0, indicating that the relative rT1E of diastolic frames decreased to close to that of early systolic frames in all subjects. Panel B shows that the apparent SNR (normalized to the SNR at time=30 heartbeats) improved correspondingly. Specifically, without translation correction or phase correction, the apparent SNR improved from 30% to 60% (pink plot). Application of phase error correction reduced signal cancellation and improved the apparent SNR from 60% to 85% after 20 heartbeats (green plot). Then translation correction further improved the image quality marginally (blue plot). These results demonstrate that a threshold on the relative rT1E can be applied to prospectively ensure matched phase-cycling pairs and ste-iNAV based compensation for both intra-heartbeat and inter-heartbeat motion is critical for reconstruction of free-breathing cine DENSE images. Based on these results, a value of 1.1 was chosen for the relative rT1E threshold in criterion (1).

Panel C-D demonstrates that most rT1E changes happened after only one iteration (blue points). The relative rT1E and rT1E reduction in this group varies in a wide range. As the time cost increases, the relative rT1E is lower (below 1.2 for time cost>=3 iterations), and the decrease in rT1E is also smaller (below 5% for time cost>=3 iterations). These results suggest that the longer it takes for an update in rT1E to occur, the less benefit there is. Based on these results, criterion (2) is reached when the rT1E decrease less than 1% over 3 iterations.

Comparison with dNAV

Figure 21:
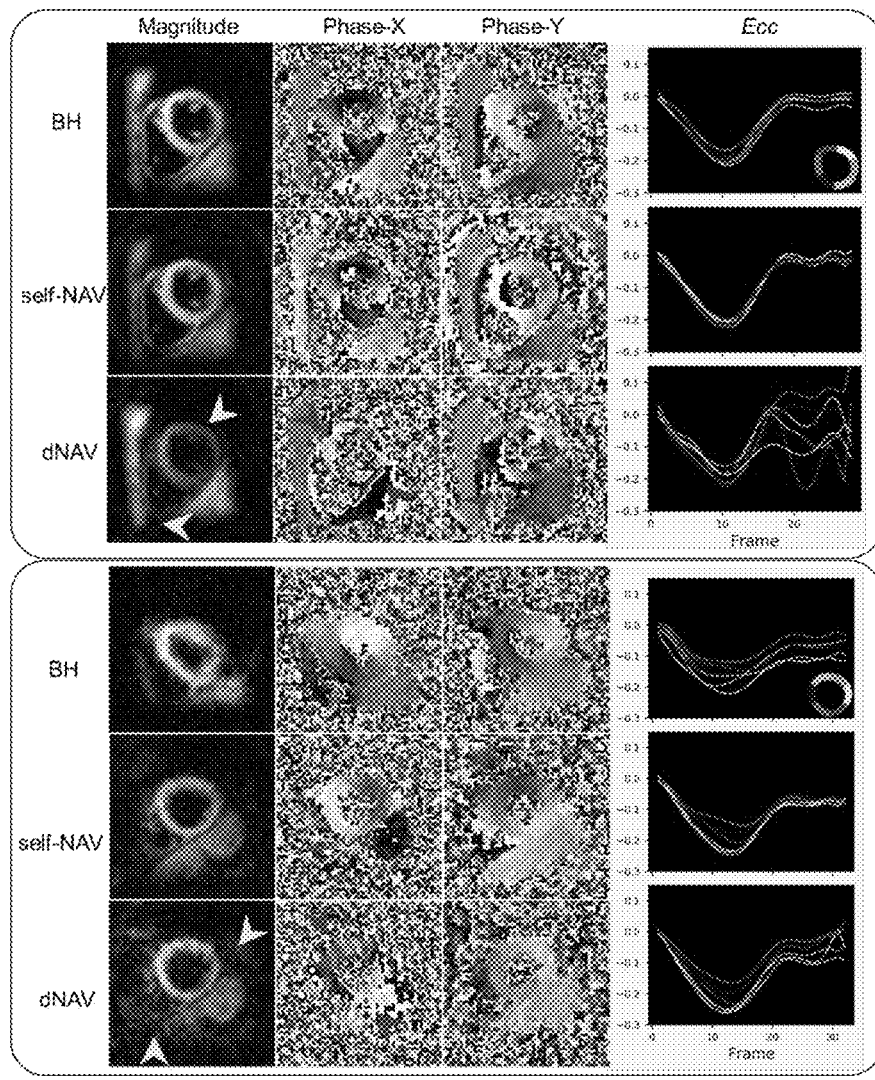
FIG. 21 shows example cine DENSE images and circumferential strain acquired with BH, self-NAV and dNAV methods from a healthy subject (top box) and a patient (bottom box). End-systolic frames are shown. In the healthy subject, the images acquired with dNAV had artifacts and reduced SNR in the magnitudes (yellow arrows) and errors in the myocardium displacement phase (red arrows). The images acquired with self-NAV had high-quality magnitude and phase images. The segmental strain curves by dNAV had severe errors while the strain curves by the self-NAV method well-resembled those by BH. In the patient, the BH images were blurry. Self-NAV produced the best quality images and segmental strain. With dNAV, the images had more striping and blurring artifacts (yellow arrows) and phase errors (red arrows). The BH was performed at end-inspiration and therefore the heart position was different from those of free-breathing acquisitions. (BH: breath-hold; self-NAV: self-navigated method; dNAV: diaphragm-based navigator gating method)

FIG. 21 shows example cine DENSE images at end-systole and circumferential strains acquired on a healthy subject and a patient with breath-hold, self-NAV and dNAV. In the healthy subject, the images and strain curves acquired with breath-hold are high quality. The images acquired with dNAV method had severe artifacts in the magnitude (yellow arrows), phase errors in the phase images (red arrows) and errors in the strain curves. The images and strain curves by self-NAV resemble the quality of those from breath-hold acquisition. In the patient, the breath-hold images have little striping artifacts but are blurry. The free-breathing images with dNAV had residual artifacts (yellow arrows) and phase errors in the images (red arrows). The images by self-NAV have less blurriness and residual $T_1$-echo signal than dNAV. The self-NAV and dNAV produced similar strain curves.

Figure 22:
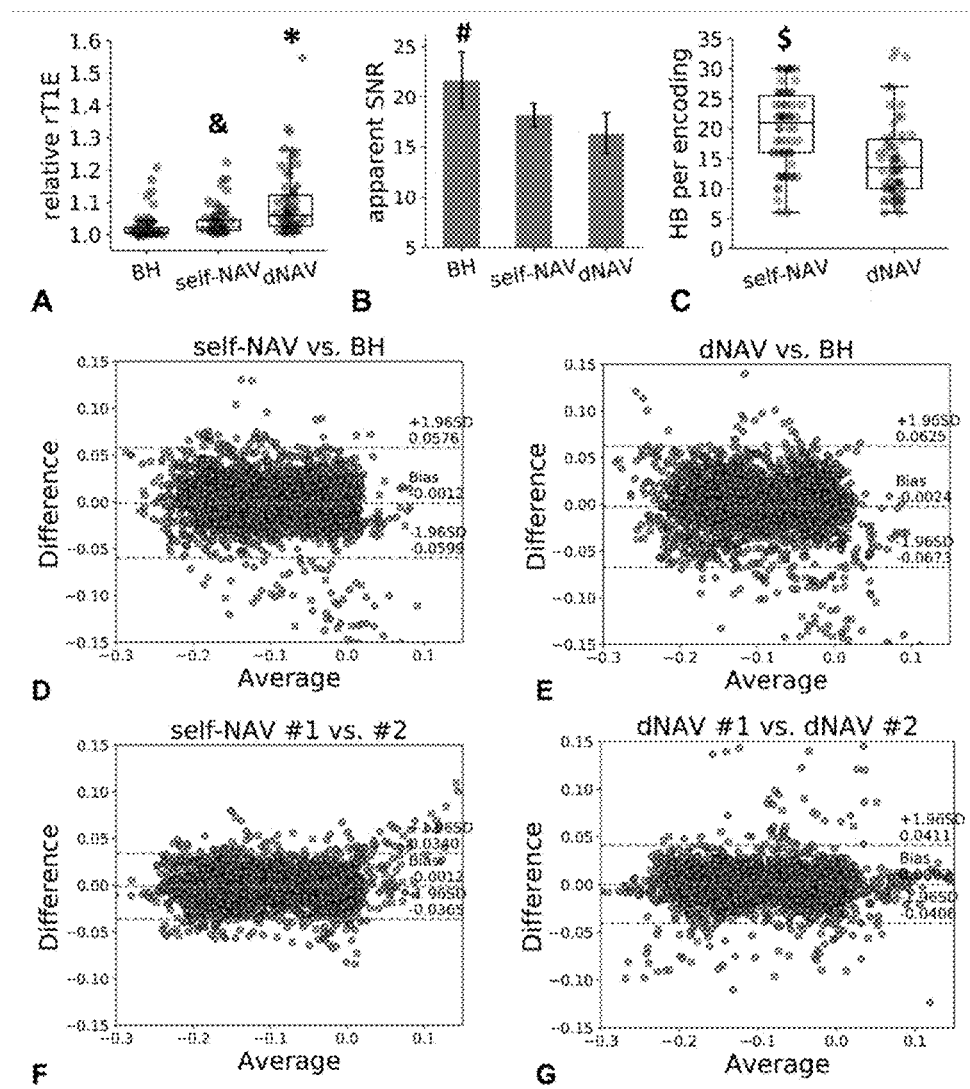
FIG. 22 shows a summary of evaluation results in all subjects. (A) The relative rT1E. BH overall achieved a lower relative rT1E than FB acquisitions. The self-NAV method achieved lower rT1E than dNAV. (B) Apparent SNR. BH had the highest SNR. The SNR of the dNAV method trended to be lower than self-NAV. (C) The imaging time of dNAV was less than self-NAV by 4 heartbeats per encoding dimension. (D-E) The Ecc by self-NAV was in better agreement with that by BH than dNAV. (F-G) The Ecc by the self-navigation method was more reproducible than that by dNAV. (*P<0.05 vs. BH, self-NAV, &P<0.05 vs. BH, one-way repeated measure ANOVA on ranks; # P<0.05, one-way repeated measure ANOVA; $P<0.05, signed rank test) (BH: breath-hold; self-NAV: self-navigated method; dNAV: diaphragm-based navigator gating method)

FIG. 22 summarizes the comparison of self-NAV with dNAV. The rT1E of self-NAV was lower than that of dNAV indicating better suppression of the T1-relaxation echo (panel A). Overall breath-hold acquisition had the highest apparent SNR. The image SNR of dNAV was 23% lower than breath-hold while the SNR of self-NAV was 13% lower (panel B). The self-NAV method took 7 heartbeats per encoding more than dNAV (panel C). However, the imaging time for dNAV didn't include time for scout scans to set up navigators. The Bland-Altman plots showed that the circumferential strain by self-NAV was in better agreement with that by breath-hold (E vs. D) and was more reproducible than dNAV (G vs. F). These results demonstrated that the proposed adaptive method provided better images and strain quantification during free-breathing than dNAV.

Reference Segment Selection

Figure 23:
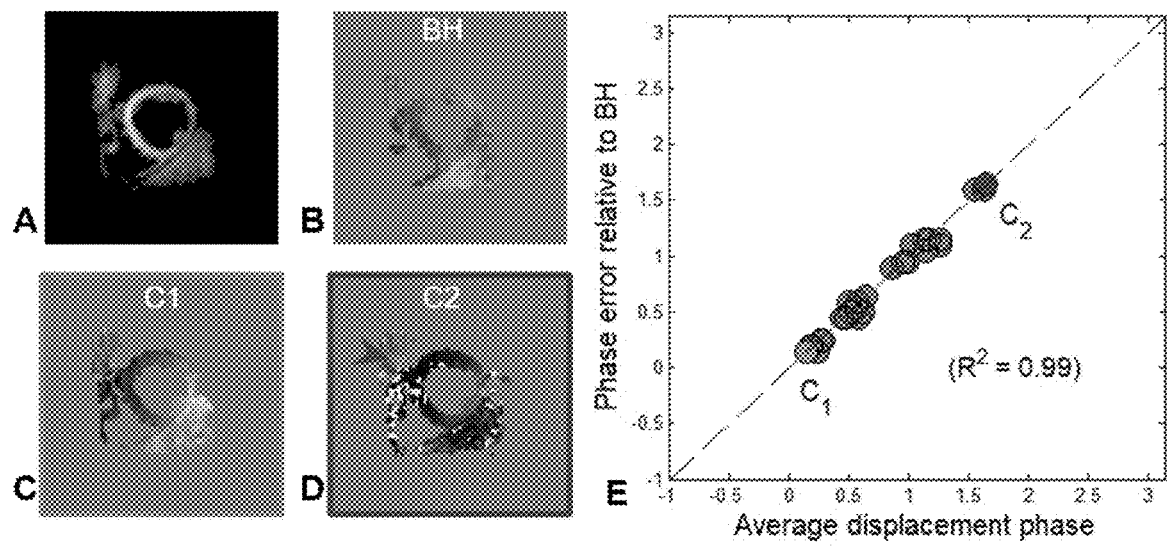
FIG. 23 shows correlation of the averaged displacement phase with the bulk phase error relative to the breath-hold displacement phase in a subject. (A-B) The magnitudes and the phases of the displacement-encoded ste-iNAV acquired with breath-hold (BH) at a late-diastole. The background regions are excluded with a region-of-interest created based on the magnitudes. The displacement phase values in the myocardium are overall trivial. (C-D) The displacement encoded phase extracted from two combinations of free-breathing ste-iNAVs. For $C_1$, the overall displacement phase was small and similar to the breath-hold displacement phase in panel B. For $C_2$, the overall displacement phase is close to $-\pi$ especially in the anterior wall (arrow). (E) In this subject, the averaged displacement phase is highly correlated to the bulk phase error relative to BH with $R^2$=0.99. The two combinations in panels C-D are color-coded. Minimizing the averaged displacement phase identifies the reference segments that provide minimized phase error relative to BH ($C_1$). (BH: breath-hold; The dashed line is the identity line)
Figure 24:
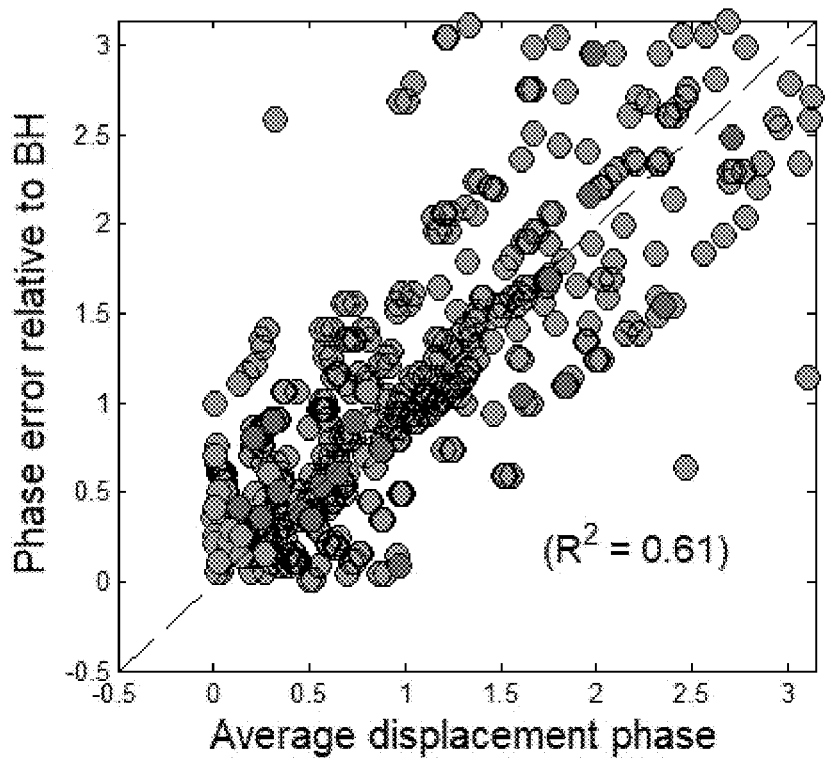
FIG. 24 shows correlation between the averaged displacement phase and the phase error relative to breath-hold data in all healthy subjects. Overall, the phase error relative to BH is correlated with the averaged displacement phase with $R^2$=0.61. The free-breathing ste-iNAV combinations identified by minimizing the average displacement phase are shown in green and the ste-iNAV combinations with the first segments are shown in pink. These results demonstrate that minimizing the averaged displacement phase identifies the reference segments that provide reduced phase error relative to breath-hold. (BH: breath-hold; the dashed line is the identity line)

In a healthy subject, the average phase of free-breathing displacement phase image was highly correlated with the bulk phase error relative to breath-hold (FIG. 23). The data are estimated using ste-iNAVs of one encoding dimension. Minimizing the average displacement phase at late-diastole identified reference segments that can minimize the phase error with breath-hold in the final free-breathing displacement phase images ($C_1$). Overall, the correlation held up in all Healthy subjects with $R^2$ of 0.61 (FIG. 24). The reference segment combinations chosen with minimal displacement phase reduced the phase error with breath-hold compared to those consisting of the first segments (green dots vs. pink dots). These results demonstrate the proposed method for reference segment selection can reduce the overall phase errors due to intra-heartbeat motion relative to breath-hold acquisitions in the displacement phase images.

Discussion

In this study, a self-navigated free-breathing cine DENSE method for myocardial strain imaging was developed. The method uses an adaptive algorithm to reduce the residual energy of the $T_1$-relaxation echo during the acquisition to compensate for striping artifacts and compensates for both the inter-heartbeat motion induced blurriness and the intra-heartbeat motion induced signal cancellation with image-based navigators. Three stopping criteria were designed in the adaptive imaging algorithm to ensure image quality and efficiency. Experiments in healthy subjects demonstrated the adaptive acquisition algorithm and determined the values of the stopping criteria. Evaluation in healthy subjects and patients demonstrated better strain imaging with the presented self-NAV method than the conventional dNAV method.

The self-NAV method is better than dNAV potentially due to multiple reasons. First, minimizing rT1E is more reliable than minimizing dNAV acceptance window for reducing striping artifacts in free-breathing cine DENSE. The 1D navigator position in dNAV is not sufficient to measure the motion of the heart (9) and the respiration pattern measured as diaphragm positions varies significantly from subject to subject. Therefore, the dNAV method produces variable image quality. On the other hand, reduced rT1E directly reduces striping artifacts and improve image quality regardless of the respiration pattern. In addition, diminishing rT1E can reduce residual $T_1$-relaxation signal due to factors other than breathing. For instance, cine DENSE uses prospective ECG triggering and RR interval changes during the acquisition can lead to missing triggering (e.g. skipping a heartbeat). Imaging signal during the heartbeats after the skipped ones is higher than other heartbeats because of the longer relaxation time. Such changes can lead to increased residual signal and artifacts even when respiratory positions are similar. The self-NAV method can reject such data while dNAV cannot.

The phase errors and signal cancellation artifacts induced by intra-heartbeat motion are similar to those in DWI. However, the compensation methods that have been introduced to DWI cannot be directly applied to cine DENSE. The correction for phase error in DWI aims to restore the magnitudes reduced by phase errors. The phase variations among different k-space segments are typically estimated and removed (66). However, cine DENSE is a phase-contrast method with local tissue displacement encoded in the phase of the stimulated-echoes. Therefore, the correction should aim to reduce the signal cancelation without losing displacement-encoded phase information. In this study, the signal cancellation artifacts were compensated with a correction for the global phase differences among k-space segments without changing the spatial variations of phase from the myocardial displacement. Specifically, the correction value was determined so that it maximized the image energy (FIG. 18).

Reconstruction of the same free-breathing datasets with different motion compensations demonstrated that both reducing the rT1E and phase correction were essential for the reconstruction (FIG. 20). The global phase correction improved image quality significantly. Meanwhile, the increase of apparent SNR with phase correction was greater when the T1-relaxation echo was better suppressed (after 20 heartbeats vs. before 20 heartbeats). Similarly, the translation correction improved image quality only when the rT1E was low. These results are likely because when the rT1E is high, the residual $T_1$-echo signal is the main artifact source and hinders the quality of ste-iNAVs, which leads to less improvement from phase correction or translation correction. It is therefore important to suppress the residual $T_1$-relaxation signal before compensating for blurriness and signal cancellation.

A limitation of the current phase error correction is that it does not completely remove the intra-heartbeat motion in the final cine DENSE images. The correction can only compensate for the differences in intra-heartbeat motion induced phase among k-space segments. In addition, the correction only included translations while the intra-heartbeat motion can have other components (65). Future development should investigate more accurate estimation and correction for the phase errors due to intra-heartbeat motion. An estimation of the intra-heartbeat motion or a prior of motion-free reference data would be necessary to correct the phase error accurately. One possible solution is to combine breath-hold and free-breathing acquisition, where one segment of each encoding is acquired during a short breath-hold at the beginning of the scan to get reference segments and the rest of the scan is performed with the adaptive acquisition during free-breathing. With such strategies, the phase errors in the FB data may be compensated accurately and the strain imaging reproducibility can be further improved.

The agreement of free-breathing strain with breath-hold strain was not better than the results in the previous self-navigated free-breathing cine DENSE study (53). The reason was that the strain agreement in patients was not as ideal, which was likely due to the differences in heart position and reduced breath-hold capabilities. In patient imaging, the breath-hold acquisitions were performed at end-inspiration to be consistent with the rest of the exams while the free-breathing acquisitions tend to accept data acquired at end-expiration. In addition, the rT1E in patients was also higher than that in healthy subjects, indicating less effective breath-holds.

The presented method can be extended for multiple applications such as high-resolution strain imaging and free-breathing full-cycle strain imaging. More imaging shots are necessary to image at higher spatial resolution, which can only be performed during free-breathing due to lengthy imaging time. The method does not need extra navigator data allows its use with retrospective triggering for full-cycle DENSE imaging. The presented method can also be combined with in-plane acceleration and/or simultaneous multi-slice imaging to further improve imaging efficiency.

There are a few limitations in the current imaging protocol and method. A large field-of-view was employed. The intra-heartbeat motion correction and inter-heartbeat translation correction are performed off-line. The imaging time of the proposed method is still relatively long compared to breath-hold. The method can be combined with in-plane acceleration (69-74) or simultaneous multi-slice imaging (75, 76) to shorten the imaging time. Specifically, previous study has demonstrated the feasibility of accelerating cine DENSE using compressed sensing method. Only the best matched phase-cycling pair per segment was accepted for reconstruction for a fair comparison with dNAV and BH, whereas more instances of phase-cycling pairs of similar quality can be utilized. We will explore the possibility of utilizing more data and acquiring more instances of matched phase-cycling pairs. Such a method can be useful for imaging subjects where SNR is limited, such as patients with obesity or devices. The reconstruction is performed after the data acquisition is done. An interactive interface that provides visual feedback of images at each iteration and allows user control of the scan (pause, continue or stop the scan) can further improve the reliability of the method (9).

Example MRI System

Figure 25:
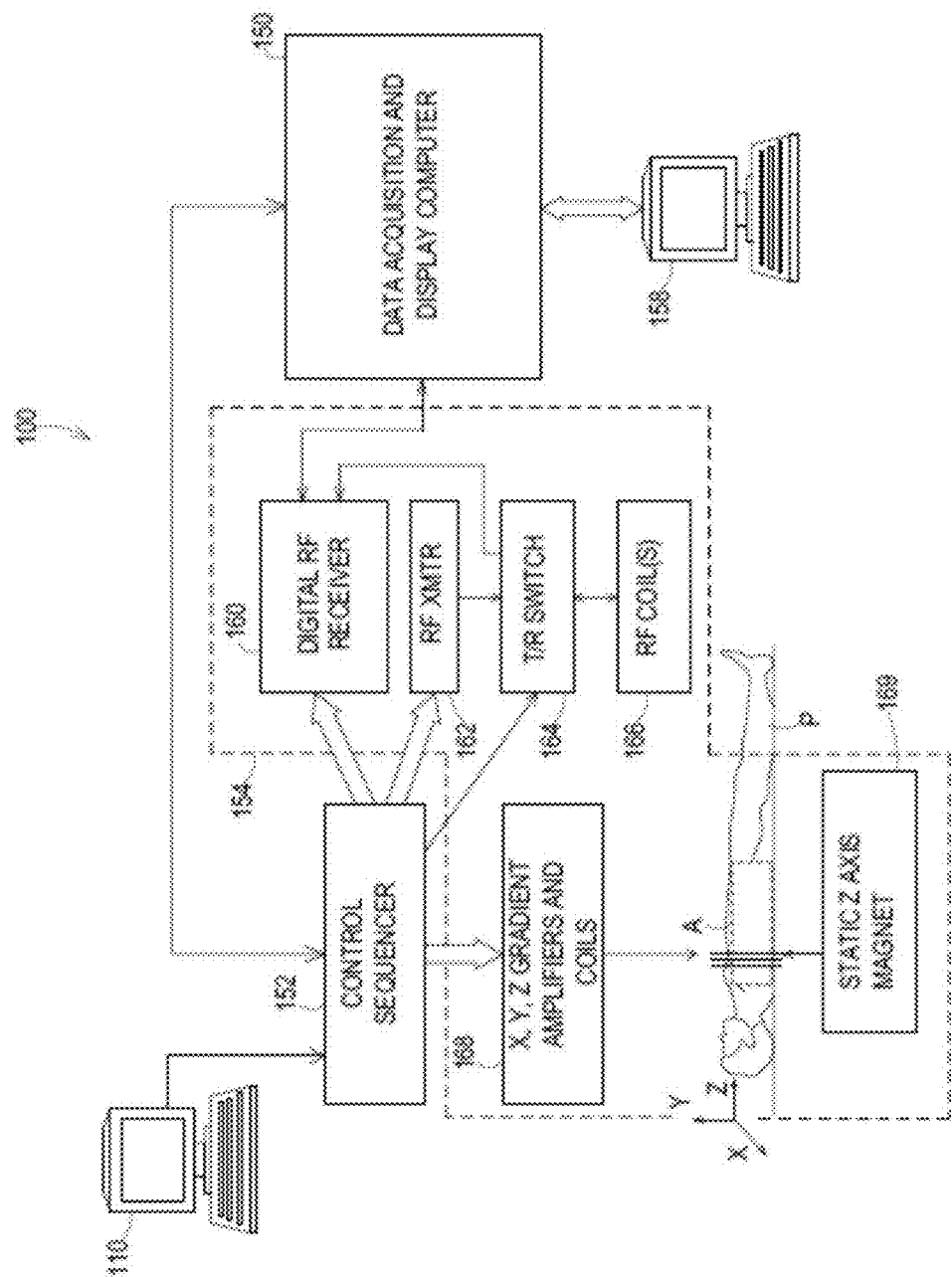
FIG. 25 is a diagram illustrating a magnetic resonance imaging (MRI) system capable of implementing certain aspects of the disclosed technology in accordance with one or more embodiments.

FIG. 25 is a system diagram illustrating an example of a magnetic resonance imaging (MM) system 100, including a data acquisition and display computer 150 coupled to an operator console 110, an MRI real-time control sequencer 152, and an MRI subsystem 154. The MM subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MM subsystem 154 may be controlled in real time by control sequencer 152 to generate magnetic and radio frequency fields that stimulate magnetic resonance phenomena in a subject (patient) P to be imaged, for example, to implement magnetic resonance imaging sequences in accordance with various example embodiments of the disclosed technology described herein. An image of an area of interest A of the subject P (which may also be referred to herein as a "region of interest") may be shown on display 158. The display 158 may be implemented through a variety of output interfaces, including a monitor, printer, or data storage.

The area of interest A corresponds to a region associated with one or more physiological activities in subject P. The area of interest in the example embodiment of FIG. 17 corresponds to a chest region of subject P, but it should be appreciated that the area of interest for purposes of implementing various aspects of the disclosure presented herein is not limited to the chest area. It should be recognized and appreciated that the area of interest in various embodiments may encompass various areas of subject P associated with various physiological characteristics, such as, but not limited to the heart region. Physiological activities that may be evaluated by methods and systems in accordance with various embodiments of the disclosed technology may include, but are not limited to, cardiac activity and conditions. It should be appreciated that any number and type of computer-based medical imaging systems or components, including various types of commercially available medical imaging systems and components, may be used to practice certain aspects of the disclosed technology. Systems as described herein with respect to example embodiments are not intended to be specifically limited to magnetic resonance imaging (MM) implementations or the particular system shown in FIG. 17.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the disclosed technology may include any device configured to acquire, collect, or otherwise obtain data, or to receive data from a data acquisition device within the system, an independent data acquisition device located on-site or off-site, or another data collection, storage, or processing device.

It should be appreciated that any number and type of computer-based medical imaging systems or components, including various types of commercially available medical imaging systems and components, may be used to practice certain aspects of the disclosed technology. Systems as described herein with respect to example embodiments are not intended to be specifically limited to magnetic resonance imaging (MM) implementations or the particular system shown in FIG. 25.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the disclosed technology may include any device configured to acquire, collect, or otherwise obtain data, or to receive data from a data acquisition device within the system, an independent data acquisition device located on-site or off-site, or another data collection, storage, or processing device.

Example Computing System

Figure 26:
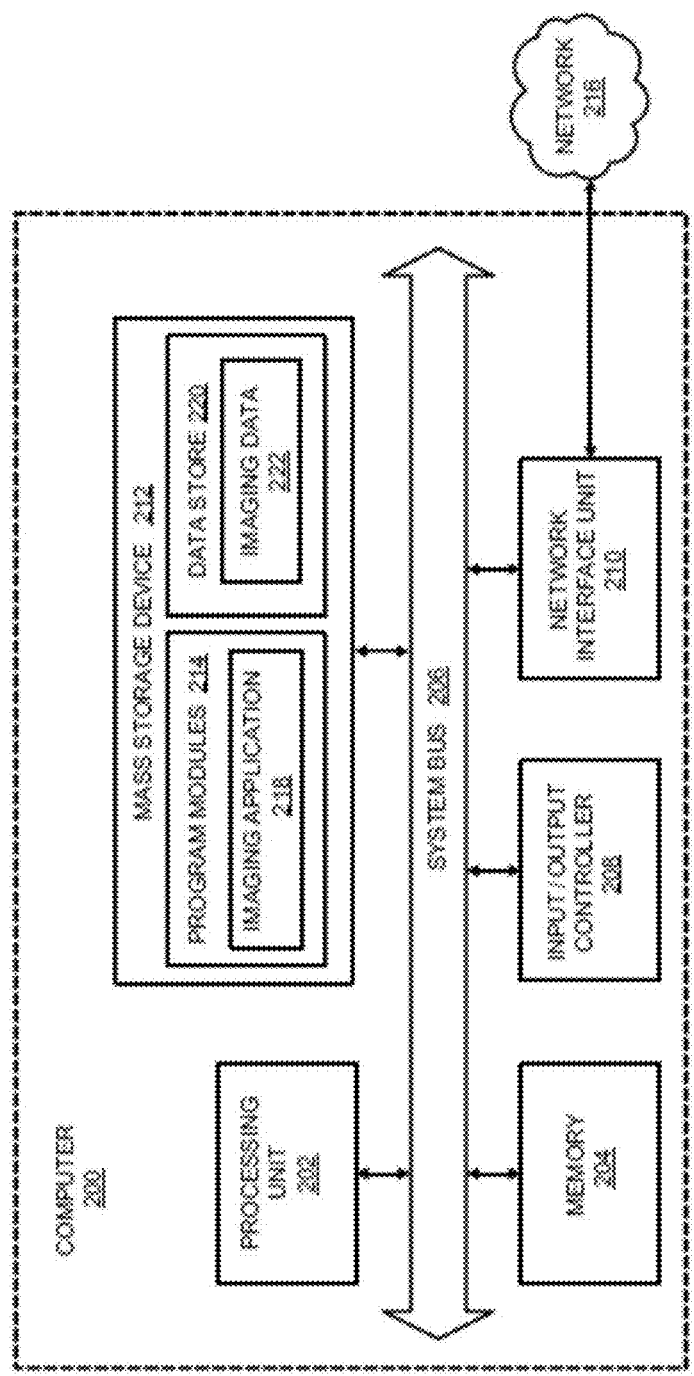
FIG. 26 is a computer architecture diagram showing a computing system capable of implementing certain aspects of the disclosed technology in accordance with one or more embodiments.

FIG. 26 is a computer architecture diagram showing a general computing system capable of implementing aspects of the disclosed technology in accordance with one or more embodiments described herein. A computer 200 may be configured to perform one or more functions associated with embodiments illustrated in one or more of the figures. For example, the computer 200 may be configured to perform various aspects of free-breathing parameter mapping with high-contrast image registration in accordance with example embodiments, such as magnetic resonance imaging data acquisition, image registration, and calculating parameter maps. It should be appreciated that the computer 200 may be implemented within a single computing device or a computing system formed with multiple connected computing devices. The computer 200 may be configured to perform various distributed computing tasks, in which processing and/or storage resources may be distributed among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform associated with embodiments illustrated in one or more of FIGS. 3-12 discussed above. The program modules 214 may include an imaging application 218 for performing data acquisition and/or processing functions as described herein, for example to acquire and/or process image data corresponding to magnetic resonance imaging of an area of interest. The computer 200 can include a data store 220 for storing data that may include imaging-related data 222 such as acquired data from the implementation of magnetic resonance imaging in accordance with various embodiments of the disclosed technology.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. "Computer storage media", "computer-readable storage medium" or "computer-readable storage media" as described herein do not include transitory signals.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems. The computer 200 may also include an input/output controller 208 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 200. The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology.

The computer storage media may also represent secondary storage, whether implemented as hard drives or otherwise. Hard drive implementations may be characterized as solid state, or may include rotating media storing magnetically-encoded information. The program modules 214, which include the imaging application 218, may include instructions that, when loaded into the processing unit 202 and executed, cause the computer 200 to provide functions associated with one or more example embodiments and implementations illustrated in FIGS. 3-12. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202. Encoding the program modules 214 may also transform the physical structure of the computer-storage media. The specific transformation of physical structure may depend on various factors, in different implementations of this description. Examples of such factors may include, but are not limited to, the technology used to implement the computer-storage media, whether the computer storage media are characterized as primary or secondary storage, and the like. For example, if the computer storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

CONCLUSION

The various embodiments described above are provided by way of illustration only and should not be construed to limit the scope of the disclosed technology. Those skilled in the art will readily recognize that various modifications and changes may be made to the disclosed technology without following the example embodiments and implementations illustrated and described herein, and without departing from the spirit and scope of the disclosure and claims here appended. Therefore, other modifications or embodiments as may be suggested by the teachings herein are particularly reserved.

REFERENCE LIST

1. Kim D, Gilson W D, Kramer C M, Epstein F H. Myocardial tissue tracking with two-dimensional cine displacement-encoded MR imaging: development and initial evaluation. Radiology 2004; 230(3):862-871.
2. Zhong X, Spottiswoode B S, Meyer C H, Kramer C M, Epstein F H. Imaging three-dimensional myocardial mechanics using navigator-gated volumetric spiral cine DENSE MRI. Magnetic resonance in medicine 2010; 64(4):1089-1097.
3. Young A A, Li B, Kirton R S, Cowan B R. Generalized spatiotemporal myocardial strain analysis for DENSE and SPAMM imaging. Magnetic resonance in medicine. 2012; 67(6): 1590-9.
4. Lin K, Meng L, Collins J D, Chowdhary V, Markl M, Carr J C. Reproducibility of cine displacement encoding with stimulated echoes (DENSE) in human subjects. Magnetic resonance imaging. 2017; 35:148-53.
5. Gilliam A D, Epstein F H. Automated motion estimation for 2-D cine DENSE MRI. IEEE transactions on medical imaging. 2012; 31(9):1669-81.
6. Auger D A, Bilchick K C, Gonzalez J A, Cui S X, Holmes J W, Kramer C M, et al. Imaging left-ventricular mechanical activation in heart failure patients using cine DENSE MRI: Validation and implications for cardiac resynchronization therapy. Journal of Magnetic Resonance Imaging. 2017.
7. Mangion K, Carrick D, Carberry J, Mahrous A, McComb C, Gao H, et al. Comparative prognostic value of myocardial strain derived from DENSE CMR: the British Heart Foundation MR-MI study. The Lancet. 2017; 389: S66.
8. Jing L, Binkley C M, Suever J D, Umasankar N, Haggerty C M, Rich J, et al. Cardiac remodeling and dysfunction in childhood obesity: a cardiovascular magnetic resonance study. Journal of Cardiovascular Magnetic Resonance. 2016; 18(1):28.
9. Ehman R L, Felmlee J P. Adaptive technique for high-definition MR imaging of moving structures. Radiology. 1989; 173(1):255-63.
10. Larson A C, White R D, Laub G, McVeigh E R, Li D, Simonetti O P. Self-gated cardiac cine MRI. Magnetic Resonance in Medicine. 2004; 51(1):93-102.
11. Uribe S, Muthurangu V, Boubertakh R, Schaeffter T, Razavi R, Hill D L, et al. Whole-heart cine MRI using real-time respiratory self-gating. Magnetic Resonance in Medicine. 2007; 57(3):606-13.
12. Usman M, Atkinson D, Odille F, Kolbitsch C, Vaillant G, Schaeffter T, et al. Motion corrected compressed sensing for free-breathing dynamic cardiac MRI. Magnetic resonance in medicine. 2013; 70(2):504-16.
13. Kellman P, Larson A C, Hsu L Y, Chung Y C, Simonetti O P, McVeigh E R, et al. Motion-corrected free-breathing delayed enhancement imaging of myocardial infarction. Magnetic resonance in medicine. 2005; 53(1):194-200.
14. Stehning C, Bornert P, Nehrke K, Eggers H, Stuber M. Free-breathing whole-heart coronary MRA with 3D radial SSFP and self-navigated image reconstruction. Magnetic resonance in medicine. 2005; 54(2):476-80.
15. Henningsson M, Koken P, Stehning C, Razavi R, Prieto C, Botnar R M. Whole-heart coronary MR angiography with 2D self-navigated image reconstruction. Magnetic resonance in medicine. 2012; 67(2):437-45.
16. Lai P, Larson A C, Bi X, Jerecic R, Li D. A dual-projection respiratory self-gating technique for whole-heart coronary MRA. Journal of Magnetic Resonance Imaging. 2008; 28(3):612-20.
17. Chow K, Yang Y, Shaw P, Kramer C M, Salerno M. Robust free-breathing SASHA T 1 mapping with high-contrast image registration. Journal of Cardiovascular Magnetic Resonance. 2016; 18(1):47.
18. Zhong X, Spottiswoode B S, Cowart E A, Gilson W D, Epstein F H. Selective suppression of artifact-generating echoes in cine DENSE using through-plane dephasing. Magnetic resonance in medicine. 2006; 56(5):1126-31.
19. Mills P, Chew W, Litt L, Moseley M. Localized imaging using stimulated echoes. Magnetic resonance in medicine 1987; 5(4):384-389.
20. Gudbjartsson H, Patz S. The Rician distribution of noisy MM data. Magnetic resonance in medicine 1995; 34(6): 910-914.
21. Goto Y, Ishida M, Takase S, Sigfridsson A, Uno M, Nagata M, et al. Comparison of Displacement Encoding With Stimulated Echoes to Magnetic Resonance Feature Tracking for the Assessment of Myocardial Strain in Patients With Acute Myocardial Infarction. The American Journal of Cardiology. 2017; 119(10):1542-7.
22. Kihlberg J, Haraldsson H, Sigfridsson A, Ebbers T, Engvall J E. Clinical experience of strain imaging using DENSE for detecting infarcted cardiac segments. Journal of Cardiovascular Magnetic Resonance. 2015; 17(1):50.
23. Winkelmann S, Schaeffter T, Koehler T, Eggers H, Doessel O. An optimal radial profile order based on the Golden Ratio for time-resolved MRI. IEEE transactions on medical imaging. 2007; 26(1):68-76.
24. Kim Y C, Narayanan S S, Nayak K S. Flexible retrospective selection of temporal resolution in real-time speech MRI using a golden-ratio spiral view order. Magnetic resonance in medicine. 2011; 65(5):1365-71.

25. Aletras A H, Balaban R S, Wen H. High-resolution strain analysis of the human heart with fast-DENSE. Journal of Magnetic Resonance. 1999; 140(1):41-57.
26. Walsh D O, Gmitro A F, Marcellin M W. Adaptive reconstruction of phased array MR imagery. Magnetic Resonance in Medicine. 2000; 43(5):682-90.
27. Fessler J A, Sutton B P. Nonuniform fast Fourier transforms using min-max interpolation. IEEE Transactions on Signal Processing. 2003; 51(2):560-74.
28. Wehner G J, Suever J D, Haggerty C M, Jing L, Powell D K, Hamlet S M, et al. Validation of in vivo 2D displacements from spiral cine DENSE at 3T. Journal of Cardiovascular Magnetic Resonance. 2015; 17(1):5.
29. Fahmy A S, Ibrahim E-SH, Osman N F. Spectrally-Presaturated Modulation (SPM): An efficient fat suppression technique for STEAM-based cardiac imaging sequences. Magnetic resonance imaging. 2017; 37:209-15.
30. Zhong X, Helm P A, Epstein F H. Balanced multipoint displacement encoding for DENSE MRI. Magnetic resonance in medicine. 2009; 61(4):981-8.
31. Bilchick K C, Kuruvilla S, Hamirani Y S, Ramachandran R, Clarke S A, Parker K M, et al. Impact of mechanical activation, scar, and electrical timing on cardiac resynchronization therapy response and clinical outcomes. Journal of the American College of Cardiology. 2014; 63(16):1657-66.
32. Constantinides C D, Atalar E, McVeigh E R. Signal-to-noise measurements in magnitude images from NMR phased arrays. Magnetic Resonance in Medicine. 1997; 38(5):852-7.
33. Ghiglia D C, Pritt M D. Two-dimensional phase unwrapping: theory, algorithms, and software: Wiley New York; 1998.
34. Spottiswoode B S, Zhong X, Hess A T, Kramer C, Meintjes E M, Mayosi B M, et al. Tracking myocardial motion from cine DENSE images using spatiotemporal phase unwrapping and temporal fitting. IEEE transactions on medical imaging. 2007; 26(1):15-30.
35. Kim D, Gilson W D, Kramer C M, Epstein F H. Myocardial tissue tracking with two-dimensional cine displacement-encoded MR imaging: development and initial evaluation. Radiology. 2004; 230(3):862-71.
36. Auger D A, Bilchick K C, Gonzalez J A, Cui S X, Holmes J W, Kramer C M, et al. Imaging left-ventricular mechanical activation in heart failure patients using cine DENSE MRI: Validation and implications for cardiac resynchronization therapy. Journal of Magnetic Resonance Imaging. 2017.
37. Mangion K, Carrick D, Carberry J, Mahrous A, McComb C, Gao H, et al. Comparative prognostic value of myocardial strain derived from DENSE CMR: the British Heart Foundation MR-MI study. The Lancet. 2017; 389:S66.
38. Jing L, Pulenthiran A, Nevius C D, Mejia-Spiegeler A, Suever J D, Wehner G J, et al. Impaired right ventricular contractile function in childhood obesity and its association with right and left ventricular changes: a cine DENSE cardiac magnetic resonance study. Journal of Cardiovascular Magnetic Resonance. 2017; 19(1):49.
39. Kihlberg J, Haraldsson H, Sigfridsson A, Ebbers T, Engvall J E. Clinical experience of strain imaging using DENSE for detecting infarcted cardiac segments. Journal of Cardiovascular Magnetic Resonance. 2015; 17(1):50.
40. Ehman R L, Felmlee J P. Adaptive technique for high-definition MR imaging of moving structures. Radiology. 1989; 173(1):255-63.
41. Zhong X, Spottiswoode B S, Meyer C H, Kramer C M, Epstein F H. Imaging three-dimensional myocardial mechanics using navigator-gated volumetric spiral cine DENSE MRI. Magnetic resonance in medicine. 2010; 64(4):1089-97.
42. Hamlet S M, Haggerty C M, Suever J D, Wehner G J, Andres K N, Powell D K, et al. Optimal configuration of respiratory navigator gating for the quantification of left ventricular strain using spiral cine displacement encoding with stimulated echoes (DENSE) MM. Journal of Magnetic Resonance Imaging. 2017; 45(3):786-94.
43. Sachs T S, Meyer C H, Pauly J M, Hu B S, Nishimura D G, Macovski A. The real-time interactive 3-D-DVA for robust coronary MRA. IEEE transactions on medical imaging. 2000; 19(2):73-9.
44. Nehrke K, Bornert P, Manke D, Bock J C. Free-breathing cardiac MR imaging: study of implications of respiratory motion—initial results. Radiology. 2001; 220(3):810-5.
45. Taylor A M, Jhooti P, Wiesmann F, Keegan J, Firmin D N, Pennell D J. MR navigator-echo monitoring of temporal changes in diaphragm position: implications for MR coronary angiography. Journal of Magnetic Resonance Imaging. 1997; 7(4):629-36.
46. Larson A C, Kellman P, Arai A, Hirsch G A, McVeigh E, Li D, et al. Preliminary investigation of respiratory self-gating for free-breathing segmented cine MM. Magnetic Resonance in Medicine: An Official Journal of the International Society for Magnetic Resonance in Medicine. 2005; 53(1):159-68.
47. Leung A O, Paterson I, Thompson R B. Free-breathing cine MM. Magnetic resonance in medicine. 2008; 60(3): 709-17.
48. Liu J, Spincemaille P, Codella N C, Nguyen T D, Prince M R, Wang Y. Respiratory and cardiac self-gated free-breathing cardiac CINE imaging with multiecho 3D hybrid radial SSFP acquisition. Magnetic resonance in medicine. 2010; 63(5):1230-7.
49. Feng L, Axel L, Chandarana H, Block K T, Sodickson D K, Otazo R. XD-GRASP: golden-angle radial MRI with reconstruction of extra motion-state dimensions using compressed sensing. Magnetic resonance in medicine. 2016; 75(2):775-88.
50. Sussman M S, Stainsby J A, Robert N, Merchant N, Wright G A. Variable-density adaptive imaging for high-resolution coronary artery MRI. Magnetic Resonance in Medicine: An Official Journal of the International Society for Magnetic Resonance in Medicine. 2002; 48(5):753-64.
51. Hardy C J, Zhao L, Zong X, Saranathan M, Yucel E K. Coronary M R angiography: respiratory motion correction with BACSPIN. Journal of Magnetic Resonance Imaging. 2003; 17(2): 170-6.
52. Chow K, Yang Y, Shaw P, Kramer C M, Salerno M. Robust free-breathing SASHA T 1 mapping with high-contrast image registration. Journal of Cardiovascular Magnetic Resonance. 2016; 18(1):47.
53. Cai X, Epstein F H. Free-breathing cine DENSE MM using phase cycling with matchmaking and stimulated-echo image-based navigators. Magnetic resonance in medicine. 2018.
54. Gilson W D, Yang Z, French B A, Epstein F H. Complementary displacement-encoded MRI for contrast-enhanced infarct detection and quantification of myocardial function in mice. Magnetic Resonance in Medicine: An Official Journal of the International Society for Magnetic Resonance in Medicine. 2004; 51(4):744-52.

55. Anderson A W, Gore J C. Analysis and correction of motion artifacts in diffusion weighted imaging. Magnetic resonance in medicine. 1994; 32(3):379-87.
56. Liu C, Bammer R, Kim Dh, Moseley M E. Self-navigated interleaved spiral (SNAILS): application to high-resolution diffusion tensor imaging. Magnetic Resonance in Medicine: An Official Journal of the International Society for Magnetic Resonance in Medicine. 2004; 52(6): 1388-96.
57. Johnson C L, McGarry M D, Van Houten E E, Weaver J B, Paulsen K D, Sutton B P, et al. Magnetic resonance elastography of the brain using multishot spiral readouts with self-navigated motion correction. Magnetic resonance in medicine. 2013; 70(2):404-12.
58. Mills P, Chew W, Litt L, Moseley M. Localized imaging using stimulated echoes. Magnetic resonance in medicine. 1987; 5(4):384-9.
59. Shechter G, McVeigh E R, editors. MR motion correction of 3D affine deformations. Proceedings Int Soc Mag Reson Med; 2003: Citeseer.
60. Fessler J A, Sutton B P. Nonuniform fast Fourier transforms using min-max interpolation. IEEE Transactions on Signal Processing. 2003; 51(2):560-74.
61. Zhong X, Helm P A, Epstein F H. Balanced multipoint displacement encoding for DENSE MM. Magnetic resonance in medicine. 2009; 61(4):981-8.
62. Gudbjartsson H, Patz S. The Rician distribution of noisy MRI data. Magnetic resonance in medicine. 1995; 34(6): 910-4.
63. Dietrich O, Raya J G, Reeder S B, Ingrisch M, Reiser M F, Schoenberg S O. Influence of multichannel combination, parallel imaging and other reconstruction techniques on MM noise characteristics. Magnetic resonance imaging. 2008; 26(6):754-62.
64. Irarrazabal P, Meyer C H, Nishimura D G, Macovski A. Inhomogeneity correction using an estimated linear field map. Magnetic resonance in medicine. 1996; 35(2):278-82.
65. Noll D C, Meyer C H, Pauly J M, Nishimura D G, Macovski A. A homogeneity correction method for magnetic resonance imaging with time-varying gradients. IEEE transactions on medical imaging. 1991; 10(4):629-37.
66. Segmentation AHAWGoM, Imaging: RfC, Cerqueira M D, Weissman N J, Dilsizian V, Jacobs A K, et al. Standardized myocardial segmentation and nomenclature for tomographic imaging of the heart: a statement for healthcare professionals from the Cardiac Imaging Committee of the Council on Clinical Cardiology of the American Heart Association. Circulation. 2002; 105(4):539-42.
67. Spottiswoode B S, Zhong X, Hess A T, Kramer C, Meintjes E M, Mayosi B M, et al. Tracking myocardial motion from cine DENSE images using spatiotemporal phase unwrapping and temporal fitting. IEEE transactions on medical imaging. 2007; 26(1):15-30.
68. Spottiswoode B S, Zhong X, Lorenz C H, Mayosi B M, Meintjes E M, Epstein F H. Motion-guided segmentation for cine DENSE MM. Medical image analysis. 2009; 13(1):105-15.
69. Griswold M A, Jakob P M, Heidemann R M, Nittka M, Jellus V, Wang J, et al. Generalized autocalibrating partially parallel acquisitions (GRAPPA). Magnetic Resonance in Medicine: An Official Journal of the International Society for Magnetic Resonance in Medicine. 2002; 47(6):1202-10.
70. Pruessmann K P, Weiger M, Scheidegger M B, Boesiger P. SENSE: sensitivity encoding for fast MM. Magnetic resonance in medicine. 1999; 42(5):952-62.
71. Lustig M, Donoho D, Pauly J M. Sparse M M: The application of compressed sensing for rapid MR imaging. Magnetic Resonance in Medicine: An Official Journal of the International Society for Magnetic Resonance in Medicine. 2007; 58(6):1182-95.
72. Lustig M, Santos J M, Donoho D L, Pauly J M, editors. kt SPARSE: High frame rate dynamic MM exploiting spatio-temporal sparsity. Proceedings of the 13th Annual Meeting of ISMRM, Seattle; 2006.
73. Pedersen H, Kozerke S, Ringgaard S, Nehrke K, Kim W Y. k-t PCA: temporally constrained k-t BLAST reconstruction using principal component analysis. Magnetic resonance in medicine. 2009; 62(3):706-16.
74. Lingala S G, Hu Y, DiBella E, Jacob M. Accelerated dynamic MRI exploiting sparsity and low-rank structure: kt SLR. IEEE transactions on medical imaging. 2011; 30(5):1042-54.
75. Barth M, Breuer F, Koopmans P J, Norris D G, Poser B A. Simultaneous multislice (SMS) imaging techniques. Magnetic resonance in medicine. 2016; 75(1):63-81.
76. Breuer F A, Blaimer M, Mueller M F, Seiberlich N, Heidemann R M, Griswold M A, et al. Controlled aliasing in volumetric parallel imaging (2D CAIPIRINHA). Magnetic Resonance in Medicine: An Official Journal of the International Society for Magnetic Resonance in Medicine. 2006; 55(3):549-56.

What is claimed is:

1. A method comprising:
acquiring magnetic resonance imaging data, for a plurality of images of a subject, wherein the plurality of images comprises respectively phase-cycled interleaves of the imaging data that populate a respective segment of the images;
calculating residual T1 energy values for each of the images;
calculating a respective average of corresponding residual T1 energy values for a plurality of pairs of the images within the respective segment;
selecting a first image and a second image as a first matched pair of images, wherein the first matched pair of images has a lowest average of corresponding residual T1 energy values in comparison to other unselected pairs of the images, and wherein selecting the first and second images, yielding the lowest average of corresponding residual T1 energy values, comprises matching the first and second images in the spatial domain to a respective position on the subject being imaged;
subtracting the first image from the second image to suppress artifacts within a resulting image;
using the resulting image to reconstruct an image-based navigator (iNav) for the segment, wherein the iNav includes stimulated-echo images with suppressed artifacts (ste-iNAVs).

2. The method of claim 1, further comprising:
iteratively matching additional pairs of the images within respective segments of images, wherein the additional pairs of the images have a lowest yielded average of the pairs of respective residual T1 energy values;
subtracting iteratively matched additional images to suppress artifacts;
reconstructing respective ste-iNavs within the respective segment for the iteratively matched images; and comparing the reconstructed iNavs to identify motion correction values for the segment.

3. The method of claim 2, wherein the iteratively matched images comprise images having a same displacement encoding and a same k-space trajectory in a common gradient domain.

4. The method of claim 1, wherein the image data is cardiac image data, the first matched pair of images relate to a matched respiratory position of the subject, and the segment of images corresponds to a period of time between heartbeats of the subject.

5. The method of claim 4, wherein the image data is acquired during free breathing of the subject, and the suppressed artifacts comprise suppressed T1-relaxation echo artifacts on the ste-iNavs.

6. The method of claim 1, wherein the images are generated as respective frames of image data with free-breathing displacement-encoding with stimulated echoes (DENSE).

7. The method of claim 6, wherein the frames of image data are generated for respective segments with spiral cine DENSE acquisition to populate a k-space representation of the segment.

8. The method of claim 7, wherein an approximate location of a T1 relaxation echo in the images is determined by a displacement-encoding frequency $k_e$ and the residual T1-relaxation echo energy is calculated by summing data over a predetermined region of the k-space representation corresponding to $k > k_e/2$.

9. The method of claim 1, wherein the phase cycled interleaves are subject to either simple displacement encoding or balanced displacement encoding.

10. The method of claim 1, wherein the first image and the second image correspond to different phase cycles of an encoding signal.

11. A method comprising:
sampling segments of image data acquired during magnetic resonance imaging, wherein the segments include frames of images, wherein each frame includes respective phase-cycled interleaves of the imaging data acquired during a respective phase of an encoding signal, wherein the sampling comprises:
calculating residual T1 energy values for each of the images;
selecting a first image and a second image as a first matched pair of images, wherein the first matched pair of images has a lowest average of corresponding residual T1 energy values in comparison to other unselected pairs of the images;
subtracting the first image from the second image to suppress artifacts within a resulting image;
iteratively evaluating the sampling of all of the segments by:
selecting a target segment having a highest residual T1 energy value in comparison to unselected segments;
repeating the magnetic resonance imaging for the target segment and acquiring new image data for the target segment;
sampling the new image data and calculating a new residual T1 energy value for the target segment;
repeating the selecting of a target segment until satisfying at least one of a set of stopping criteria; and
reconstructing an image-based navigator (iNav) for the respective segments using a last resulting image for each segment, wherein the iNav includes stimulated-echo images with suppressed artifacts (ste-iNAVs).

12. The method of claim 11, wherein the sampling, evaluating, and reconstructing are repeated for all encoding dimensions of the magnetic resonance imaging.

13. The method of claim 11, wherein the sampling, evaluating and reconstructing are repeated for all dimensions in the image domain space.

14. The method of claim 11, wherein the set of stopping criteria comprises at least one of a bottom threshold for the residual T1 energy values, a lowest threshold for a decrease in percentage change of consecutive residual T1 energy values, and a time limit.

15. A method comprising:
acquiring magnetic resonance imaging data, for a plurality of images of a subject, wherein the plurality of images comprises respectively phase-cycled interleaves of the imaging data that populate a respective segment of the images;
calculating residual T1 energy values for each of the images;
iteratively matching pairs of the images within respective segments of images that have a lowest yielded average of pairs of respective residual T1 energy values;
subtracting iteratively matched images to suppress artifacts;
reconstructing respective ste-iNavs within the respective segment for the iteratively matched images; and
comparing the reconstructed iNavs in at least one k space representation of each respective segment to identify 2D translation motion and translation motion correction values for the segments;
correcting phase error for the translation motion in the k space representation by:
for each encoding dimension, selecting a reference segment from the respective segments of the image data;
using the reference segment to correct other segments of the respective segments by:
for each other segment, maximizing an energy function (E(θ)) for a complex sum of the reference segment (Sref) and each of said other segments (Scor):

$$E(\theta) = \|S_{ref} + S_{cor} e^{-i\theta}\|,$$

wherein a correction value θ that maximizes the energy function is a correction value for a respective other segment (Scor); and
applying the correction value to images within each of said other segments.

16. The method of claim 15, wherein correcting phase error for each segment further comprises:
calculating a respective correction value for each segment;
smoothing the respective correction values;
linearly interpolating an overall correction value; and
applying the overall correction value to k space representations of images within each of said other segments.

17. The method of claim 16, further comprising reducing bulk phase error in a final displacement encoded phase image that minimizes an average displacement phase at a given point of acquiring the image data.

18. A system comprising:
at least one processor;
at least one memory device coupled to the processor and storing computer-readable instructions which, when executed by the at least one processor, cause the system to perform functions that comprise:

acquiring magnetic resonance imaging data, for a plurality of images of a subject, wherein the plurality of images comprises respectively phase-cycled interleaves of the imaging data that populate a respective segment of the images;

calculating residual T1 energy values for each of the images;

calculating a respective average of corresponding residual T1 energy values for a plurality of pairs of the images within the respective segment;

selecting a first image and a second image as a first matched pair of images, wherein the first matched pair of images has a lowest average of corresponding residual T1 energy values in comparison to other unselected pairs of the images, and wherein selecting the first and second images, yielding the lowest average of corresponding residual T1 energy values, comprises matching the first and second images in the spatial domain to a respective position on the subject being imaged;

subtracting the first image from the second image to suppress artifacts within a resulting image; and using the resulting image to reconstruct an image-based navigator (iNav) for the segment, wherein the iNav includes stimulated-echo images with suppressed artifacts (ste-iNAVs).

\* \* \* \* \*